US012649938B2

(12) United States Patent
Choi et al.

(10) Patent No.: US 12,649,938 B2
(45) Date of Patent: Jun. 9, 2026

(54) **L-METHIONINE PRODUCING MICROORGANISM TO WHICH PROTEIN ENCODED BY FOREIGN *metZ* GENE IS INTRODUCED AND METHOD FOR PRODUCING L-METHIONINE USING SAME**

(71) Applicant: CJ CHEILJEDANG CORPORATION, Seoul (KR)

(72) Inventors: Sol Choi, Seoul (KR); Jin Nam Lee, Seoul (KR); Hee Ju Kim, Seoul (KR); Jin Ah Rho, Seoul (KR); Han Hyoung Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 1063 days.

(21) Appl. No.: 17/754,988

(22) PCT Filed: Oct. 28, 2020

(86) PCT No.: PCT/KR2020/014780
§ 371 (c)(1),
(2) Date: Nov. 14, 2022

(87) PCT Pub. No.: WO2021/085999
PCT Pub. Date: May 6, 2021

(65) Prior Publication Data
US 2023/0212623 A1 Jul. 6, 2023

(30) Foreign Application Priority Data
Oct. 28, 2019 (KR) ........................ 10-2019-0134797

(51) Int. Cl.
*C12P 13/12* (2006.01)
*C12N 9/10* (2006.01)
*C12N 15/77* (2006.01)

(52) U.S. Cl.
CPC ............ *C12P 13/12* (2013.01); *C12N 9/1085* (2013.01); *C12N 15/77* (2013.01); *C12Y 205/01* (2013.01); *C12N 2800/101* (2013.01)

(58) Field of Classification Search
None
See application file for complete search history.

(56) References Cited

U.S. PATENT DOCUMENTS

| | | | |
|---|---|---|---|
| 7,662,943 B2 | 2/2010 | Park et al. | |
| 10,273,491 B2 | 4/2019 | Lee et al. | |
| 10,584,338 B2 | 3/2020 | Lee et al. | |
| 12,203,117 B2 * | 1/2025 | Choi ........................ | C12P 13/12 |
| 12,331,339 B2 * | 6/2025 | Choi ........................ | C07K 14/34 |
| 2003/0162267 A1 | 8/2003 | Pompejus et al. | |
| 2004/0043953 A1 | 3/2004 | Pompejus et al. | |
| 2006/0084152 A1 * | 4/2006 | Pompejus .............. | C07K 14/34 |
| | | | 435/115 |
| 2009/0298137 A1 | 12/2009 | Zelder et al. | |
| 2010/0009416 A1 | 1/2010 | Zelder et al. | |
| 2010/0184164 A1 | 7/2010 | Kim et al. | |
| 2013/0273614 A1 | 10/2013 | Kim et al. | |
| 2018/0223319 A1 * | 8/2018 | Soucaille ....... | C12Y 205/01049 |
| 2018/0355389 A1 | 12/2018 | Lee et al. | |

FOREIGN PATENT DOCUMENTS

| | | |
|---|---|---|
| JP | 2009-501550 | 1/2009 |
| JP | 2010-523145 | 7/2010 |
| KR | 10-0905381 B1 | 6/2009 |
| KR | 2012-0108844 A | 10/2012 |
| KR | 10-1250651 B1 | 4/2013 |
| KR | 10-1783170 B1 | 9/2017 |
| RU | 2447146 | 4/2012 |
| WO | WO 02/051231 A1 | 7/2002 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Accession Q7NUH3. Dec. 15, 2003 (Year: 2003).*
Accession A0A059FLS2. Jul. 9, 2014 (Year: 2014).*
Accession Q3J5D4 Nov. 8, 2005 (Year: 2005).*
Extended European Search Report in European Patent Application No. 20883239.4, mailed Apr. 18, 2023.
Office Action in Japanese Patent Application No. 2022-523724, dated Mar. 14, 2023.
Kromer JO et al., J Bacteriol 188(2):609-618, 2006.
Yeom HJ et al., J Microbiol Biotechnol 14(2):373-378, 2004.
Hwang BJ et al., J Bacteriol 184(5):1277-1286, 2002.
Pearson et al., Proc. Natl. Acad. Sci. USA 85:2444, 1988.
Sitnicka et al. "Functional Analysis of Genes". Advances in Cell Biology. 2010, vol. 2. 1-16; Sambrook et al. Molecular Cloning 2012.
Nakashima N et al., "Bacterial cellular engineering by genome editing and gene silencing". Int J Mol Sci. 2014;15(2):2773-2793.
Sambrook et al. Molecular Cloning 2012.
Rey et al., J. Biotechnol. 103:51-65, 2003.
Van der Rest et al., Appl Microbiol Biotechnol 52:541-545, 1999.
Office Action received in Brazilian Patent Application No. BR112022007907-9, dated Sep. 11, 2024.

(Continued)

*Primary Examiner* — Christian L Fronda

(74) *Attorney, Agent, or Firm* — KNOBBE, MARTENS, OLSON & BEAR, LLP

(57) ABSTRACT

An L-methionine-producing microorganism into which a *metZ* gene is introduced and a method of producing L-methionine using the same.

7 Claims, 1 Drawing Sheet
Specification includes a Sequence Listing.

(56)     References Cited

OTHER PUBLICATIONS

Taté, Rosarita, et al. "The Rhizobium etli *metZ* gene is essential for methionine biosynthesis and nodulation of Phaseolus vulgaris." Molecular plant-microbe interactions 12.1 (1999): 24-34.
Office Action received in Russian Application No. 2022111721, dated Dec. 21, 2022.

* cited by examiner

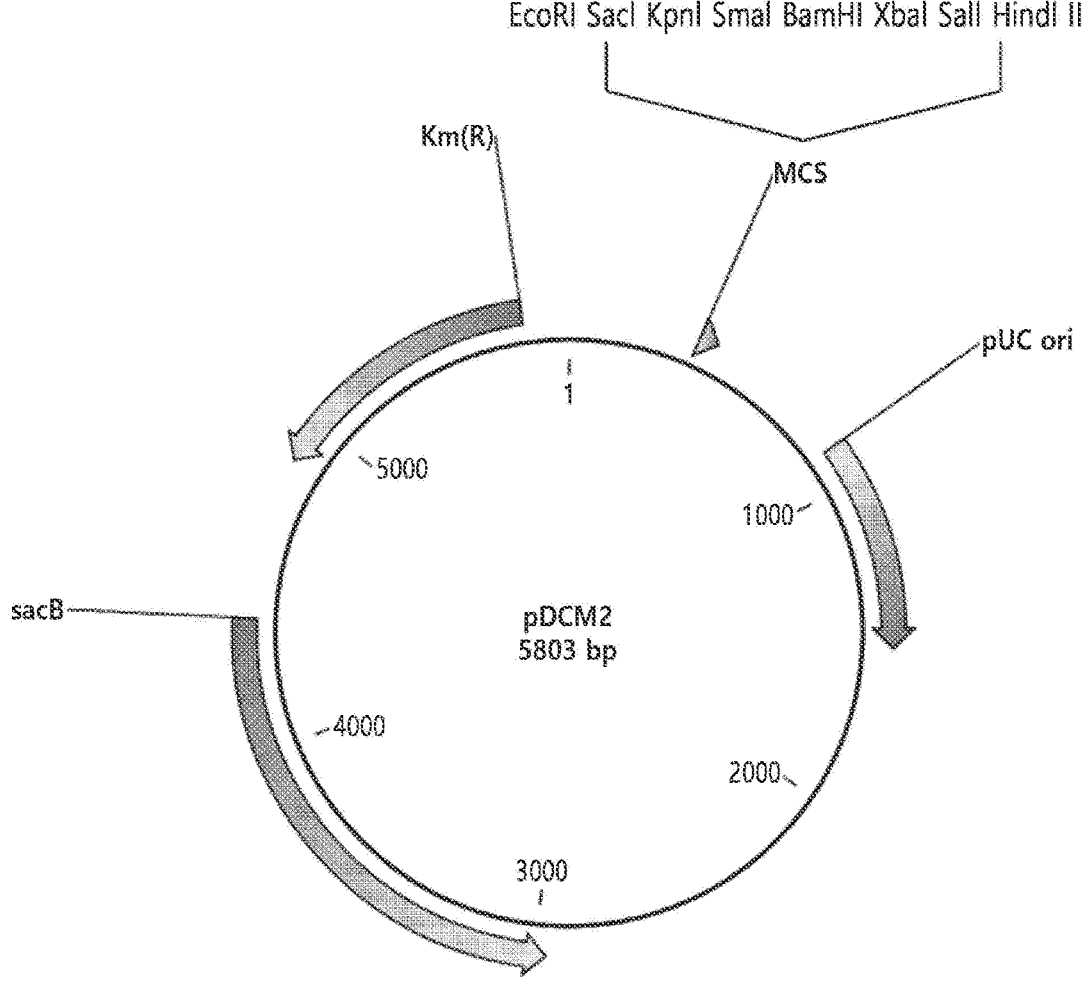

SEQUENCE LISTING

<160> NUMBER OF SEQ ID NOS: 81

<210> SEQ ID NO 1
<211> LENGTH: 2642
<212> TYPE: DNA

```
<213> ORGANISM: Corynebacterium glutamicum

<400> SEQUENCE: 1
ctcccgcgca ctgctgcaat ccgcaccgtg cccaatgatg gtggttcgcc cacctgagaa         60
gattaagaag tagtttcttt taagtttcga tgccccggtt tcctgatttt gtgcagggag        120
gccggggcat tggtgtttgc gggttagttc gggccattcg aaagggagaa accaagggca        180
gccagacaga cgtgccaaga atctggattt ccgccaggtt ttggcacgcc cgtctggttt        240
aggcaatgag ataccgaaca cacgtgccaa aagttcggct ttttcgccga tcttgtcacg        300
cctgcctggt ttgtcttgta aagagtgatt tcatggccga gactcctaaa agtttgacct        360
cacaggattg cttctaaggg cctctccaat ctccactgag gtacttaatc cttccgggga        420
attcgggcgc ttaaatcgag aaattaggcc atcacctttt aataacaata caatgaataa        480
ttggaatagg tcgacacctt tggagcggag ccggttaaaa ttggcagcat tcaccgaaag        540
aaaaggagaa ccacatgctt gccctaggtt ggattacatg gatcattatt ggtggtctag        600
ctggttggat tgcctccaag attaaaggca ctgatgctca gcaaggaatt ttgctgaaca        660
tagtcgtcgg tattatcggt ggtttgttag gcggctggct gcttggaatc ttcggagtgg        720
atgttgccgg tggcggcttg atcttcagct tcatcacatg tctgattggt gctgtcattt        780
tgctgacgat cgtgcagttc ttcactcgga agaagtaatc tgctttaaat ccgtagggcc        840
tgttgatatt tcgatatcaa caggcctttt ggtcattttg gggtggaaaa agcgctagac        900
ttgcctgtgg attaaaacta tacgaaccgg tttgtctata ttggtgttag acagttcgtc        960
gtatcttgaa acagaccaac ccgaaaggac gtggccgaac gtggctgcta gcgcttcagg       1020
caagagtaaa acaagtgccg gggcaaaccg tcgtcgcaat cgaccaagcc cccgacagcg       1080
tctcctcgat agcgcaacca accttttcac cacagaaggt attcgcgtca tcggtattga       1140
tcgtatcctc cgtgaagctg acgtggcgaa ggcgagcctc tattcccttt tcggatcgaa       1200
ggacgccttg gttattgcat acctggagaa cctcgatcag ctgtggcgtg aagcgtggcg       1260
tgagcgcacc gtcggtatga aggatccgga agataaaatc atcgcgttct ttgatcagtg       1320
cattgaggaa gaaccagaaa aagatttccg cggctcgcac tttcagaatg cggctagtga       1380
gtaccctcgc cccgaaactg atagcgaaaa gggcattgtt gcagcagtgt tagagcaccg       1440
cgagtggtgt cataagactc tgactgattt gctcactgag aagaacggct acccaggcac       1500
cacccaggcg aatcagctgt tggtgttcct tgatggtgga cttgctggat ctcgattggt       1560
ccacaacatc agtcctcttg agacggctcg cgatttggct cggcagttgt tgtcggctcc       1620
acctgcggac tactcaattt agtttcttca ttttccgaag gggtatcttc gttgggggag       1680
gcgtcgataa gccccttctt tttagcttta acctcagcgc gacgctgctt taagcgctgc       1740
atggcggcgc ggttcatttc acgttgcgtt tcgcgcctct tgttcgcgat ttctttgcgg       1800
gcctgttttg cttcgttgat ttcggcagta cgggtttttgg tgagtccac gtttgttgcg       1860 tgaagcgttg aggcgttcca tggggtgaga atcatcaggg cgcggttttt gcgtcgtgtc       1920
cacaggaaga tgcgcttttc tttttgtttt gcgcggtaga tgtcgcgctg ctctaggtgg       1980
tgcactttga aatcgtcggt aagtgggtat ttgcgttcca aaatgaccat catgatgatt       2040
gtttggagga gcgtccacag gttgttgctg acccaataga gtgcgattgc tgtgggggaat      2100 ggtcctgtga ggccaaggga cagtgggaag atcggcgcga ggatcgacat cacgatcatg      2160
aacttcagca tgccgttaga gaatccggat gcgtaatcgt tggtttggaa gctgcggtac      2220
atggacatcg ccatgttgat tgcggtgagg attgcggctg tgatgaacag tggcaaaacg      2280
```

```
aaactaagaa cttccgcctg cgtggtgctc aaatatttta gctgctcagt gggcatcgaa    2340
acataagcgg gcagaggcac attgctcacg cgaccagcga ggaaagattc cacttcctca    2400
ggagttagga agccgatcga ctggaagacg ggattttcca aaccaccttc agggcgagcc    2460
atgcggagaa gtgcccagta aagaccaagg acaatcggta tctggatcag cccaggcaca    2520
caacctgcca gcgggttaat gccgtattcc ttattcaaat cattctggcg cttctgcaac    2580
tcccgaatgg acgcttcatc gtactttccc ttgtattctt cccggagcgc agcgcggtga    2640
gg                                                                   2642

<210> SEQ ID NO 2
<211> LENGTH: 34
<212> TYPE: DNA
<213> ORGANISM: Artificial Sequence
<220> FEATURE:
<223> OTHER INFORMATION: Synthetic primer

<400> SEQUENCE: 2
tcgagctcgg tacccctgcc tggtttgtct tgta                                34

<210> SEQ ID NO 3
<211> LENGTH: 35
<212> TYPE: DNA
<213> ORGANISM: Artificial Sequence
<220> FEATURE:
<223> OTHER INFORMATION: Synthetic primer

<400> SEQUENCE: 3
cggaaaatga agaaagttcg gccacgtcct ttcgg                               35

<210> SEQ ID NO 4
<211> LENGTH: 35
<212> TYPE: DNA
<213> ORGANISM: Artificial Sequence
<220> FEATURE:
<223> OTHER INFORMATION: Synthetic primer

<400> SEQUENCE: 4
aggacgtggc cgaactttct tcattttccg aaggg                               35

<210> SEQ ID NO 5
<211> LENGTH: 35
<212> TYPE: DNA
<213> ORGANISM: Artificial Sequence
<220> FEATURE:
<223> OTHER INFORMATION: Synthetic primer

<400> SEQUENCE: 5
ctctagagga tccccgtttc gatgcccact gagca                               35

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
aatctggatt tccgccaggt                                                20

<210> SEQ ID NO 7
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 7
cttcctaact cctgaggaag                                                                  20

<210> SEQ ID NO 8
<211> LENGTH: 3311
<212> TYPE: DNA
<213> ORGANISM: Corynebacterium glutamicum

<400> SEQUENCE: 8
ctcattccag cgtcacgacg ttccgaaggt actggttacc tggcattggg cactaccgtt         60
tctgcagcac ttggaccagc cctagcactt tttgtcctag gaacatttga ttacgacatg        120
ctgtttatcg tggtcttggc aacctcggtc atctctttga tcgccgtcgt gttcatgtac        180
tttaagacca gcgaccctga gccttctggg gaaccagcca agttcagctt caaatctatt        240
atgaacccaa agatcatccc catcggcatc tttatcttgc ttatttgctt tgcttactct        300
ggcgtcattg cctacatcaa cgcatttgct gaagaacgcg atctgattac gggtgctgga        360
ttgttcttca ttgcctacgc agtatcaatg tttgtgatgc gcagcttcct tggcaaactg        420
caggaccgtc gcggagacaa cgtcgttatt tactttggat tgttcttctt cgttatttcc        480
ttgacgattt tgtcctttgc cacttccaac tggcacgttg tgttgtccgg agtcattgca        540
ggtctgggat acggcacttt gatgccagca gtgcagtcca tcgctgttgg tgtagtagac        600
aaaaccgaat tcggtacggc cttctccact ttgttcctgt ttgtggactt aggttttggc        660
tttggaccta ttatcctggg agcagtttct gcggcaattg gtttcggacc tatgtatgca        720
gcactggcag gtgtgggtgt gattgccgga atcttctacc tgttcacaca cgctcgcacc        780
gatcgagcta agaatggctt tgttaaacac ccagagcctg tcgctttagt tagctagttc        840
tttcagcttt ccctcccgat cagcgtaaac cggcccttcc ggttttgggg tacatcacag        900
aacctgggct agcggtgtag acccgaaaat aaacgagcct tttgtcaggg ttaaggttta        960
ggtatctaag ctaaccaaac accaacaaaa ggctctaccc atgaagtcta ccggcaacat       1020
catcgctgac accatctgcc gcactgcgga actaggactc accatcaccg gcgcttccga       1080
tgcaggtgat tacaccctga tcgaagcaga cgcactcgac tacacctcca cctgcccaga       1140
atgctcccaa cctggggtgt ttcgtcatca cacccaccgg atgctcattg atttacccat       1200
cgtcgggttt cccaccaaac tgtttatccg tctacctcgc taccgctgca ccaaccccac       1260
atgtaagcaa aagtatttcc aagcagaact aagctgcgct gaccacggta aaaaggtcac       1320
ccaccgggtc acccgctgga tttttacaacg ccttgctatt gaccggatga gtgttcacgc       1380
aaccgcgaaa gcacttgggc tagggtggga tttaacctgc caactagccc tcgatatgtg       1440
ccgtgagctg gtctataacg atcctcacca tcttgatgga gtgtatgtca ttggggtgga       1500
tgagcataag tggtcacata ataggctaa gcatggtgat gggtttgtca ccgtgattgt       1560
cgatatgacc gggcatcggt atgactcacg gtgtcctgcc cggttattag atgtcgtccc       1620
aggtcgtagt gctgatgctt tacggtcctg gcttggctcc cgcggtgaac agttccgcaa       1680
tcagatacgg atcgtgtcca tggatggatt ccaaggctac gccacagcaa gtaaagaact       1740
cattccttct gctcgtcgcg tgatggatcc attccatgtt gtgcggcttg ctggtgacaa       1800
gctcaccgcc tgccggcaac gcctccacgc ggagaaatac cagcgtcgtg gtttaagcca       1860
ggatccgttg tataaaaacc ggaagacctt gttgaccacg cacaagtggt tgagtcctcg       1920
```

-continued

```
tcagcaagaa agcttggagc agttgtgggc gtatgacaaa gactacgggg cgttaaagct    1980
tgcgtggctt gcgtatcagg cgattattga ttgttatcag atgggtaata agcgtgaagc    2040
gaagaagaaa atgcggacca ttattgatca gcttcgggtg ttgaaggggc cgaataagga    2100
actcgcgcag ttgggtcgta gtttgtttaa acgacttggt gatgtgttgg cgtatttcga    2160
tgttggtgtc tccaacggtc cggtcgaagc gatcaacgga cggttggagc atttgcgtgg    2220
gattgctcta ggtttccgta atttgaacca ctacattctg cggtgcctta tccattcagg    2280
gcagttggtc cataagatca atgcactcta aaacaggaag agcccgtaaa cctctgacta    2340
gcgtcaccct ctgattaagg cgaccgcgga tttaagagca gaggctgcca cgagcgcatc    2400
ttcacggctg tgtgttgtac taaaagtaca gcgcacagcc gttcgtgctt gatcctcctc    2460
aagccccaac gccagcaaca catgggatac ctctccggaa ccacaggcag aaccagggga    2520
gcacacaatg ccttggcgtt ccaattccag aagaacagtt tcagatccta tgctgtcgaa    2580
gagaaaagat gcgtgtccat caatgcgcat cctaggatgt ccagtcaggt gtgctcccgg    2640
gatagtgaga acttcctcga tgaattcgcc aagatctgga taggattccg ccctggccaa    2700
ttccaaggca gtggcaaagg cgatagcccc cgcaacgttt tccgtgccac tacgccgccc    2760
tttttcctgg ccgccgccat ggattaccgg ctccagggga agctttgacc ataacactcc    2820
aatcccttta ggcgcaccga atttatgacc cgacaaactt aacgcgtcaa ctcccaagtc    2880
aaaggttaaa tgtgcagctt gcactgcatc ggtgtgaaaa ggcgtactgc ttaccgccgc    2940
caactcagct atcggctgaa tggttcccac ctcattgttg gcataaccaa tgctgatcaa    3000
tgtggtgtcc ggcctgactg ctttgcggag accctccggg gagatcagcc cagtgtgatc    3060
gggggatagg taggtgatct cgaaatcatg aaacctttca agataagcag cagtttctag    3120
gacactgtca tgctcgatcg gggtggtgat gaggtgccgg ccacgaggat tagctaagca    3180
cgctcctttg atagcgaggt tgttggcttc tgatccaccc gacgtaaacg tcacctgtgt    3240
ggggcgtcct ccgataatgc gggccacccg agttcgagca tcctccagcc ccgcagaggc    3300
gagtcttccc a                                                        3311
```

```
<210> SEQ ID NO 9
<211> LENGTH: 35
<212> TYPE: DNA
<213> ORGANISM: Artificial Sequence
<220> FEATURE:
<223> OTHER INFORMATION: Synthetic primer

<400> SEQUENCE: 9
acccggggat cctctagaat gtttgtgatg cgcag                                35

<210> SEQ ID NO 10
<211> LENGTH: 35
<212> TYPE: DNA
<213> ORGANISM: Artificial Sequence
<220> FEATURE:
<223> OTHER INFORMATION: Synthetic primer

<400> SEQUENCE: 10
gtcagagagt acttacgctg atcgggaggg aaagc                                35

<210> SEQ ID NO 11
<211> LENGTH: 35
<212> TYPE: DNA
<213> ORGANISM: Artificial Sequence
<220> FEATURE:
```

-continued

<223> OTHER INFORMATION: Synthetic primer

<400> SEQUENCE: 11
atcagcgtaa gtactctctg actagcgtca ccctc                              35

<210> SEQ ID NO 12
<211> LENGTH: 35
<212> TYPE: DNA
<213> ORGANISM: Artificial Sequence
<220> FEATURE:
<223> OTHER INFORMATION: Synthetic primer

<400> SEQUENCE: 12
ctgcaggtcg actctagaaa agggattgga gtgtt                              35

<210> SEQ ID NO 13
<211> LENGTH: 35
<212> TYPE: DNA
<213> ORGANISM: Artificial Sequence
<220> FEATURE:
<223> OTHER INFORMATION: Synthetic primer

<400> SEQUENCE: 13
atcaaaacag atatcatggc atccgacgcg ccgca                              35

<210> SEQ ID NO 14
<211> LENGTH: 35
<212> TYPE: DNA
<213> ORGANISM: Artificial Sequence
<220> FEATURE:
<223> OTHER INFORMATION: Synthetic primer

<400> SEQUENCE: 14
cgctagtcag agagtttagt caaggccccg caaca                              35

<210> SEQ ID NO 15
<211> LENGTH: 35
<212> TYPE: DNA
<213> ORGANISM: Artificial Sequence
<220> FEATURE:
<223> OTHER INFORMATION: Synthetic primer

<400> SEQUENCE: 15
atcaaaacag atatcatggc ggatgcaccc ggcgg                              35

<210> SEQ ID NO 16
<211> LENGTH: 35
<212> TYPE: DNA
<213> ORGANISM: Artificial Sequence
<220> FEATURE:
<223> OTHER INFORMATION: Synthetic primer

<400> SEQUENCE: 16
cgctagtcag agagttcaca agctgttaag cgaag                              35

<210> SEQ ID NO 17
<211> LENGTH: 35
<212> TYPE: DNA
<213> ORGANISM: Artificial Sequence
<220> FEATURE:
<223> OTHER INFORMATION: Synthetic primer

<400> SEQUENCE: 17
atcaaaacag atatcatgac gaaggactgg aagac                              35

-continued

```
<210> SEQ ID NO 18
<211> LENGTH: 35
<212> TYPE: DNA
<213> ORGANISM: Artificial Sequence
<220> FEATURE:
<223> OTHER INFORMATION: Synthetic primer

<400> SEQUENCE: 18
cgctagtcag agagttcaga tcaccgcgag cgcct                    35

<210> SEQ ID NO 19
<211> LENGTH: 35
<212> TYPE: DNA
<213> ORGANISM: Artificial Sequence
<220> FEATURE:
<223> OTHER INFORMATION: Synthetic primer

<400> SEQUENCE: 19
ccgatcagcg taagtggcgc ttcatgtcaa caatc                    35

<210> SEQ ID NO 20
<211> LENGTH: 35
<212> TYPE: DNA
<213> ORGANISM: Artificial Sequence
<220> FEATURE:
<223> OTHER INFORMATION: Synthetic primer

<400> SEQUENCE: 20
cgcgtcggat gccatgatat ctgttttgat ctcct                    35

<210> SEQ ID NO 21
<211> LENGTH: 35
<212> TYPE: DNA
<213> ORGANISM: Artificial Sequence
<220> FEATURE:
<223> OTHER INFORMATION: Synthetic primer

<400> SEQUENCE: 21
gggtgcatcc gccatgatat ctgttttgat ctcct                    35

<210> SEQ ID NO 22
<211> LENGTH: 35
<212> TYPE: DNA
<213> ORGANISM: Artificial Sequence
<220> FEATURE:
<223> OTHER INFORMATION: Synthetic primer

<400> SEQUENCE: 22
ccagtccttc gtcatgatat ctgttttgat ctcct                    35

<210> SEQ ID NO 23
<211> LENGTH: 18
<212> TYPE: DNA
<213> ORGANISM: Artificial Sequence
<220> FEATURE:
<223> OTHER INFORMATION: Synthetic primer

<400> SEQUENCE: 23
aatggtccag gagctcat                                       18

<210> SEQ ID NO 24
<211> LENGTH: 18
<212> TYPE: DNA
<213> ORGANISM: Artificial Sequence
<220> FEATURE:
<223> OTHER INFORMATION: Synthetic primer
```

-continued

<400> SEQUENCE: 24
gatcacctac ctatcccc                                                        18

<210> SEQ ID NO 25
<211> LENGTH: 3161
<212> TYPE: DNA
<213> ORGANISM: Corynebacterium glutamicum

<400> SEQUENCE: 25
cggtggacga tgagggaaaa cgtttcctcg ccgcccacag aatcataaaa attttctgag        60
gttgtcatgg gtaccagtct aagccctggc cttacgccag taaggtgtta cccatgcgcg       120
aactagcact caacatggcc ggcgtcaccg tgcggcgcgg cgagaaattg cttctcgacg       180
atatctccct ctcaattccg caagggtcgc actgggccgt acttggtcca aatggcgccg       240
gtaaaaccac catgctgaag atcgcagcca ccttgctgta cccatcggaa ggcaccgtgg       300
acatcctggg gcatcgcttt ggtcgggtgg atactcgtga gctgcggaaa acaatcggcc       360
tggtggaccc gaagcaaaga tttaccaacc tgccggccca cgaaattgtg ctgtcggggt       420
taaccgcctc caacgggttg ttgccacggt ggtcggcttc ggcttcggag ttggagcggt       480
gcgctttgat gttggagttg gtgggcatga cagcgcgtgc cgatcgttac tgggccgata       540
tgagccaggg cgaaaaagcc cgcaccctga ttgctcgtgc gctgattatc tcaccgaccc       600
tactgctgct tgatgaaccc accaccggcc ttgacctgcc cggacgtgaa actttgctca       660
gtgtgattga tggtttgcga gccgctcttc ctggtctgac gacagtgatg atcacccacc       720
acgtcgaaga gatcgccgcc tccacgacag atatcctcat gatcaaggac gcccgcatac       780
tggcttcggg gactgtttca gaagtgatga ctcctgaaaa tttgggcgcg ctgtatgaca       840
tgtcggtgtc gttggaaact gtgcgcagcc ggtggttcgc gttcgatgct ctgcattaaa       900
aggggctagt tttacacaaa agtggacagc ttggtctatc attgccagaa gaccggtcct       960
tttaggccca tagaattctg attacaggag ttgatctacc ttgtcttttg acccaaacac      1020
ccagggtttc tccactgcat cgattcacgc tgggtatgag ccagacgact actacggttc      1080
gattaacacc ccaatctatg cctccaccac cttcgcgcag aacgctccaa acgaactgcg      1140
caaaggctac gagtacaccc gtgtgggcaa ccccaccatc gtggcattag agcagaccgt      1200
cgcagcactc gaaggcgcaa agtatggccg cgcattctcc tccggcatgg ctgcaaccga      1260
catcctgttc cgcatcatcc tcaagccggg cgatcacatc gtcctcggca acgatgctta      1320
cggcggaacc taccgcctga tcgacaccgt attcaccgca tggggcgtcg aatacaccgt      1380
tgttgatacc tccgtcgtgg aagaggtcaa ggcagcgatc aaggacaaca ccaagctgat      1440
ctgggtggaa accccaacca acccagcact tggcatcacc gacatcgaag cagtagcaaa      1500
gctcaccgaa ggcaccaacg ccaagctggt tgttgacaac accttcgcat ccccatacct      1560
gcagcagcca ctaaaactcg gcgcacacgc agtcctgcac tccaccacca gtacatcgg       1620 aggacactcc gacgttgttg gcggccttgt ggttaccaac gaccaggaaa tggacgaaga      1680
actgctgttc atgcagggcg gcatcggacc gatcccatca gttttcgatg catacctgac      1740
cgcccgtggc ctcaagaccc ttgcagtgcg catggatcgc cactgcgaca cgcagaaaa       1800 gatcgcggaa ttcctggact cccgcccaga ggtctccacc gtgctctacc caggtctgaa      1860
gaaccaccca ggccacgaag tcgcagcgaa gcagatgaag cgcttcggcg gcatgatctc      1920
cgtccgtttc gcaggcggcg aagaagcagc taagaagttc tgtacctcca ccaaactgat      1980
ctgtctggcc gagtccctcg gtggcgtgga atccctcctg gagcacccag caaccatgac      2040

```
ccaccagtca gctgccggct ctcagctcga ggttccccgc gacctcgtgc gcatctccat    2100
tggtattgaa gacattgaag acctgctcgc agatgtcgag caggccctca ataacctta     2160 gaaactattt ggcggcaagc agcttttcaa tataagcaat gcgagcctcc accatgtagc    2220
cgaagagttc gtcagaagtt gagacggact cttcgactgc tttacgggtc agtggcgctt    2280
ccacatctgg gttctcatca agccatggct taggaaccgg agcaaacaca tccggctttt    2340
cgccctctgg acgattgtca aaggtgtagt cagaagtcag ggtgaagctg aagacatcag    2400
ccatcatcat ctcccggatg atggttgctt ccttgaggga cagcccgata tcagtcaaga    2460
acttcaagga ctcctccgca cccgcgattc gcagtgggga agtgccctga gtagagatct    2520
gttcatccag cgcgaccaga agaacacgtg gagtctcacg gaattggtcg cgcaatgagc    2580
tccacagcgt atgaatagat tgccgccaat tgtccggatc aagatcgggc accttgatat    2640
catcgatgat gcgcacccag acgcgatcaa tgatttcttg acgatttagc acatggttat    2700
acagtgcgcg aggggtgaca cccatgtctc gggcgaggcg gttcatggtc acggcagcga    2760
atccttcgcg gccggcaatg tttaaagtgc gctccactat ggattcgacg gaaaggatac    2820
gttgggtggg gcgtccagga cgacgtcccg tggaagtggc cgccagagtt gacgctacgg    2880
ctggtttcat agtttcgcta ggcatgttat atgacgttac gccttttct acaagacaac     2940 cagcgttttc agcgagatac tggacatatc aactaaaatc cctgaataaa acatctaaca    3000 tgggtttttat acagaaaatt catacgaaag gttgatcatg aagaagaaga ttgcggtcgt    3060
taccggagcg accggaggca tgggaattga gatcgtcaaa gacctctccc gcgaccacat    3120
tgtctacgcc ttgggccgaa atccagagca tctggcagct c                       3161
```

```
<210> SEQ ID NO 26
<211> LENGTH: 3314
<212> TYPE: DNA
<213> ORGANISM: Corynebacterium glutamicum

<400> SEQUENCE: 26
```

```
gataccggca gctccaccga ccgtgcccat ttcatcacga accatctggc caagtgagcg      60
tccacgccta cgagtagaca cccacagcac taggtagtcc tgcactgcac cggcgaaaat     120
cacaccgagg ataatccaca aggtgcctgg caggtagccc atctgcgcgg ccatgacagg     180
tccaaccaat ggaccggcac ctgcaatagc tgcaaagtgg tggccaaaaa gcacgacgcg     240
atccgttggg acatagtcct tgccgtcatt aacgtattcc gccggggttg ctcgctgatc     300
tttcggctta caactttgt attcaatcag tcgggcatag aaagaaaacg caatgatata      360
ggaaccaact gccgccaaaa ccagccacac agagttgatt gtttcgccac gggagaaagc     420
gattgctccc caacccaccg ccgcgataac cccaaagaca aggagaccaa cgcgggcggt     480
cggtgacatt ttaggggact tcttcacgcc tactggaagg tcagtagcgt tgctgtacac     540
caaatcatcg tcattgatgt tgtcagtctg ttttatggtc acgatcttta ctgttttctc     600
ttcgggtcgt ttcaaagcca ctatgcgtag aaacagcggg cagaaactgt gtgcagaaat     660
gcatgcagaa aaaggaaagt tcggccagat gggtgtttct gtatgccgat gatcggatct     720
ttgacagctg ggtatgcgac aaatcaccga gagttgttaa ttcttaacaa tggaaaagta     780
acattgagag atgatttata ccatcctgca ccatttagag tggggctagt cataccccca     840
taaccctagc tgtacgcaat cgatttcaaa tcagttggaa aaagtcaaga aaattacccg     900
agaataaatt tataccacac agtctattgc aatagaccaa gctgttcagt agggtgcatg     960
```

-continued

```
ggagaagaat ttcctaataa aaactcttaa ggacctccaa atgccaaagt acgacaattc     1020
caatgctgac cagtggggct ttgaaacccg ctccattcac gcaggccagt cagtagacgc     1080
acagaccagc gcacgaaacc ttccgatcta ccaatccacc gctttcgtgt tcgactccgc     1140
tgagcacgcc aagcagcgtt tcgcacttga ggatctaggc cctgtttact cccgcctcac     1200
caacccaacc gttgaggctt tggaaaaccg catcgcttcc ctcgaaggtg gcgtccacgc     1260
tgtagcgttc tcctccggac aggccgcaac caccaacgcc attttgaacc tggcaggagc     1320
gggcgaccac atcgtcacct ccccacgcct ctacggtggc accgagactc tattccttat     1380
cactcttaac cgcctgggta tcgatgtttc cttcgtggaa aaccccgacg accctgagtc     1440
ctggcaggca gccgttcagc caaacaccaa agcattcttc ggcgagactt tcgccaaccc     1500
acaggcagac gtcctggata ttcctgcggt ggctgaagtt gcgcaccgca acagcgttcc     1560
actgatcatc gacaacacca tcgctaccgc agcgctcgtg cgcccgctcg agctcggcgc     1620
agacgttgtc gtcgcttccc tcaccaagtt ctacaccggc aacggctccg gactgggcgg     1680
cgtgcttatc gacggcggaa agttcgattg gactgtcgaa aaggatggaa agccagtatt     1740
cccctacttc gtcactccag atgctgctta ccacggattg aagtacgcag accttggtgc     1800
accagccttc ggcctcaagg ttcgcgttgg ccttctacgc gacaccggct ccaccctctc     1860
cgcattcaac gcatgggctg cagtccaggg catcgacacc cttttccctgc gcctggagcg     1920 ccacaacgaa aacgccatca aggttgcaga attcctcaac aaccacgaga aggtggaaaa     1980
ggttaacttc gcaggcctga aggattcccc ttggtacgca accaaggaaa agcttggcct     2040
gaagtacacc ggctccgttc tcaccttcga gatcaagggc ggcaaggatg aggcttgggc     2100
atttatcgac gccctgaagc tacactccaa ccttgcaaac atcggcgatg ttcgctccct     2160
cgttgttcac ccagcaacca ccacccattc acagtccgac gaagctggcc tggcacgcgc     2220
gggcgttacc cagtccaccg tccgcctgtc cgttggcatc gagaccattg atgatatcat     2280
cgctgacctc gaaggcggct ttgctgcaat ctagctttaa atagactcac cccagtgctt     2340
aaagcgctgg gttttctttt ttcagactcg tgagaatgca aactagacta gacagagctg     2400
tccatataca ctggacgaag ttttagtctt gtccacccag aacaggcggt tattttcatg     2460 cccacccteg cgccttcagg tcaacttgaa atccaagcga tcggtgatgt ctccaccgaa     2520
gccggagcaa tcattacaaa cgctgaaatc gcctatcacc gctggggtga ataccgcgta     2580
gataaagaag gacgcagcaa tgtcgttctc atcgaacacg ccctcactgg agattccaac     2640
gcagccgatt ggtgggctga cttgctcggt cccggcaaag ccatcaacac tgatatttac     2700
tgcgtgatct gtaccaacgt catcggtggt tgcaacggtt ccaccggacc tggctccatg     2760
catccagatg gaaatttctg gggtaatcgc ttccccgcca cgtccattcg tgatcaggta     2820
aacgccgaaa aacaattcct cgacgcactc ggcatcacca cggtcgccgc agtacttggt     2880
ggttccatgg gtggtgcccg cacccctagag tgggccgcaa tgtacccaga aactgttggc     2940
gcagctgctg ttcttgcagt ttctgcacgc gccagcgcct ggcaaatcgg cattcaatcc     3000
gcccaaatta aggcgattga aaacgaccac cactggcacg aaggcaacta ctacgaatcc     3060
ggctgcaacc cagccaccgg actcggcgcc gcccgacgca tcgcccacct cacctaccgt     3120
ggcgaactag aaatcgacga acgcttcggc accaaagccc aaaagaacga aaacccactc     3180
ggtccctacc gcaagcccga ccagcgcttc gccgtggaat cctacttgga ctaccaagca     3240
gacaagctag tacagcgttt cgacgccggc tcctacgtct tgctcaccga cgccctcaac     3300
cgccacgaca ttgg                                                        3314
```

-continued

```
<210> SEQ ID NO 27
<211> LENGTH: 43
<212> TYPE: DNA
<213> ORGANISM: Artificial Sequence
<220> FEATURE:
<223> OTHER INFORMATION: Synthetic primer

<400> SEQUENCE: 27
gaattcgagc tcggtacccg ggccagtaag gtgttaccca tgc                    43

<210> SEQ ID NO 28
<211> LENGTH: 57
<212> TYPE: DNA
<213> ORGANISM: Artificial Sequence
<220> FEATURE:
<223> OTHER INFORMATION: Synthetic primer

<400> SEQUENCE: 28
ctgcttgccg ccaaatagtt tagtactggt agatcaactc ctgtaatcag aattcta     57

<210> SEQ ID NO 29
<211> LENGTH: 57
<212> TYPE: DNA
<213> ORGANISM: Artificial Sequence
<220> FEATURE:
<223> OTHER INFORMATION: Synthetic primer

<400> SEQUENCE: 29
tagaattctg attacaggag ttgatctacc agtactaaac tatttggcgg caagcag     57

<210> SEQ ID NO 30
<211> LENGTH: 43
<212> TYPE: DNA
<213> ORGANISM: Artificial Sequence
<220> FEATURE:
<223> OTHER INFORMATION: Synthetic primer

<400> SEQUENCE: 30
tcgactctag aggatccccg ggcgatctca attcccatgc ctc                    43

<210> SEQ ID NO 31
<211> LENGTH: 35
<212> TYPE: DNA
<213> ORGANISM: Artificial Sequence
<220> FEATURE:
<223> OTHER INFORMATION: Synthetic primer

<400> SEQUENCE: 31
tcgagctcgg tacccctgca atagctgcaa agtgg                             35

<210> SEQ ID NO 32
<211> LENGTH: 35
<212> TYPE: DNA
<213> ORGANISM: Artificial Sequence
<220> FEATURE:
<223> OTHER INFORMATION: Synthetic primer

<400> SEQUENCE: 32
tgagtctatt taaagcgggt aattttcttg acttt                             35

<210> SEQ ID NO 33
<211> LENGTH: 35
<212> TYPE: DNA
<213> ORGANISM: Artificial Sequence
<220> FEATURE:
```

-continued

<223> OTHER INFORMATION: Synthetic primer

<400> SEQUENCE: 33
caagaaaatt acccgcttta aatagactca cccca                                          35

<210> SEQ ID NO 34
<211> LENGTH: 35
<212> TYPE: DNA
<213> ORGANISM: Artificial Sequence
<220> FEATURE:
<223> OTHER INFORMATION: Synthetic primer

<400> SEQUENCE: 34
ctctagagga tccccgcctt aatttgggcg gattg                                          35

<210> SEQ ID NO 35
<211> LENGTH: 20
<212> TYPE: DNA
<213> ORGANISM: Artificial Sequence
<220> FEATURE:
<223> OTHER INFORMATION: Synthetic primer

<400> SEQUENCE: 35
ttcctggtct gacgacagtg                                                           20

<210> SEQ ID NO 36
<211> LENGTH: 21
<212> TYPE: DNA
<213> ORGANISM: Artificial Sequence
<220> FEATURE:
<223> OTHER INFORMATION: Synthetic primer

<400> SEQUENCE: 36
gatgtcttca gcttcaccct g                                                         21

<210> SEQ ID NO 37
<211> LENGTH: 20
<212> TYPE: DNA
<213> ORGANISM: Artificial Sequence
<220> FEATURE:
<223> OTHER INFORMATION: Synthetic primer

<400> SEQUENCE: 37
ccgaggataa tccacaaggt                                                           20

<210> SEQ ID NO 38
<211> LENGTH: 20
<212> TYPE: DNA
<213> ORGANISM: Artificial Sequence
<220> FEATURE:
<223> OTHER INFORMATION: Synthetic primer

<400> SEQUENCE: 38
cgaagcgttc gtcgatttct                                                           20

<210> SEQ ID NO 39
<211> LENGTH: 5666
<212> TYPE: DNA
<213> ORGANISM: Corynebacterium glutamicum

<400> SEQUENCE: 39
tgtcatgctt ccggaggtgc gcagggctcg agactccgga aagctatttg ccactccgat        60
gtttgggtca ctcgacgaga tacgtgctga tcacctaatt tggtgcacag ggtttcggcc       120
ggcgattagg ccagttcgtc aacttctcaa acacggacaa ccaaaggttc ctggtcttta       180

```
tttagtaggc tacggagatt ggacgggacc tgggtctgcg actatcacag gggtcgggct      240
ttatgccaag cgagcagcca aagagattgc cgcgtcagtc ggcaaagtcg ttaaatagtt      300
tgaaggctaa gaacttaatg ttaaagcgaa aattgttttg acacctcaac taatgcagcg      360
atgcgttctt tccagaatgc tttcatgaca gggatgctgt cttgatcagg caggcgtctg      420
tgctggatgc cgaagctgga tttattgtcg cctttggagg tgaagttgac gctcactcga      480
gaatcatcgg ccaaccattt ggcattgaat gttctaggtt cggaggcgga ggttttctca      540
attagtgcgg gatcgagcca ctgcgcccgc aggtcatcgt ctccgaagag cttccacact      600
ttttcgaccg gcaggttaag ggttttggag gcattggccg cgaacccatc gctggtcatc      660
ccgggtttgc gcatgccacg ttcgtattca taaccaatcg cgatgccttg agcccaccag      720
ccactgacat caaagttgtc cacgatgtgc tttgcgatgt gggtgtgagt ccaagaggtg      780
gcttttacgt cgtcaagcaa ttttagccac tcttcccacg gctttccggt gccgttgagg      840
atagcttcag gggacatgcc tggtgttgag ccttgcggag tggagtcagt catgcgaccg      900
agactagtgg cgctttgcct gtgttgctta ggcggcgttg aaaatgaact acgaatgaaa      960
agttcgggaa ttgtctaatc cgtactaagc tgtctacaca atgtctactt cagttacttc     1020
accagcccac aacaacgcac attcctccga atttttggat gcgttggcaa accatgtgtt     1080
gatcggcgac ggcgccatgg gcacccagct ccaaggcttt gacctggacg tggaaaagga     1140
tttccttgat ctggaggggt gtaatgagat tctcaacgac acccgccctg atgtgttgag     1200
gcagattcac cgcgcctact ttgaggcggg agctgacttg gttgagacca atacttttgg     1260
ttgcaacctg ccgaacttgg cggattatga catcgctgat cgttgccgtg agcttgccta     1320
caagggcact gcagtggcta gggaagtggc tgatgagatg gggccgggcc gaaacggcat     1380
gcggcgtttc gtggttggtt ccctgggacc tggaacgaag cttccatcgc tgggccatgc     1440
accgtatgca gatttgcgtg ggcactacaa ggaagcagcg cttggcatca tcgacggtgg     1500
tggcgatgcc tttttgattg agactgctca ggacttgctt caggtcaagg ctgcggttca     1560
cggcgttcaa gatgccatgg ctgaacttga tacattcttg cccattattt gccacgtcac     1620
cgtagagacc accggcacca tgctcatggg ttctgagatc ggtgccgcgt tgacagcgct     1680
gcagccactg ggtatcgaca tgattggtct gaactgcgcc accggcccag atgagatgag     1740
cgagcacctg cgttacctgt ccaagcacgc cgatattcct gtgtcggtga tgcctaacgc     1800
aggtcttcct gtcctgggta aaaacggtgc agaataccca cttgaggctg aggatttggc     1860
gcaggcgctg gctggattcg tctccgaata tggcctgtcc atggtgggtg ttgttgtgg      1920 caccacacct gagcacatcc gtgcggtccg cgatgcggtg gttggtgttc cagagcagga     1980
aacctccaca ctgaccaaga tccctgcagg ccctgttgag caggcctccc gcgaggtgga     2040
gaaagaggac tccgtcgcgt cgctgtacac ctcggtgcca ttgtcccagg aaaccggcat     2100
ttccatgatc ggtgagcgca ccaactccaa cggttccaag gcattccgtg aggcaatgct     2160
gtctggcgat tgggaaaagt gtgtggatat tgccaagcag caaacccgcg atggtgcaca     2220
catgctggat ctttgtgtgg attacgtggg acgagacggc accgccgata tggcgacctt     2280
ggcagcactt cttgctacca gctccacttt gccaatcatg attgactcca ccgagccaga     2340
ggttattcgc acaggccttg agcacttggg tggacgaagc atcgttaact ccgtcaactt     2400
tgaagacggc gatggccctg agtcccgcta ccagcgcatc atgaaactgg taaagcagca     2460
cggtgcggcc gtggttgcgc tgaccattga tgaggaaggc caggcacgta ccgctgagca     2520
```

-continued

```
caaggtgcgc attgctaaac gactgattga cgatatcacc ggcagctacg gcctggatat   2580
caaagacatc gttgtggact gcctgacctt cccgatctct actggccagg aagaaaccag   2640
gcgagatggc attgaaacca tcgaagccat ccgcgagctg aagaagctct acccagaaat   2700
ccacaccacc ctgggtctgt ccaatatttc cttcggcctg aaccctgctg cacgccaggt   2760
tcttaactct gtgttcctca atgagtgcat tgaggctggt ctggactctg cgattgcgca   2820
cagctccaag attttgccga tgaaccgcat tgatgatcgc cagcgcgaag tggcgttgga   2880
tatggtctat gatcgccgca ccgaggatta cgatccgctg caggaattca tgcagctgtt   2940
tgagggcgtt tctgctgccg atgccaagga tgctcgcgct gaacagctgg ccgctatgcc   3000
tttgtttgag cgtttggcac agcgcatcat cgacggcgat aagaatggcc ttgaggatga   3060
tctggaagca ggcatgaagg agaagtctcc tattgcgatc atcaacgagg accttctcaa   3120
cggcatgaag accgtgggtg agctgtttgg ttccggacag atgcagctgc cattcgtgct   3180
gcaatcggca gaaaccatga aaactgcggt ggcctatttg gaaccgttca tggaagagga   3240
agcagaagct accggatctg cgcaggcaga gggcaagggc aaaatcgtcg tggccaccgt   3300
caagggtgac gtgcacgata tcggcaagaa cttggtggac atcatttttgt ccaacaacgg   3360 ttacgacgtg gtgaacttgg gcatcaagca gccactgtcc gccatgttgg aagcagcgga   3420
agaacacaaa gcagacgtca tcggcatgtc gggacttctt gtgaagtcca ccgtggtgat   3480
gaaggaaaac cttgaggaga tgaacaacgc cggcgcatcc aattacccag tcattttggg   3540
tggcgctgcg ctgacgcgta cctacgtgga aaacgatctc aacgaggtgt acaccggtga   3600
ggtgtactac gcccgtgatg ctttcgaggg cctgcgcctg atggatgagg tgatggcaga   3660
aaagcgtggt gaaggacttg atcccaactc accagaagct attgagcagg cgaagaagaa   3720
ggcggaacgt aaggctcgta atgagcgttc ccgcaagatt gccgcggagc gtaaagctaa   3780
tgcggctccc gtgattgttc cggagcgttc tgatgtctcc accgatactc caaccgcggc   3840
accaccgttc tggggaaccc gcattgtcaa gggtctgccc ttggcggagt cttgggcaa    3900 ccttgatgag cgcgccttgt tcatggggca gtggggtctg aaatccaccc gcggcaacga   3960
gggtccaagc tatgaggatt tggtggaaac tgaaggccga ccacgcctgc gctactggct   4020
ggatcgcctg aagtctgagg gcattttgga ccacgtggcc ttggtgtatg ctacttccc    4080 agcggtcgcg gaaggcgatg acgtggtgat cttggaatcc ccggatccac acgcagccga   4140
acgcatgcgc tttagcttcc cacgccagca gcgcggcagg ttcttgtgca tcgcggattt   4200
cattcgccca cgcgagcaag ctgtcaagga cggccaagtg gacgtcatgc cattccagct   4260
ggtcaccatg ggtaatccta ttgctgattt cgccaacgag ttgttcgcag ccaatgaata   4320
ccgcgagtac ttggaagttc acggcatcgg cgtgcagctc accgaagcat ggccgagta    4380 ctggcactcc cgagtgcgca gcgaactcaa gctgaacgac ggtggatctg tcgctgattt   4440
tgatccagaa gacaagacca agttcttcga cctggattac cgcggcgccc gcttctcctt   4500
tggttacggt tcttgccctg atctggaaga ccgcgcaaag ctggtggaat tgctcgagcc   4560
aggccgtatc ggcgtggagt tgtccgagga actccagctg cacccagagc agtccacaga   4620
cgcgtttgtg ctctaccacc cagaggcaaa gtactttaac gtctaacacc tttgagaggg   4680
aaaactttcc cgcacattgc agatcgtgcc actttaacta aggttgacgg catgattaag   4740 gcgatttttct gggacatgga cggcacgatg gtggactctg agccacagtg gggcattgct   4800
acctacgagc tcagcgaagc catgggccgc cgcctcaccc cggagctccg ggaactcacc   4860
gtcggctcga gcctgccgcg caccatgcgc ttatgcgcag agcacgcagg cattacattg   4920
```

```
agcgacgcgg actacgagcg ctaccgggct ggcatgttcg cccgggtcca tgagctttc     4980 gacgaatccc tcgtcccaaa tccaggcgtc accgaactcc tgacagagtt gaaggccctc     5040
gagatcccca tgttggtcac caccaacaca gagcgcgatc tcgcgacccg ttcagtcgca     5100
gccgtgggaa atgagttctt catcggttct atcgctggtg atgaagtccc aacagcaaag     5160 ccagccccg acatgtacct cgaagcagca cgacgtgtgg ctttgaccc atcagagtgc      5220 ctcgtgttcg aagattccta caacggcatg ctgggcgctg ttactgcagg ttgccgcgtc     5280
attggtctgc acccagaaga agtccaagcg ccagaaggtg tagtgccttt gcgttccctc     5340
cacggtaaaa actctttcga aggtgtcacc gctgagatgg tcactgcctg gtaccaccag     5400
atcgagccgg caggtgtcgc aaaataaaac caggtggggg agtgaaatta ttcgactaat     5460
atcctccccc aaacacacat tgataactgt tgtgtggaag aatgtaccga gtgaagacat     5520
ttgactcgct gtacgaagaa cttcttaacc gtgctcagac ccgccctgaa gggtctggaa     5580
ccgtggccgc cttggataaa ggcatccatc atctaggtaa gaaggtcatc gaagaagccg     5640
gagaggtctg gattgcagcc gagtat                                          5666
```

```
<210> SEQ ID NO 40
<211> LENGTH: 3613
<212> TYPE: DNA
<213> ORGANISM: Corynebacterium glutamicum

<400> SEQUENCE: 40
tcctgtgggg tgaacttgac ctgtgctggg ccacgacgtc cgaaaacgtg cacttcagtg      60
gccttgtttt ctttgaggga gtcgtagacg ttgtcggaaa tttcggtgac tttgagctcg     120
tcgcctgtct tagccaggat gcgggctacg tcgaggccga cgttaccaac gccgataaca     180
gcgacggact gtgcagacag atcccaggag cgctcgaagc gtgggttgcc gtcgtagaag     240
ccaacgaact cgccggcacc gaaggagcct tctgcttcaa ttccggggat gttgaggtcg     300
cggtctgcaa ctgcgccggt ggagaacacg actgcatcgt agtagtcgcg gagttcttcg     360
acggtgatgt ctttgccgat ttcaatgtta ccgagcaggc gcaggcgtgg cttgtccaac     420
acgttgtgca gggacttaac gatgcccttg atgcgtgggt ggtctggagc aacgccgtaa     480
cggatgagtc cgaacggtgc aggcatttgc tcgaaaaggt caacgaacac ttcgcgctct     540
tcattgcgga tgaggaggtc ggatgcgtaa atgccagcag ggccagctcc gatgacggct     600
acgcgcaggg gagttgtcat gtgtttgaag ttgcctttcg tgagcccttt tatggaaaca     660
agggtgtgaa aatcaagtag ttaaaggtgt ttcaagtcca ggctgtttaa cactcctaga     720
ccgcttggtc tgtaaacgta gcagcgaaat gcgacaatgc gaagactttt gcttaattaa     780
attcaaactc catgaaaaaa ctagacagat cggtctatta tattcacggt gaacctaacc     840
taatatcccc aggttaattc atttaaacgg gcattaggtg actccattgc tttcagtctc     900
atgaatctaa tggttggtct agacagacg gtacgtctaa gtttgcggat agatcaaacc      960
gagtgacatg tacttcacta gctctttaag gattaactcc ccatgacaac aaccaccgga     1020
agtgcccggc cagcacgtgc cgccaggaag cctaagcccg aaggccaatg gaaaatcgac     1080
ggcaccgagc cgcttaacca tgccgaggaa attaagcaag aagaacccgc ttttgctgtc     1140
aagcagcggg tcattgatat ttactccaag cagggttttt cttccattgc accggatgac     1200
attgccccac gctttaagtg gttgggcatt tacacccagc gtaagcagga tctgggcggt     1260
gaactgaccg gtcagcttcc tgatgatgag ctgcaggatg agtacttcat gatgcgtgtg     1320
```

-continued

```
cgttttgatg gcggactggc ttcccctgag cgcctgcgtg ccgtgggtga aatttctagg    1380
gattatgctc gttccaccgc ggacttcacc gaccgccaga acattcagct gcactggatt    1440
cgtattgaag atgtgcctgc gatctgggag aagctagaaa ccgtcggact gtccaccatg    1500
cttggttgcg gtgacgttcc acgtgttatc ttgggctccc cagtttctgg cgtagctgct    1560
gaagagctga tcgatgccac cccggctatc gatgcgattc gtgagcgcta cctagacaag    1620
gaagagttcc acaaccttcc tcgtaagttt aagactgcta tcactggcaa ccagcgccag    1680
gatgttaccc acgaaatcca ggacgtttcc ttcgttcctt cgattcaccc agaattcggc    1740
ccaggatttg agtgctttgt gggcggtggc ctgtccacca acccaatgct tgctcagcca    1800
cttggttctt ggattccact tgatgaggtt ccagaagtgt gggctggcgt cgccggaatt    1860
ttccgcgact acggcttccg acgcctgcgt aaccgtgctc gcctcaagtt cttggtggca    1920
cagtggggta ttgagaagtt ccgtgaagtt cttgagaccg aatacctcga gcgcaagctg    1980
atcgatggcc cagttgttac caccaaccct ggctaccgtg accacattgg cattcaccca    2040
caaaaggacg gcaagttcta cctcggtgtg aagccaacct tggacacac caccggtgag    2100 cagctcattg ccattgctga tgttgcagaa aagcacggca tcaccaggat tcgtaccacg    2160
gcggaaaagg aactgctctt cctcgatatt gagagaaaga accttactac cgttgcacgc    2220
gacctggatg aaatcggact gtactcttca ccttccgagt tccgccgcgg catcatttcc    2280
tgcaccggct tggagttctg caagcttgcg cacgcaacca ccaagtcacg agcaattgag    2340
cttgtcgacg aactggaaga gcgcctcggc gatttggatg ttcccatcaa gattgcactg    2400
aacggttgcc ctaactcttg tgcacgcacc caggtttccg catcggatt caagggacag    2460 accgtcactg atgctgacgg caaccgcgtt gaaggttcc aggttcacct gggcggttcc    2520
atgaacttgg atccaaactt cggacgcaag ctcaagggcc acaaggttat tgccgatgaa    2580
gtgggagagt acgtcactcg cgttgttacc cacttcaagg aacagcgcca cgaggacgag    2640
cacttccgcg attgggtcca gcgggccgct gaggaagatt tggtgtgagt cttcggagga    2700
aacccaatcc caaccgcaac caccctctgt actgcccata ctgcgcggga gaagttcttt    2760
tccccgatga gcaaacagaa ttcgcgtggt tgtgtgcgga ttgcaccaga gtttttgaag    2820
tgaaatatca cggccaggac gatccagtgc acaggccagc accagcaaag tccacatcgc    2880
aagcattaaa agaatctctc gaaagacaca aaagaggtga gtcgcaacaa tgagctttca    2940
actagttaac gccctgaaaa atactggttc ggtaaaagat cccgagatct caccccgaagg    3000 acctcgcacg accacaccgt tgtcaccaga ggtagcaaaa cataacgagg aactcgtcga    3060
aaagcatgct gctgcgttgt atgacgccag cgcgcaagag atcctggaat ggacagccga    3120
gcacgcgccg ggcgctattg cagtgacctt gagcatggaa aacaccgtgc tggcggagct    3180
ggctgcgcgg cacctgccgg aagctgattt cctcttttg gacaccggtt accacttcaa    3240
ggagaccctt gaagttgccc gtcaggtaga tgagcgctat tcccagaagc ttgtcaccgc    3300
gctgccgatc ctcaagcgca cggagcagga ttccattttat ggtctcaacc tgtaccgcag    3360
caacccagcg gcgtgctgcc gaatgcgcaa agttgaaccg ctggcggcgt cgttaagccc    3420
atacgctggc tggatcaccg gcctgcgccg cgctgatggc ccaacccgtg ctcaagcccc    3480
tgcgctgagc ttggatgcca ccggcaggct caagatttct ccaattatca cctggtcatt    3540
ggaggaaacc aacgagttca ttgcggacaa caacctcatc gatcacccac ttacccatca    3600
gggttatcca tca                                                      3613
```

<210> SEQ ID NO 41
<211> LENGTH: 35
<212> TYPE: DNA
<213> ORGANISM: Artificial Sequence
<220> FEATURE:
<223> OTHER INFORMATION: Synthetic primer

<400> SEQUENCE: 41
caacgaaagg aaacaatgtc tacttcagtt acttc                               35

<210> SEQ ID NO 42
<211> LENGTH: 35
<212> TYPE: DNA
<213> ORGANISM: Artificial Sequence
<220> FEATURE:
<223> OTHER INFORMATION: Synthetic primer

<400> SEQUENCE: 42
tagtcagaga gtgatttaga cgttaaagta ctttg                               35

<210> SEQ ID NO 43
<211> LENGTH: 35
<212> TYPE: DNA
<213> ORGANISM: Artificial Sequence
<220> FEATURE:
<223> OTHER INFORMATION: Synthetic primer

<400> SEQUENCE: 43
atcaaaacag atatcatgac aacaaccacc ggaag                               35

<210> SEQ ID NO 44
<211> LENGTH: 35
<212> TYPE: DNA
<213> ORGANISM: Artificial Sequence
<220> FEATURE:
<223> OTHER INFORMATION: Synthetic primer

<400> SEQUENCE: 44
cgctagtcag agagttcaca ccaaatcttc ctcag                               35

<210> SEQ ID NO 45
<211> LENGTH: 35
<212> TYPE: DNA
<213> ORGANISM: Artificial Sequence
<220> FEATURE:
<223> OTHER INFORMATION: Synthetic primer

<400> SEQUENCE: 45
ccgatcagcg taagtagaaa catcccagcg ctact                               35

<210> SEQ ID NO 46
<211> LENGTH: 35
<212> TYPE: DNA
<213> ORGANISM: Artificial Sequence
<220> FEATURE:
<223> OTHER INFORMATION: Synthetic primer

<400> SEQUENCE: 46
aactgaagta gacattgttt cctttcgttg ggtac                               35

<210> SEQ ID NO 47
<211> LENGTH: 35
<212> TYPE: DNA
<213> ORGANISM: Artificial Sequence
<220> FEATURE:
<223> OTHER INFORMATION: Synthetic primer

```
<400> SEQUENCE: 47
tactttaacg tctaaggtac cggcgcttca tgtca                                    35

<210> SEQ ID NO 48
<211> LENGTH: 35
<212> TYPE: DNA
<213> ORGANISM: Artificial Sequence
<220> FEATURE:
<223> OTHER INFORMATION: Synthetic primer

<400> SEQUENCE: 48
ggtggttgtt gtcatgatat ctgttttgat ctcct                                    35

<210> SEQ ID NO 49
<211> LENGTH: 3261
<212> TYPE: DNA
<213> ORGANISM: Corynebacterium glutamicum

<400> SEQUENCE: 49
cctcactggc gaacacggcc gactcctgga acagcgcaac atggcatgga cgaaactcaa         60
cgaaatccca ggtgtcagct gtgtgaaacc aatgggagct ctatacgcgt tccccaagct        120
cgaccccaac gtgtacgaaa tccacgacga cacccaactc atgctggatc ttctccgtgc        180
cgagaaaatc ctcatggttc agggcactgg cttcaactgg ccacatcacg atcacttccg        240
agtggtcacc ctgccatggg catcccagtt ggaaaacgca attgagcgcc tgggtaactt        300
cctgtccact tacaagcagt agtagttgtt aggattcacc acgaatctca ggattttga         360 gattcgtggt gaatttttgc gttttccagt caggctcctg caactttcgg accgatttca        420
gaggggcgga gctggtttgt ggtggatcct tgaaatggaa cctcgcagga agctttcagg        480
aagaccaagt tgggcctagg ggtggcggga ttgcaaaaat ccgtcccggg ttcgccatga        540
aatgctgatt ttgatcgaat ctttgcgcta actgtagggc gggttcaggg ggtgaatgca        600
ccacgagcaa cccgaagggt gcgaagtggg cattcgtaga acaatcccag aggaaagccg        660
tacggctttc ctcgacatga tcaatcaagg tatgtcaggt cttgctgcgt ctacagcggt        720
cggggtcagt gaattcaccg ggcgaaagtg ggcgaaggcc gccggggtga aactgacccg        780
cggcccgcga ggtggcaatg cttttgacac cgccgagaaa cttgagattg cagccagcat        840
gctagagaaa ggatgcctac cccgagaaat cggcgagtat gtcggcatga ctcgggccaa        900
tatatcccta tggcgcaaac aaggcccaga caagcttcgc caacgcgcag ccaccttgcg        960
caccggcaag cgagcagctg aattcatcca cgccccggtg atgggccctt attatgggcc       1020
acgcacactc catcaagtgt tgcgtgagga ctacacaaca ctgtttgacg agttatctgc       1080
gttggggttg ccagcacagg tgtgtggggc cttacttcat cttgctccac caccatcatt       1140 acgctttct tatatgtcgt gtgtagtgcc gttatttgct gatgaaatca aagtcgtagg       1200
acaaggcaca cgattatcgt tagaagagaa aatgatgatc caacgtttcc atgcacaccgg      1260 ggtcagtgca gcagaaatcg gtcgacgcct gggtcggtgt cggcaaacaa tttccaggga       1320
acttcgacgt ggtcaagatg atgatggacg ttatcgtgca cgcgactcct atgaaggtgc       1380
gatcaggaaa ctagcgcgtc cgaaaacacc gaaacttgat gccaatcgta ggcttcgggc       1440
tgtggtggtc gaggcgttga ataataaatt atctccggag cagatttctg gtcttttagc       1500
caccgagcat gctaacgata gctctatgca gattagtcat gaaactattt accaggcgtt       1560
atatgttcaa ggtaaagggg cgttgcgtga tgaattgaag gtggagaaat ttcttcgtac       1620
cggtcggaag ggacgtaaac cgcagtcgaa gttgccatcg agaggtaagc cgtgggtgga       1680
```

-continued

```
gggtgcgttg attagtcaac gcccagcaga agttgctgat cgtgctgtgc ctgggcactg    1740
ggagggcgat ttagtaattg gtggtgaaaa ccaagcgaca gcgttggtga cgttggtgga    1800
gcgcacgagc cggttgacgt tgattaagcg gttgggggtt aatcatgagg cgtcgactgt    1860
gacggatgcg ttggtggaga tgatgggtga tttgccgcag gcgttgcgtc ggagtttgac    1920
gtgggatcag ggtgtggaga tggcagagca tgcgcggttt agcgtggtga ccaagtgtcc    1980
ggtgtttttc tgtgatcctc attcgccgtg gcagcgtggg tcgaatgaga atacgaatgg    2040
attggtcagg gatttttttcc cgaagggcac taattttgct aaagtaagtg acgaagaagt    2100
tcagcgggca caggatctgc tgaattaccg gccgcggaaa atgcatggtt ttaaaagcgc    2160
gacgcaggta tatgaaaaaa tcgtagttgg tgcatccacc gattgaattc gcctaggaga    2220
ttgtacgaaa attcgttcgg ctttcggatt tcctggcgat ctgagacgag aagttgaaca    2280
gctaacctgc agaaaccttg caagaatcac aacagcccca atggcctcaa aagtcacgcc    2340
ctcagaatcg ctgccaggcg tctaaatccc ctaaaacggg acaataggtc actgggcgat    2400
cccaagccct taaaacgtga tccttaaata cccactgtcc tctattctgg gttaggcttc    2460
actgggtaaa agtgcctgcc tatgcctgaa acttgagcat ggcaacagca aggagacacc    2520
gtgggaaaac atgcagctga aacatcggaa ccgaagaaaa attcaccgtg gcgcattggt    2580
ttgttgacgt ttttgatttc ttcagttgtc gtgacgctgg tgggcatggt gatgctgtgg    2640
ccggattctg atgatgtggt gttggcggat aacttttcgc agacgtttgc gggaaatcat    2700
gagcaggtgg atggaacgat cacgctcgtt gataattctg cgtgtaattc gccagacacc    2760
ggccgagttt ttgcggaaag ccccacgatt tctgcggagc cggcaacgtt ggagtgcgtg    2820
cgtgcactcg tagacatcac atcgggtgcc aatgaggggc agaaaactca gctgatcact    2880
tacgcgcaac ctggtgatcc ggagtttccc gagggcgaca agatccgcat ggtggaaaca    2940
ccggatacaa atggcgagat catctacacc tttgctgatt accagcgcgg accggcgttg    3000
atcatttggg gtgtggttct cattgtggcg atgggagctt tcgcggcgtg gcgaggtgtg    3060
cgtgcgctgg ttggtttggt cgtcaccttg ggaattgttg gtattttctt gctgccagga    3120
ttggccagcg ggcacgatgc gatgtggttg gcgctggtgt gtggcgcggc gatcttgttg    3180
attgtggtgc cgatggttca cggaatcaac tggaaatcgg cagctgcgtt ggcgggcacg    3240
ctggtggcat tgttgttgtc g                                              3261
```

<210> SEQ ID NO 50
<211> LENGTH: 40
<212> TYPE: DNA
<213> ORGANISM: Artificial Sequence
<220> FEATURE:
<223> OTHER INFORMATION: Synthetic primer

<400> SEQUENCE: 50

```
gtacccgggg atcctctaga cctgggtaac ttcctgtcca                           40
```

<210> SEQ ID NO 51
<211> LENGTH: 35
<212> TYPE: DNA
<213> ORGANISM: Artificial Sequence
<220> FEATURE:
<223> OTHER INFORMATION: Synthetic primer

<400> SEQUENCE: 51

```
caggttagca gtacttctca gtttctcgg cggtg                                 35
```

-continued

```
<210> SEQ ID NO 52
<211> LENGTH: 35
<212> TYPE: DNA
<213> ORGANISM: Artificial Sequence
<220> FEATURE:
<223> OTHER INFORMATION: Synthetic primer

<400> SEQUENCE: 52
aacttgagaa gtactgctaa cctgcagaaa ccttg                               35

<210> SEQ ID NO 53
<211> LENGTH: 40
<212> TYPE: DNA
<213> ORGANISM: Artificial Sequence
<220> FEATURE:
<223> OTHER INFORMATION: Synthetic primer

<400> SEQUENCE: 53
gcctgcaggt cgactctaga ctccgcagaa atcgtggggc                          40

<210> SEQ ID NO 54
<211> LENGTH: 35
<212> TYPE: DNA
<213> ORGANISM: Artificial Sequence
<220> FEATURE:
<223> OTHER INFORMATION: Synthetic primer

<400> SEQUENCE: 54
cgccgagaaa cttgagaagt ggcgcttcat gtcaa                               35

<210> SEQ ID NO 55
<211> LENGTH: 35
<212> TYPE: DNA
<213> ORGANISM: Artificial Sequence
<220> FEATURE:
<223> OTHER INFORMATION: Synthetic primer

<400> SEQUENCE: 55
ctgcaggtta gcagtttagt caaggccccg caaca                               35

<210> SEQ ID NO 56
<211> LENGTH: 35
<212> TYPE: DNA
<213> ORGANISM: Artificial Sequence
<220> FEATURE:
<223> OTHER INFORMATION: Synthetic primer

<400> SEQUENCE: 56
ctgcaggtta gcagttcaca agctgttaag cgaag                               35

<210> SEQ ID NO 57
<211> LENGTH: 35
<212> TYPE: DNA
<213> ORGANISM: Artificial Sequence
<220> FEATURE:
<223> OTHER INFORMATION: Synthetic primer

<400> SEQUENCE: 57
ctgcaggtta gcagttcaga tcaccgcgag cgcct                               35

<210> SEQ ID NO 58
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 58
ttctccgtgc cgagaaaatc                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic primer

<400> SEQUENCE: 59
gtagatgatc tcgccatttg                                              20

<210> SEQ ID NO 60
<211> LENGTH: 394
<212> TYPE: PRT
<213> ORGANISM: Chromobacterium violaceum

<400> SEQUENCE: 60

Met Ala Ser Asp Ala Pro His Leu Pro Leu His Pro Glu Thr Leu Ala
1               5                   10                  15

Ile Arg Ala Gly Leu Glu Thr Ser Gln Phe Asn Glu His Ser Gln Gly
                20                  25                  30

Leu Phe Leu Thr Ser Ser Phe Thr Tyr Glu Ser Ala Ala Gln Ala Ala
            35                  40                  45

Ala Met Phe Leu Gly Glu Ile Asp Gly Tyr Thr Tyr Ser Arg Phe Thr
        50                  55                  60

Asn Pro Thr Val Ala Ala Phe Gln His Arg Leu Ala Gln Met Glu Gly
65                  70                  75                  80

Gly Glu Arg Ala Ile Ala Thr Ala Thr Gly Met Ala Ala Ile Gln Ala
                85                  90                  95

Ile Met Met Thr Leu Leu Gln Ala Gly Asp His Ile Val Ser Ser Gln
                100                 105                 110

Ser Leu Phe Gly Ser Thr Thr Asn Leu Phe Ala Asn Gln Leu Ala Lys
            115                 120                 125

Phe Ala Val Ala Thr Asp Phe Val Asp Ala Arg Asp Leu Ser Ala Trp
        130                 135                 140

Arg Glu Ala Leu Arg Pro Asn Thr Lys Leu Leu Phe Leu Glu Thr Pro
145                 150                 155                 160

Ser Asn Pro Leu Thr Glu Val Ala Asp Ile Ala Ala Ile Ala Asp Ile
                165                 170                 175

Ala His Ala His Gly Ala Leu Leu Val Val Asp Asn Ser Phe Cys Ser
                180                 185                 190

Pro Ala Leu Gln Gln Pro Leu Lys Leu Gly Ala Asp Leu Val Met His
            195                 200                 205

Ser Ala Thr Lys Phe Ile Asp Gly His Gly Arg Val Met Gly Gly Ala
        210                 215                 220

Val Val Gly Ser Asp Lys Leu Val Glu Gln Val Tyr Leu His Val Arg
225                 230                 235                 240

Ala Ala Gly Pro Ser Leu Ala Pro Phe Asn Ala Trp Thr Leu Leu Ser
                245                 250                 255

Gly Leu Glu Thr Leu His Leu Arg Met Glu Lys His Ser Ala Asn Ala
            260                 265                 270

Leu Glu Leu Ala Arg Trp Leu Glu Ala Gln Pro Asn Val Glu Arg Val
        275                 280                 285
```

-continued

```
Tyr Tyr Pro Gly Leu Glu Ser His Pro Gln His Glu Leu Ala Leu Arg
    290                 295             300

Gln Gln Lys Ser Gly Gly Ala Val Val Ser Phe Val Val Lys Gly Gly
305             310                 315                 320

Arg Lys Ala Ala Trp Lys Val Val Asp Ala Val Arg Val Ile Ser Arg
                325             330             335

Thr Ala Asn Leu Gly Asp Val Lys Thr Thr Leu Thr His Pro Ala Ser
            340             345             350

Thr Thr His Ala Arg Val Thr Gln Glu Ala Arg Glu Arg Ala Gly Ile
        355             360             365

Val Glu Gly Leu Leu Arg Val Ser Val Gly Leu Glu Asn Val Arg Asp
    370             375             380

Leu Gln Gln Asp Leu Leu Arg Gly Leu Asp
385             390
```

```
<210> SEQ ID NO 61
<211> LENGTH: 399
<212> TYPE: PRT
<213> ORGANISM: Unknown
<220> FEATURE:
<223> OTHER INFORMATION: Hyphomonas neptunium

<400> SEQUENCE: 61
```

```
Met Ala Asp Ala Pro Gly Gly Asp Lys Lys Gly Trp Lys Pro Ala Thr
1               5               10              15

Gln Ala Val Arg Gly Gly Leu Met Arg Ser Gln His Gly Glu Ile Ser
            20              25              30

Glu Ala Leu Tyr Leu Thr Ser Gly Tyr Ala Tyr Asp Ser Ala Glu Gln
        35              40              45

Ala Met Arg Arg Met Ala Gly Glu Glu Glu Gly Phe Val Tyr Ser Arg
    50              55              60

Tyr Gly Ser Pro Thr Asn Glu Met Leu Gln Gln Arg Leu Ala Leu Ile
65              70              75              80

Glu Gly Ala Glu Ala Cys Arg Val Thr Gly Ser Gly Met Gly Ala Ile
            85              90              95

Ser Ser Ala Ile Leu Ala Pro Leu Lys Ala Gly Asp Arg Val Val Ala
            100             105             110

Ala Thr Ala Leu Phe Gly Ser Cys Arg Trp Ile Ile Ala Asn Gln Met
        115             120             125

Pro Lys Phe Gly Ile Glu Ala Val Phe Val Asp Gly Ala Asp Leu Asp
        130             135             140

Ala Trp Lys Arg Glu Ile Asp Lys Gly Cys Gln Leu Val Leu Ile Glu
145             150             155             160

Ser Pro Ala Asn Pro Leu Leu Asp Gly Val Asp Ile Glu Ala Val Ala
            165             170             175

Arg Leu Ala Lys Ala Ala Gly Ala Leu Leu Val Val Asp Asn Val Phe
            180             185             190

Ala Thr Pro Val Leu Gln Arg Pro Leu Glu Met Gly Ala Asp Val Ile
        195             200             205

Ala Tyr Ser Ala Thr Lys His Met Asp Gly Gln Gly Arg Val Leu Leu
        210             215             220

Gly Ala Ile Leu Thr Asp Ala Lys Arg Met Ser Asp Val Tyr Asp Pro
225             230             235             240

Trp Leu Arg His Met Gly Pro Ala Ala Ser Pro Phe Asn Ala Trp Val
            245             250             255
```

-continued

```
Val Leu Lys Gly Leu Glu Thr Met Gln Leu Arg Val Glu Ala Gln Ser
            260             265             270

Arg Thr Ala Ala Arg Leu Ala Asp Val Leu Ala Asp His Pro Ala Val
            275             280             285

Asn Ala Val Arg Tyr Pro His Arg Lys Asp His Pro His Tyr Glu Val
    290             295             300

His Lys Arg Gln Met Lys Ser Gly Gly Thr Leu Leu Ala Leu Ser Leu
305             310             315             320

Lys Gly Gly Gln Asp Ala Ala Phe Arg Phe Leu Asn Gly Leu Gln Leu
            325             330             335

Val Asp Ile Cys Asn Asn Leu Gly Asp Thr Lys Ser Leu Ala Cys His
            340             345             350

Pro Ser Thr Thr Thr His Arg Ala Leu Ser Asp Glu Asp Gln Ala Ala
            355             360             365

Met Gly Leu Asp Arg Ser Trp Val Arg Leu Ser Val Gly Leu Glu Asp
    370             375             380

Ala Asp Asp Leu Glu Ala Asp Leu Leu Ala Ser Leu Asn Ser Leu
385             390             395
```

<210> SEQ ID NO 62
<211> LENGTH: 393
<212> TYPE: PRT
<213> ORGANISM: Rhodobacter sphaeroides

<400> SEQUENCE: 62

```
Met Thr Lys Asp Trp Lys Thr Arg Thr Gln Leu Val His Gly Gly Ser
1               5               10              15

Arg Arg Ser Gln Tyr Gly Glu Met Ala Glu Ala Ile Phe Leu Thr Gln
            20              25              30

Gly Phe Val Tyr Asp Ser Ala Glu Gln Ala Glu Ala Arg Phe Ile Glu
            35              40              45

Thr Gly Ala Asp Glu Phe Ile Tyr Ala Arg Tyr Gly Asn Pro Thr Thr
    50              55              60

Arg Met Phe Glu Glu Arg Ile Ala Ala Val Glu Gly Thr Glu Asp Ala
65              70              75              80

Phe Ala Thr Ala Ser Gly Met Ala Ala Ile His Gly Val Leu Thr Ser
            85              90              95

Ile Val Arg Ala Gly Asp His Leu Val Ala Ala Arg Ala Leu Phe Gly
            100             105             110

Ser Cys Ile Tyr Ile Leu Glu Glu Val Leu Gly Arg Phe Gly Val Glu
            115             120             125

Val Thr Phe Val Asp Gly Thr Asp Leu Asp Gln Trp Arg Ala Ala Val
            130             135             140

Arg Pro Gly Thr Lys Ala Val Phe Phe Glu Ser Val Ser Asn Pro Thr
145             150             155             160

Leu Glu Val Ala Asp Ile Gly Ala Ile Ala Glu Ile Ala His Ala Val
            165             170             175

Gly Ala Leu Val Ile Val Asp Asn Val Phe Ala Thr Pro Val Phe Ser
            180             185             190

Thr Ala Val Arg Gln Gly Ala Asp Val Val Ile Tyr Ser Ala Thr Lys
            195             200             205

His Ile Asp Gly Gln Gly Arg Ala Leu Gly Gly Val Val Cys Ala Ser
    210             215             220

Gln Ala Phe Ile Arg Lys Val Leu Glu Pro Phe Met Lys His Thr Gly
225             230             235             240
```

```
Gly Ser Met Ser Pro Phe Asn Ala Trp Leu Met Leu Asn Gly Met Ala
            245                 250                 255

Thr Leu Asp Leu Arg Cys Arg Ala Met Ala Asp Thr Ala Glu Lys Ile
            260                 265                 270

Ala Arg Ala Leu Glu Gly His Pro Gln Leu Gly Arg Val Ile His Pro
            275                 280                 285

Ala Leu Glu Ser His Pro Gln His Glu Met Ala Lys Ala Gln Met Glu
            290                 295                 300

Arg Pro Gly Thr Met Ile Ala Leu Asp Leu Ala Gly Gly Lys Glu Ala
305                 310                 315                 320

Ala Phe Arg Phe Leu Asp Ala Leu Arg Ile Val Lys Ile Ser Asn Asn
                325                 330                 335

Leu Gly Asp Ala Arg Ser Ile Ala Thr His Pro Ala Thr Thr Thr His
                340                 345                 350

Gln Arg Leu Ser Asp Ala Gln Lys Ala His Leu Gly Ile Thr Pro Gly
            355                 360                 365

Leu Val Arg Leu Ser Val Gly Leu Glu Asp Ala Asp Asp Leu Ile Ala
        370                 375                 380

Asp Leu Lys Gln Ala Leu Ala Val Ile
385                 390

<210> SEQ ID NO 63
<211> LENGTH: 1185
<212> TYPE: DNA
<213> ORGANISM: Chromobacterium violaceum

<400> SEQUENCE: 63
atggcatccg acgcgccgca tcttccgctg caccctgaaa ccctggccat ccgggccggg      60
ttggaaacca gccagttcaa cgagcacagc cagggcctgt tcctgacgtc cagcttcacc     120
tacgaatcgg ccgcgcaggc ggcggcgatg ttcctgggcg agatcgacgg ctacacctat     180
tcccgcttca ccaatccgac cgtcgccgcg ttccagcata ggctggcgca gatggagggc     240
ggggagcgcg ccatcgccac cgccaccggc atggcggcga tccaggccat catgatgact     300
ttgctgcagg ctggcgacca catcgtgtcg tcgcaaagcc tgttcggctc caccaccaat     360
ctgttcgcca accagttggc caagttcgcc gtggccaccg acttcgtcga cgcgcgcgac     420
ctgtccgcct ggcgggaggc gctgcggccg aacaccaagc tgctgttcct ggagacgccg     480
tccaatccct tgaccgaagt ggccgacatc gcggccatcg ccgacatcgc ccacgcgcat     540
ggcgcgctgc tggtggtgga caacagcttc tgttcgccgg ccttgcagca gccgttgaaa     600
ctgggcgccg atctggtcat gcattccgcc accaagttca tcgacggcca tggccgggtg     660
atgggcgggg cggtggtcgg cagcgacaag ctggtcgagc aggtctattt gcacgtgcgc     720
gccgccggtc cctcgctggc cgcgttcaat gcctggacgc tgctgtccgg tttggagacg     780
ctgcacctgc ggatggagaa gcacagcgcc aacgcgctgg agctggcgcg ctggctggag     840
gcgcagccca atgtggagcg cgtctattac ccgggcctgg agagccaccc ccagcacgag     900
ctggcgctgc gccagcagaa gagcggcgga gcggtggtgt ccttcgtggt caagggcggc     960
cgcaaggccg cgtggaaagt ggtggacgcg gtcaggggta tctcgcgcac cgccaatctg    1020
ggcgatgtga aaaccaccct cactcatccg gccagcacca cccacgcccg cgtgacgcag    1080
gaggcgcgcg agcgcgccgg catcgtcgag gggctgttgc cgtcagcgt cggcctggaa    1140 aatgtacggg accttcaaca agatctgttg cggggccttg actaa                    1185
```

<210> SEQ ID NO 64
<211> LENGTH: 1200
<212> TYPE: DNA
<213> ORGANISM: Unknown
<220> FEATURE:
<223> OTHER INFORMATION: Hyphomonas neptunium

<400> SEQUENCE: 64

```
atggcggatg cacccggcgg cgacaagaag ggctggaagc ctgcgaccca ggcggtacgc      60
ggcggcctga tgcggtccca gcatggggag atttccgagg cgctgtatct gacctccggc     120
tacgcttacg actcggccga gcaggcgatg cgccggatgg cgggcgagga agaaggcttc     180
gtctattccc gctatggcag cccgaccaat gagatgctgc aacagcgcct cgcgctgatt     240
gaaggcgccg aagcgtgccg ggtgacgggc tctggcatgg cgcgatttc gtcggccatc     300 ctggcgccgc ttaaagcggg cgaccgggtg gtggcggcga ccgcgctgtt tggctcgtgc     360
cgctggatca ttgccaacca gatgccgaag tttggcatcg aggcagtgtt cgtggacggg     420
gccgatcttg atgcttggaa gcgcgagatc gacaagggct gccagctggt gctgatcgaa     480
agcccggcca atccgttgct cgacggcgtg gacatcgaag cggtcgccag gctcgccaag     540
gcggcgggcg cgctgctggt ggtggacaat gtgtttgcca cgccggtgct tcagcggccg     600
ctggaaatgg cgccgatgt gatcgcctat tcggccacca aacatatgga cgggcagggc     660
cgcgttctgc tggcgcgat cctgacggac gccaagcgga tgagtgatgt gtatgatccg     720
tggctgcgcc atatggggcc ggcggcctcg ccgtttaacg cctgggtagt gctgaagggc     780
cttgagacga tgcagctgcg cgtggaagcg cagagccgca cggcggcgcg gctggcggat     840
gttctggccg atcatccggc ggtcaatgcc gtgcgctatc cccaccgcaa ggatcacccg     900
cattatgagg tgcacaagcg ccagatgaaa tcgggcggca cgctgctcgc gctgtcgctc     960
aagggcgggc aggacgcggc gttccgcttc ctcaacgggc tgcagctggt cgacatctgc    1020
aacaaccttg cgatacgaa atcgctggcc tgtcatccct ccaccacgac gcaccgcgcg    1080
ttgagtgatg aggatcaggc ggcgatgggg cttgaccgca gctgggtccg gctctctgtt    1140
ggtcttgaag acgcagatga tctggaagct gatcttctcg cttcgcttaa cagcttgtga    1200
```

<210> SEQ ID NO 65
<211> LENGTH: 1182
<212> TYPE: DNA
<213> ORGANISM: Rhodobacter sphaeroides

<400> SEQUENCE: 65

```
atgacgaagg actggaagac aaggacgcaa ctcgtccacg ggggcagccg ccggagccag      60
tatggcgaaa tggccgaggc gatcttcctg acccagggct cgtctacga ctcggccgaa     120 caggccgaag cgcgcttcat cgagaccggc gccgacgaat tcatctatgc ccgctacggc     180
aaccccacga cgcgcatgtt cgaagagcgc atcgcggccg tcgagggcac cgaggatgcg     240
ttcgccaccg cctcgggcat ggccgcgatc cacggcgtgc tcacctcgat cgtgcgggcg     300
ggcgatcatc tggtggcggc gcgcgctctg ttcggctcct gcatctacat cctcgaggag     360
gtgctgggcc gattcggcgt cgaggtgacc ttcgtcgacg gcaccgatct cgatcagtgg     420
cgcgcggcgg tgcggcccgg cacgaaggcc gtgttcttcg agtcggtctc gaatccgacg     480
ctcgaggtgg ccgatatcgg cgccatcgcc gagatcgccc atgccgtggg cgcgctcgtc     540
atcgtggaca atgtcttcgc gacgcccgtc ttctcgacgg cggtgcggca gggcgcggat     600
gtggtgatct attcggccac caagcacatc gacgggcaag ggcgcgcgct cggcggcgtg     660
```

-continued

```
gtctgcgcct cgcaggcctt catccgcaag gtgctcgaac ccttcatgaa gcacaccggc      720
ggctcgatga gccccttcaa cgcctggctc atgctgaacg ggatggcgac gctcgacctg      780
cgctgccgcg cgatggccga cacggccgag aagatcgccc gcgcgctcga gggccatccg      840
cagctcggcc gcgtgatcca tcccgcgctg gaaagccacc gcagcacga gatggccaag       900 gcgcagatgg agcgtcccgg cacgatgatc gcgctcgacc tcgccggggg caaggaggcg      960
gccttccgct tcctcgacgc cctgaggatc gtgaagatct ccaacaatct gggcgatgcc     1020
cgctcgatcg cgacccaccc ggcaacgacc acccaccagc gtctttccga cgcgcagaag     1080
gcccatctcg gcatcacgcc cgggctcgtg cggctgtcgg tggggctcga ggatgcggac     1140
gacctgatcg ccgatctgaa acaggcgctc gcggtgatct ga                        1182
```

<210> SEQ ID NO 66
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_long

<400> SEQUENCE: 66

```
Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
            20                  25                  30

Gly Glu Met Ala Glu Ala Ile Phe Leu Thr Gln Gly Phe Val Tyr Asp
        35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
            85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
            115                 120                 125

Leu Glu Glu Val Leu Gly Arg Phe Gly Val Glu Val Thr Phe Val Asp
        130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
            165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
    210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255
```

-continued

```
Phe Asn Ala Trp Leu Met Leu Asn Gly Met Ala Thr Leu Asp Leu Arg
            260                 265                 270

Cys Arg Ala Met Ala Asp Thr Ala Glu Lys Ile Ala Arg Ala Leu Glu
            275                 280                 285

Gly His Pro Gln Leu Gly Arg Val Ile His Pro Ala Leu Glu Ser His
            290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
                340                 345                 350

Ser Ile Ala Thr His Pro Ala Thr Thr Thr His Gln Arg Leu Ser Asp
            355                 360                 365

Ala Gln Lys Ala His Leu Gly Ile Thr Pro Gly Leu Val Arg Leu Ser
        370                 375                 380

Val Gly Leu Glu Asp Ala Asp Asp Leu Ile Ala Asp Leu Lys Gln Ala
385                 390                 395                 400

Leu Ala Val Ile
```

<210> SEQ ID NO 67
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_3

<400> SEQUENCE: 67

```
Met Gly Asn Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
            20                  25                  30

Gly Glu Met Ala Glu Ala Ile Phe Leu Thr Gln Gly Phe Val Tyr Asp
            35                  40                  45

Ser Ala Glu Gln Ala Glu Ala Arg Phe Ile Glu Thr Gly Ala Asp Glu
    50                  55                  60

Phe Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
            115                 120                 125

Leu Glu Glu Val Leu Gly Arg Phe Gly Val Glu Val Thr Phe Val Asp
        130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205
```

```
Gly Ala Asp Val Val Ile Tyr Ser Ala Thr Lys His Ile Asp Gly Gln
    210             215                 220

Gly Arg Ala Leu Gly Gly Val Val Cys Ala Ser Gln Ala Phe Ile Arg
225             230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
                260                 265                 270

Cys Arg Ala Met Ala Asp Thr Ala Glu Lys Ile Ala Arg Ala Leu Glu
                275                 280                 285

Gly His Pro Gln Leu Gly Arg Val Ile His Pro Ala Leu Glu Ser His
            290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
                340                 345                 350

Ser Ile Ala Thr His Pro Ala Thr Thr Thr His Gln Arg Leu Ser Asp
            355                 360                 365

Ala Gln Lys Ala His Leu Gly Ile Thr Pro Gly Leu Val Arg Leu Ser
    370                 375                 380

Val Gly Leu Glu Asp Ala Asp Asp Leu Ile Ala Asp Leu Lys Gln Ala
385                 390                 395                 400

Leu Ala Val Ile

<210> SEQ ID NO 68
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_65

<400> SEQUENCE: 68

Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
                20                  25                  30

Gly Glu Met Ala Glu Ala Ile Phe Leu Thr Gln Gly Phe Val Tyr Asp
            35                  40                  45

Ser Ala Glu Gln Ala Glu Ala Arg Phe Ile Glu Thr Gly Ala Asp Glu
    50                  55                  60

Tyr Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Val Leu Thr Ser Ile Val Arg Ala Gly
            100                 105                 110

Asp His Leu Val Ala Ala Arg Ala Leu Phe Gly Ser Cys Ile Tyr Ile
            115                 120                 125

Leu Glu Glu Val Leu Gly Arg Phe Gly Val Glu Val Thr Phe Val Asp
    130                 135                 140

Gly Thr Asp Leu Asp Gln Trp Arg Ala Ala Val Arg Pro Gly Thr Lys
```

-continued

```
145              150              155              160

Ala Val Phe Phe Glu Ser Val Ser Asn Pro Thr Leu Glu Val Ala Asp
                165              170              175

Ile Gly Ala Ile Ala Glu Ile Ala His Ala Val Gly Ala Leu Val Ile
                180              185              190

Val Asp Asn Val Phe Ala Thr Pro Val Phe Ser Thr Ala Val Arg Gln
                195              200              205

Gly Ala Asp Val Val Ile Tyr Ser Ala Thr Lys His Ile Asp Gly Gln
            210              215              220

Gly Arg Ala Leu Gly Gly Val Val Cys Ala Ser Gln Ala Phe Ile Arg
225              230              235              240

Lys Val Leu Glu Pro Phe Met Lys His Thr Gly Gly Ser Met Ser Pro
                245              250              255

Phe Asn Ala Trp Leu Met Leu Asn Gly Met Ala Thr Leu Asp Leu Arg
                260              265              270

Cys Arg Ala Met Ala Asp Thr Ala Glu Lys Ile Ala Arg Ala Leu Glu
                275              280              285

Gly His Pro Gln Leu Gly Arg Val Ile His Pro Ala Leu Glu Ser His
            290              295              300

Pro Gln His Glu Met Ala Lys Ala Gln Met Glu Arg Pro Gly Thr Met
305              310              315              320

Ile Ala Leu Asp Leu Ala Gly Gly Lys Glu Ala Ala Phe Arg Phe Leu
                325              330              335

Asp Ala Leu Arg Ile Val Lys Ile Ser Asn Asn Leu Gly Asp Ala Arg
                340              345              350

Ser Ile Ala Thr His Pro Ala Thr Thr Thr His Gln Arg Leu Ser Asp
                355              360              365

Ala Gln Lys Ala His Leu Gly Ile Thr Pro Gly Leu Val Arg Leu Ser
            370              375              380

Val Gly Leu Glu Asp Ala Asp Asp Leu Ile Ala Asp Leu Lys Gln Ala
385              390              395              400

Leu Ala Val Ile
```

<210> SEQ ID NO 69
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_104

<400> SEQUENCE: 69

```
Met Gly Ile Ala Phe Arg Glu Gly Arg Thr Gly Met Thr Lys Asp Trp
1               5               10              15

Lys Thr Arg Thr Gln Leu Val His Gly Gly Ser Arg Arg Ser Gln Tyr
                20              25              30

Gly Glu Met Ala Glu Ala Ile Phe Leu Thr Gln Gly Phe Val Tyr Asp
                35              40              45

Ser Ala Glu Gln Ala Glu Ala Arg Phe Ile Glu Thr Gly Ala Asp Glu
            50              55              60

Phe Ile Tyr Ala Arg Tyr Gly Asn Pro Thr Thr Arg Met Phe Glu Glu
65              70              75              80

Arg Ile Ala Ala Val Glu Gly Thr Glu Asp Ala Phe Ala Thr Ala Ser
                85              90              95
```

-continued

```
Gly Met Ala Ala Ile His Gly Ala Leu Thr Ser Ile Val Arg Ala Gly
            100                 105                 110

Asp His Leu Val Ala Ala Arg Ala Leu Phe Gly Ser Cys Ile Tyr Ile
            115                 120                 125

Leu Glu Glu Val Leu Gly Arg Phe Gly Val Glu Val Thr Phe Val Asp
            130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
            195                 200                 205

Gly Ala Asp Val Val Ile Tyr Ser Ala Thr Lys His Ile Asp Gly Gln
            210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
                260                 265                 270

Cys Arg Ala Met Ala Asp Thr Ala Glu Lys Ile Ala Arg Ala Leu Glu
            275                 280                 285

Gly His Pro Gln Leu Gly Arg Val Ile His Pro Ala Leu Glu Ser His
            290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
            355                 360                 365

Ala Gln Lys Ala His Leu Gly Ile Thr Pro Gly Leu Val Arg Leu Ser
    370                 375                 380

Val Gly Leu Glu Asp Ala Asp Asp Leu Ile Ala Asp Leu Lys Gln Ala
385                 390                 395                 400

Leu Ala Val Ile
```

```
<210> SEQ ID NO 70
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_196

<400> SEQUENCE: 70
```

```
Met Gly Ile Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
            20                  25                  30

Gly Glu Met Ala Glu Ala Ile Phe Leu Thr Gln Gly Phe Val Tyr Asp
            35                  40                  45
```

-continued

```
Ser Ala Glu Gln Ala Glu Ala Arg Phe Ile Glu Thr Gly Ala Asp Glu
    50              55              60

Phe Ile Tyr Ala Arg Tyr Gly Asn Pro Thr Thr Arg Met Phe Glu Glu
65              70              75              80

Arg Ile Ala Ala Val Glu Gly Thr Glu Asp Ala Phe Ala Thr Ala Ser
                85              90              95

Gly Met Ala Ala Ile His Gly Val Leu Thr Ser Ile Val Arg Ala Gly
            100             105             110

Asp His Leu Val Ala Ala Arg Ala Leu Phe Gly Ser Cys Ile Tyr Ile
        115             120             125

Leu Glu Glu Val Leu Gly Arg Phe Gly Val Glu Val Thr Phe Val Asp
    130             135             140

Gly Thr Asp Leu Asp Gln Trp Arg Ala Ala Val Arg Pro Gly Thr Lys
145             150             155             160

Ala Val Phe Phe Glu Ser Val Ser Asn Pro Thr Leu Glu Val Ala Asp
                165             170             175

Ile Gly Ala Ile Ala Glu Ile Ala His Ala Val Gly Ala Leu Val Ile
            180             185             190

Val Asp Asn Ile Phe Ala Thr Pro Val Phe Ser Thr Ala Val Arg Gln
        195             200             205

Gly Ala Asp Val Val Ile Tyr Ser Ala Thr Lys His Ile Asp Gly Gln
    210             215             220

Gly Arg Ala Leu Gly Gly Val Val Cys Ala Ser Gln Ala Phe Ile Arg
225             230             235             240

Lys Val Leu Glu Pro Phe Met Lys His Thr Gly Gly Ser Met Ser Pro
                245             250             255

Phe Asn Ala Trp Leu Met Leu Asn Gly Met Ala Thr Leu Asp Leu Arg
            260             265             270

Cys Arg Ala Met Ala Asp Thr Ala Glu Lys Ile Ala Arg Ala Leu Glu
        275             280             285

Gly His Pro Gln Leu Gly Arg Val Ile His Pro Ala Leu Glu Ser His
    290             295             300

Pro Gln His Glu Met Ala Lys Ala Gln Met Glu Arg Pro Gly Thr Met
305             310             315             320

Ile Ala Leu Asp Leu Ala Gly Gly Lys Glu Ala Ala Phe Arg Phe Leu
            325             330             335

Asp Ala Leu Arg Ile Val Lys Ile Ser Asn Asn Leu Gly Asp Ala Arg
        340             345             350

Ser Ile Ala Thr His Pro Ala Thr Thr Thr His Gln Arg Leu Ser Asp
    355             360             365

Ala Gln Lys Ala His Leu Gly Ile Thr Pro Gly Leu Val Arg Leu Ser
    370             375             380

Val Gly Leu Glu Asp Ala Asp Asp Leu Ile Ala Asp Leu Lys Gln Ala
385             390             395             400

Leu Ala Val Ile
```

```
<210> SEQ ID NO 71
<211> LENGTH: 404
<212> TYPE: PRT
<213> ORGANISM: Artificial Sequence
<220> FEATURE:
<223> OTHER INFORMATION: Synthetic
<220> FEATURE:
<223> OTHER INFORMATION: RspmetZ_3_65_104
```

-continued

```
<400> SEQUENCE: 71

Met Gly Asn Ala Phe Arg Glu Gly Arg Thr Gly Met Thr Lys Asp Trp
1               5                   10                  15

Lys Thr Arg Thr Gln Leu Val His Gly Gly Ser Arg Arg Ser Gln Tyr
                20                  25                  30

Gly Glu Met Ala Glu Ala Ile Phe Leu Thr Gln Gly Phe Val Tyr Asp
            35                  40                  45

Ser Ala Glu Gln Ala Glu Ala Arg Phe Ile Glu Thr Gly Ala Asp Glu
        50                  55                  60

Tyr Ile Tyr Ala Arg Tyr Gly Asn Pro Thr Thr Arg Met Phe Glu Glu
65                  70                  75                  80

Arg Ile Ala Ala Val Glu Gly Thr Glu Asp Ala Phe Ala Thr Ala Ser
                85                  90                  95

Gly Met Ala Ala Ile His Gly Ala Leu Thr Ser Ile Val Arg Ala Gly
            100                 105                 110

Asp His Leu Val Ala Ala Arg Ala Leu Phe Gly Ser Cys Ile Tyr Ile
        115                 120                 125

Leu Glu Glu Val Leu Gly Arg Phe Gly Val Glu Val Thr Phe Val Asp
        130                 135                 140

Gly Thr Asp Leu Asp Gln Trp Arg Ala Ala Val Arg Pro Gly Thr Lys
145                 150                 155                 160

Ala Val Phe Phe Glu Ser Val Ser Asn Pro Thr Leu Glu Val Ala Asp
                165                 170                 175

Ile Gly Ala Ile Ala Glu Ile Ala His Ala Val Gly Ala Leu Val Ile
            180                 185                 190

Val Asp Asn Val Phe Ala Thr Pro Val Phe Ser Thr Ala Val Arg Gln
        195                 200                 205

Gly Ala Asp Val Val Ile Tyr Ser Ala Thr Lys His Ile Asp Gly Gln
        210                 215                 220

Gly Arg Ala Leu Gly Gly Val Val Cys Ala Ser Gln Ala Phe Ile Arg
225                 230                 235                 240

Lys Val Leu Glu Pro Phe Met Lys His Thr Gly Gly Ser Met Ser Pro
                245                 250                 255

Phe Asn Ala Trp Leu Met Leu Asn Gly Met Ala Thr Leu Asp Leu Arg
            260                 265                 270

Cys Arg Ala Met Ala Asp Thr Ala Glu Lys Ile Ala Arg Ala Leu Glu
        275                 280                 285

Gly His Pro Gln Leu Gly Arg Val Ile His Pro Ala Leu Glu Ser His
        290                 295                 300

Pro Gln His Glu Met Ala Lys Ala Gln Met Glu Arg Pro Gly Thr Met
305                 310                 315                 320

Ile Ala Leu Asp Leu Ala Gly Gly Lys Glu Ala Ala Phe Arg Phe Leu
                325                 330                 335

Asp Ala Leu Arg Ile Val Lys Ile Ser Asn Asn Leu Gly Asp Ala Arg
            340                 345                 350

Ser Ile Ala Thr His Pro Ala Thr Thr Thr His Gln Arg Leu Ser Asp
        355                 360                 365

Ala Gln Lys Ala His Leu Gly Ile Thr Pro Gly Leu Val Arg Leu Ser
        370                 375                 380

Val Gly Leu Glu Asp Ala Asp Asp Leu Ile Ala Asp Leu Lys Gln Ala
385                 390                 395                 400

Leu Ala Val Ile
```

-continued

```
<210> SEQ ID NO 72
<211> LENGTH: 35
<212> TYPE: DNA
<213> ORGANISM: Artificial Sequence
<220> FEATURE:
<223> OTHER INFORMATION: Synthetic primer

<400> SEQUENCE: 72
atcaaaacag atatcatggg tatcgcgttt cgtga                              35

<210> SEQ ID NO 73
<211> LENGTH: 31
<212> TYPE: DNA
<213> ORGANISM: Artificial Sequence
<220> FEATURE:
<223> OTHER INFORMATION: Synthetic primer

<400> SEQUENCE: 73
ccttcacgaa acgcgttacc catgatatct g                                 31

<210> SEQ ID NO 74
<211> LENGTH: 31
<212> TYPE: DNA
<213> ORGANISM: Artificial Sequence
<220> FEATURE:
<223> OTHER INFORMATION: Synthetic primer

<400> SEQUENCE: 74
cagatatcat gggtaacgcg tttcgtgaag g                                 31

<210> SEQ ID NO 75
<211> LENGTH: 31
<212> TYPE: DNA
<213> ORGANISM: Artificial Sequence
<220> FEATURE:
<223> OTHER INFORMATION: Synthetic primer

<400> SEQUENCE: 75
tagcgggcat agatgtattc gtcggcgccg g                                 31

<210> SEQ ID NO 76
<211> LENGTH: 31
<212> TYPE: DNA
<213> ORGANISM: Artificial Sequence
<220> FEATURE:
<223> OTHER INFORMATION: Synthetic primer

<400> SEQUENCE: 76
ccggcgccga cgaatacatc tatgcccgct a                                 31

<210> SEQ ID NO 77
<211> LENGTH: 31
<212> TYPE: DNA
<213> ORGANISM: Artificial Sequence
<220> FEATURE:
<223> OTHER INFORMATION: Synthetic primer

<400> SEQUENCE: 77
acgatcgagg tgagcgcgcc gtggatcgcg g                                 31

<210> SEQ ID NO 78
<211> LENGTH: 31
<212> TYPE: DNA
<213> ORGANISM: Artificial Sequence
<220> FEATURE:
<223> OTHER INFORMATION: Synthetic primer
```

<400> SEQUENCE: 78
ccgcgatcca cggcgcgctc acctcgatcg t                                   31

<210> SEQ ID NO 79
<211> LENGTH: 31
<212> TYPE: DNA
<213> ORGANISM: Artificial Sequence
<220> FEATURE:
<223> OTHER INFORMATION: Synthetic primer

<400> SEQUENCE: 79
cgggcgtcgc gaagatattg tccacgatga c                                   31

<210> SEQ ID NO 80
<211> LENGTH: 31
<212> TYPE: DNA
<213> ORGANISM: Artificial Sequence
<220> FEATURE:
<223> OTHER INFORMATION: Synthetic primer

<400> SEQUENCE: 80
gtcatcgtgg acaatatctt cgcgacgccc g                                   31

<210> SEQ ID NO 81
<211> LENGTH: 5803
<212> TYPE: DNA
<213> ORGANISM: Artificial Sequence
<220> FEATURE:
<223> OTHER INFORMATION: Synthetic primer
<220> FEATURE:
<223> OTHER INFORMATION: pDCM2
<220> FEATURE:
<221> NAME/KEY: misc_feature
<222> LOCATION: 2895
<223> OTHER INFORMATION: n = A,T,C or G

<400> SEQUENCE: 81
gttcgcttgc tgtccataaa accgcccagt ctagctatcg ccatgtaagc ccactgcaag      60
ctacctgctt tctctttgcg cttgcgtttt cccttgtcca gatagcccag tagctgacat     120
tcatccgggg tcagcaccgt ttctgcggac tggctttcta cgtgttccgc ttcctttagc     180
agcccttgcg ccctgagtgc ttgcggcagc gtgaagctag cttttatcgc cattcgccat     240
tcaggctgcg caactgttgg gaagggcgat cggtgcgggc ctcttcgcta ttacgccagc     300
tggcgaaagg gggatgtgct gcaaggcgat taagttgggt aacgccaggg ttttcccagt     360
cacgacgttg taaaacgacg gccagtgaat tcgagctcgg tacccgggga tcctctagag     420
tcgacctgca ggcatgcaag cttggcgtaa tcatggtcat agctgtttcc tgtgtgaaat     480
tgttatccgc tcacaattcc acacaacata cgagccggaa gcataaagtg taaagcctgg     540
ggtgcctaat gagtgagcta actcacatta attgcgttgc gctcactgcc cgctttccag     600
tcgggaaacc tgtcgtgcca gctgcattaa tgaatcggcc aacgcgcggg gagaggcggt     660
ttgcgtattg ggcgctcttc cgcttcctcg ctcactgact cgctgcgctc ggtcgttcgg     720
ctgcggcgag cggtatcagc tcactcaaag gcggtaatac ggttatccac agaatcaggg     780
gataacgcag gaaagaacat gtgagcaaaa ggccagcaaa aggccaggaa ccgtaaaaag     840
gccgcgttgc tggcgttttt ccataggctc cgcccccctg acgagcatca caaaaatcga     900
cgctcaagtc agaggtggcg aaacccgaca ggactataaa gataccaggc gtttccccct     960
ggaagctccc tcgtgcgctc tcctgttccg accctgccgc ttaccggata cctgtccgcc    1020

-continued

```
tttctccctt cgggaagcgt ggcgctttct caatgctcac gctgtaggta tctcagttcg   1080
gtgtaggtcg ttcgctccaa gctgggctgt gtgcacgaac cccccgttca gcccgaccgc   1140
tgcgccttat ccggtaacta tcgtcttgag tccaacccgg taagacacga cttatcgcca   1200
ctggcagcag ccactggtaa caggattagc agagcgaggt atgtaggcgg tgctacagag   1260
ttcttgaagt ggtggcctaa ctacggctac actagaagga cagtatttgg tatctgcgct   1320
ctgctgaagc cagttacctt cggaaaaaga gttggtagct cttgatccgg caaacaaacc   1380
accgctggta gcggtggttt ttttgtttgc aagcagcaga ttacgcgcag aaaaaaagga   1440
tctcaagaag atcctttgat cttttctacg gggtctgacg ctcagtggaa cgaaaactca   1500
cgttaaggga ttttggtcat gagattatca aaaaggatct tcacctagat cctttttgggg   1560 tgggcgaaga actccagcat gagatccccg cgctggagga tcatccagcc ctgatagaaa   1620
cagaagccac tggagcacct caaaaacacc atcatacact aaatcagtaa gttggcagca   1680
tcacccgacg cactttgcgc cgaataaata cctgtgacgg aagatcactt cgcagaataa   1740
ataaatcctg gtgtccctgt tgataccggg aagccctggg ccaacttttg gcgaaaatga   1800
gacgttgatc ggcacgtaag aggttccaac tttcaccata atgaaataag atcactaccg   1860
ggcgtatttt ttgagttatc gagattttca ggagctgata gaaacagaag ccactggagc   1920
acctcaaaaa caccatcata cactaaatca gtaagttggc agcatcaccc gacgcacttt   1980
gcgccgaata aatacctgtg acggaagatc acttcgcaga ataaataaat cctggtgtcc   2040
ctgttgatac cgggaagccc tgggccaact tttggcgaaa atgagacgtt gatcggcacg   2100
taagaggttc caactttcac cataatgaaa taagatcact accgggcgta ttttttgagt   2160
tatcgagatt ttcaggagct ctttggcatc gtctctcgcc tgtcccctca gttcagtaat   2220
ttcctgcatt tgcctgtttc cagtcggtag atattccaca aaacagcagg gaagcagcgc   2280
ttttccgctg cataaccctg cttcggggtc attatagcga ttttttcggt atatccatcc   2340
tttttcgcac gatatacagg attttgccaa agggttcgtg tagactttcc ttggtgtatc   2400
caacggcgtc agccgggcag gataggtgaa gtaggcccac ccgcgagcgg gtgttccttc   2460
ttcactgtcc cttattcgca cctggcggtg ctcaacggga tcctgctct gcgaggctgg   2520 ccggctaccg ccggcgtaac agatgagggc aagcggatgg ctgatgaaac caagccaacc   2580
aggaagggca gcccacctat caaggtgtac tgccttccag acgaacgaag agcgattgag   2640
gaaaaggcgg cggcggccgg catgagcctg tcggcctacc tgctggccgt cggccagggc   2700
tacaaaatca cgggcgtcgt ggactatgag cacgtccgcg agggcgtccc ggaaaacgat   2760
tccgaagccc aacctttcat agaaggcggc ggtggaatcg aaatctcgtg atggcaggtt   2820
gggcgtcgct tggtcggtca tttcgaaaaa ggttaggaat acggttagcc atttgcctgc   2880
ttttatatag ttcantatgg gattcacctt tatgttgata agaaataaaa gaaaatgcca   2940
ataggatatc ggcattttct tttgcgtttt tatttgttaa ctgttaattg tccttgttca   3000
aggatgctgt ctttgacaac agatgttttc ttgcctttga tgttcagcag gaagctcggc   3060
gcaaacgttg attgtttgtc tgcgtagaat cctctgtttg tcatatagct tgtaatcacg   3120
acattgtttc ctttcgcttg aggtacacgc aagtgtgagt aagtaaaggt tacatcgtta   3180
ggcggatcaa gatccatttt taacacaagg ccagttttgt tcagcggctt gtatgggcca   3240
gttaaagaat tagaaacata accaagcatg taaatatcgt tagacgtaat gccgtcaatc   3300
gtcatttttg atccgcggga gtcagtgaac aggtaccatt tgccgttcat tttaaagacg   3360
ttcgcgcgtt caatttcatc tgttactgtg ttagatgcaa tcagcggttt catcactttt   3420
```

-continued

```
ttcagtgtgt aatcatcgtt tagctcaatc ataccgagag cgccgtttgc taactcagcc      3480
gtgcgttttt tatcgctttg cagaagtttt tgactttctt gacggaagaa tgatgtgctt      3540
ttgccatagt atgctttgtt aaataaagat tcttcgcctt ggtagccatc ttcagttcca      3600
gtgtttgctt caaatactaa gtatttgtgg cctttatctt ctacgtagtg aggatctctc      3660
agcgtatggt tgtcgcctga gctgtagttg ccttcatcga tgaactgctg tacattttga      3720
tacgtttttc cgtcaccgtc aaagattgat ttataatcct ctacaccgtt gatgttcaaa      3780
gagctgtctg atgctgatac gttaacttgt gcagttgtca gtgtttgttt gccgtaatgt      3840
ttaccggaga aatcagtgta gaataaacgg attttttccgt cagatgtaaa tgtggctgaa      3900
cctgaccatt cttgtgtttg gtcttttagg atagaatcat ttgcatcgaa tttgtcgctg      3960
tctttaaaga cgcggccagc gttttttccag ctgtcaatag aagtttcgcc gactttttga      4020
tagaacatgt aaatcgatgt gtcatccgca tttttaggat ctccggctaa tgcaaagacg      4080
atgtggtagc cgtgatagtt tgcgacagtg ccgtcagcgt tttgtaatgg ccagctgtcc      4140
caaacgtcca ggccttttgc agaagagata tttttaattg tggacgaatc aaattcagaa      4200
acttgatatt tttcattttt ttgctgttca gggatttgca gcatatcatg gcgtgtaata      4260
tgggaaatgc cgtatgtttc cttatatggc ttttggttcg tttctttcgc aaacgcttga      4320
gttgcgcctc ctgccagcag tgcggtagta aaggttaata ctgttgcttg ttttgcaaac      4380 ttttttgatgt tcatcgttca tgtctccttt tttatgtact gtgttagcgg tctgcttctt      4440
ccagccctcc tgtttgaaga tggcaagtta gttacgcaca ataaaaaaag acctaaaata      4500
tgtaaggggt gacgccaaag tatacacttt gccctttaca catttttaggt cttgcctgct      4560 ttatcagtaa caaacccgcg cgatttactt ttcgacctca ttctattaga ctctcgtttg      4620
gattgcaact ggtctatttt cctctttttgt ttgatagaaa atcataaaag gatttgcaga      4680
ctacgggcct aaagaactaa aaaatctatc tgtttctttt cattctctgt atttttttata      4740 gtttctgttg catgggcata aagttgcctt tttaatcaca attcagaaaa tatcataata      4800
tctcatttca ctaaataata gtgaacggca ggtatatgtg atgggttaaa aaggatcacc      4860
ccagagtccc gctcagaaga actcgtcaag aaggcgatag aaggcgatgc gctgcgaatc      4920
gggagcggcg ataccgtaaa gcacgaggaa gcggtcagcc cattcgccgc caagctcttc      4980
agcaatatca cgggtagcca acgctatgtc ctgatagcgg tccgccacac ccagccggcc      5040
acagtcgatg aatccagaaa agcggccatt ttccaccatg atattcggca agcaggcatc      5100
gccatgggtc acgacgagat cctcgccgtc gggcatccgc gccttgagcc tggcgaacag      5160
ttcggctggc gcgagcccct gatgctcttc gtccagatca tcctgatcga caagaccggc      5220
ttccatccga gtacgtgctc gctcgatgcg atgtttcgct tggtggtcga atgggcaggt      5280
agccggatca agcgtatgca gccgccgcat tgcatcagcc atgatggata ctttctcggc      5340
aggagcaagg tgagatgaca ggagatcctg ccccggcact cgcccaata gcagccagtc      5400 ccttcccgct tcagtgacaa cgtcgagaca gctgcgcaag gaacgcccgt cgtggccagc      5460
cacgatagcc gcgctgcctc gtcttggagt tcattcaggg caccggacag gtcggtcttg      5520
acaaaaagaa ccgggcgccc ctgcgctgac agccggaaca cggcggcatc agagcagccg      5580
attgtctgtt gtgcccagtc atagccgaat agcctctcca cccaagcggc cggagaacct      5640
```

-continued

```
gcgtgcaatc catcttgttc aatcatgcga aacgatcctc atcctgtctc ttgatcagat    5700
cttgatcccc tgcgccatca gatccttggc ggcaagaaag ccatccagtt tactttgcag    5760
ggcttcccaa ccttaccaga gggcgcccca gctggcaatt ccg                      5803
```

L-METHIONINE PRODUCING MICROORGANISM TO WHICH PROTEIN ENCODED BY FOREIGN *metZ* GENE IS INTRODUCED AND METHOD FOR PRODUCING L-METHIONINE USING SAME

CROSS-REFERENCE TO RELATED APPLICATIONS

This application is a U.S. National Phase Application of PCT International Application No. PCT/KR2020/014780, filed on Oct. 28, 2020, designating the United States of America, which is an International Application of and claims the benefit of priority to Korean Patent Application No. 10-2019-0134797, filed on Oct. 28, 2019, the entire contents of which are incorporated herein by reference.

SEQUENCE LISTING STATEMENT

The present application contains a Sequence Listing, which is being submitted via EFS-Web on even date herewith. The Sequence Listing is submitted in a file entitled "Sequence_Listing_HANO30-013APC.txt," which was created on Apr. 18, 2022, and is approximately 83,000 bytes in size. This Sequence Listing is hereby incorporated by reference.

BACKGROUND OF THE INVENTION

1. Field of the Invention

The present disclosure relates to an L-methionine-producing microorganism, into which a protein encoded by a foreign *metZ* gene is introduced, and a method of producing L-methionine using the same.

2. Description of the Related Art

L-Methionine, one of the essential amino acids in the body, is used as a feed, a medical raw material such as a synthetic raw material for medical solutions, medical supplies, etc., and a food additive. Methionine is an important amino acid involved in a methyl group transfer reaction in the body, and has a role in supplying sulfur.

In chemical synthesis of methionine, a method of producing methionine in a mixture of L- and D-types through hydrolysis of 5-(R-methylmercaptoethyl)-hydantoin is mainly used. However, this chemical synthesis produces a mixed form of L- and D-types.

Meanwhile, L-methionine may be also produced by way of a biological method. More specifically, one method of producing L-methionine using microorganisms is to produce methionine by direct sulfhydrylation using O-acylhomoserine (O-acetyl homoserine or O-succinyl homoserine) and hydrogen sulfide as substrates. For example, an enzyme encoded by a metY gene in *Corynebacterium* is known to perform a direct sulfhydrylation function. Another method of producing L-methionine by microorganisms is to produce methionine by transsulfuration using O-acylhomoserine (O-acetyl homoserine or O-succinyl homoserine) and cysteine as substrates. For example, an enzyme encoded by a metB gene in *Corynebacterium* is known to perform a transsulfuration function.

However, there are disadvantages in that the enzyme encoded by metB produces many by-products, and the metY gene receives feedback inhibition, and therefore, it is difficult to apply these to industrial mass-production of L-methionine (Kromer J O et al., *J Bacteriol* 188(2):609-618, 2006; Yeom H J et al., *J Microbiol Biotechnol* 14(2):373-378, 2004; etc.).

The present inventors have made every effort to develop a protein that may replace the protein, and as a result, they found that a microorganism, into which a protein encoded by a *metZ* gene is introduced, produces L-methionine in a high yield, thereby completing the present disclosure.

SUMMARY OF THE INVENTION

An object of the present invention is to provide an L-methionine-producing microorganism, into which a protein encoded by a foreign *metZ* gene is introduced.

Another object of the present invention is to provide a method of producing L-methionine, the method including culturing the microorganism in a medium containing thiosulfate.

Still another object of the present invention is to provide a composition for producing L-methionine, the composition including the microorganism and thiosulfate.

BRIEF DESCRIPTION OF THE DRAWINGS

FIG. 1 shows an illustration of a pDCM2 plasmid.

DETAILED DESCRIPTION OF THE PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, those skilled in the art will recognize, or be able to ascertain using no more than routine experimentation, many equivalents to the specific embodiments of the disclosure described herein. Further, these equivalents should be interpreted to fall within the present disclosure.

One aspect of the present disclosure provides an L-methionine-producing microorganism, into which a protein encoded by a foreign *metZ* gene is introduced.

Another aspect of the present disclosure provides a method of producing L-methionine, the method including culturing the L-methionine-producing microorganism in a medium containing thiosulfate.

As used herein, the term "*metZ* gene" is a gene encoding an enzyme involved in sulfhydration using acylhomoserine as a substrate.

As used herein, the "acylhomoserine" refers to a compound in which an acyl group is bound to homoserine, and includes both succinylhomoserine and acetylhomoserine. For example, the acylhomoserine may be O-succinylhomoserine or O-acetylhomoserine, but is not limited thereto.

As used herein, the enzyme encoded by the *metZ* gene may be succinylhomoserine sulfhydrylase, acetylhomoserine sulfhydrylase, or an enzyme involved in sulfhydration using O-succinylhomoserine as a substrate, but is not limited thereto.

As used herein, the term "sulfhydration" may be used interchangeably with the term "sulfhydrylation", and refers to a reaction that provides a sulfhydryl (—SH) group for a specific molecule. With respect to the objects of the present disclosure, the term may refer to a reaction in the synthetic process of methionine, but is not limited thereto. The enzyme involved in the "sulfhydration" may be also called "sulfhydrylase", but is not limited thereto.

In traditional fermentation of methionine, the enzyme expressed by the *metZ* gene has been used in the following reactions in vitro:

$$CH_3SH+O\text{-acetyl-L-homoserine}=>\text{acetate}+\text{methionine}$$

$$CH_3SH+O\text{-succinyl-L-homoserine}=>\text{succinate}+\text{methionine}$$

In other words, in a method of producing methionine, the method including a first step of preparing a methionine precursor using a microorganism; and a second step of performing an enzymatic reaction in vitro by adding methyl mercaptan and a methionine-converting enzyme to a fermentation solution including the methionine precursor, the enzyme expressed by the *metZ* gene was used as the methionine-converting enzyme in vitro (see US 2010-0184164 A1).

Meanwhile, in the methionine fermentation in a microorganism of the genus *Corynebacterium*, two kinds of sulfhydration pathways (sulfhydrylation steps) are used (Hwang B J et al., *J Bacteriol* 184(5):1277-1286, 2002). One of them is to convert O-acetylhomoserine (acetyl homoserine: AH) into cystathionine using an enzyme encoded by a metB gene. In this case, cysteine is used as a sulfur source. In other words, a reaction that converts acylhomoserine and cysteine as reactants into cystathionine is called "transsulfuration", and an enzyme involved in this reaction is called "transsulfurase". The other is to convert O-acetyl homoserine into homocysteine using an enzyme encoded by a metY gene. In this case, an inorganic sulfur compound such as hydrogen sulfide, etc. is used as a sulfur source. In such a reaction that converts acylhomoserine and hydrogen sulfide as reactants into homocysteine, cystathionine as an intermediate is not produced during a process of producing homocysteine which is a methionine precursor, unlike the above-described transsulfuration. This reaction is referred to as direct sulfhydrylation.

In other words, the sulfhydration pathway may refer to a reaction pathway that converts acylhomoserine into another material by a reaction with a sulfur source, and may be largely divided into transsulfuration and direct sulfhydration.

However, in *Corynebacterium* strains, both the two enzymes involved in the sulfhydration have disadvantages. For example, the protein encoded by the metB gene produces a by-product homolanthionine by using acetylhomoserine and homocysteine, in addition to cystathionine (Kromer J O et al., *J Bacteriol* 188(2):609-618, 2006). Further, the metY gene is known to receive feedback inhibition by methionine (Yeom H J et al., *J Microbiol Biotechnol* 14(2):373-378, 2004).

The present disclosure is characterized in that the foreign *metZ* gene is introduced into a *Corynebacterium* strain to biologically produce methionine only via a single-step reaction, and it is demonstrated that introduction of the *metZ* gene is usefully applied to methionine fermentation.

In the methionine synthetic pathway, in which the protein encoded by the *metZ* gene of the present disclosure is involved, generation of by-products may be reduced. The by-product may be homolanthionine. The reduced generation of by-products may refer to reduced generation of by-products, as compared with the generation of by-products in a wild-type microorganism or in a synthetic pathway, in which a protein encoded by the metB gene is involved, but is not limited thereto.

Therefore, the microorganism of the present disclosure, into which the foreign *metZ* gene is introduced, and the method of producing methionine, the method including culturing the microorganism, may exhibit reduced generation of by-products, as compared with a methionine-producing microorganism, into which the foreign *metZ* gene is not introduced, and a method of producing methionine using the microorganism. The protein encoded by the *metZ* gene of the present disclosure may not receive feedback inhibition by methionine.

The protein encoded by the *metZ* gene of the present disclosure is O-acylhomoserine sulfhydrylase which may utilize hydrogen sulfide as a sulfur source, and is also O-acylhomoserine transsulfurase which may utilize cysteine as a sulfur source. More specifically, the protein may be O-acetylhomoserine sulfhydrylase, O-acetylhomoserine transsulfurase, O-succinylhomoserine sulfhydrylase, or O-succinylhomoserine transsulfurase. Therefore, the protein encoded by the *metZ* gene of the present disclosure may be a protein having activity of O-acylhomoserine sulfhydrylase, and specifically, it may be a protein having one or more activities of O-acetylhomoserine sulfhydrylase, O-acetylhomoserine transsulfurase, O-succinylhomoserine sulfhydrylase, and O-succinylhomoserine transsulfurase.

For example, the foreign *metZ* gene of the present disclosure may be a gene derived from those different from the L-methionine-producing microorganism, into which the gene is introduced, or may be different from a gene intrinsically present in the L-methionine-producing microorganism, into which the gene is introduced. Specifically, the gene may be a gene named *metZ* derived from *Chromobacterium violaceum, Hyphomonas neptunium*, or *Rhodobacter sphaeroides*, but is not limited thereto. With respect to the objects of the present disclosure, the gene may include any gene without limitation, as long as it is able to enhance the L-methionine producing ability. A sequence of the *metZ* gene is available from the known database GenBank of NCBI, and as a method of obtaining the corresponding sequence, various methods known in the art are applicable.

In the present disclosure, the protein encoded by the foreign *metZ* may include any one or more selected from the group consisting of polypeptide sequence of SEQ ID NOS: 60, 61, and 62; and amino acid sequences (polypeptide sequences) having 90% or more homology or identity thereto, but is not limited thereto. For example, the protein may include a polypeptide sequence having 91%, 92%, 93%, 94%, 95%, 96%, 97%, 97.5%, 97.7%, 97.8%, 98%, 98.5%, 98.7%, 98.8%, 99%, 99.5%, 99.7%, 99.8%, or less than 100% homology or identity to any one polypeptide sequence of SEQ ID NOS: 60, 61, and 62. For example, the protein may include any one polypeptide sequence of SEQ ID NOS: 66 to 71 and a sequence selected from polypeptide sequences having 90% or more homology or identity thereto, but is not limited thereto.

The *metZ* gene of the present disclosure may include any one or more selected from the group consisting of polynucleotide sequences of SEQ ID NOS: 63, 64, and 65; and a polynucleotide sequence having 90% or more homology or identity thereto, but is not limited thereto. For example, the gene may include any one or more polynucleotide sequences selected from SEQ ID NOS: 63, 64, and 65 and a polynucleotide sequence having 91%, 92%, 93%, 94%, 95%, 96%, 97%, 97.5%, 97.7%, 97.8%, 98%, 98.5%, 98.7%, 98.8%, 99%, 99.5%, 99.7%, 99.8%, or less than 100% homology or identity thereto.

As used herein, the term "polynucleotide" refers to a DNA strand having a predetermined length or more, which is a long chain polymer of nucleotides formed by linking nucleotide monomers via covalent bonds.

In the present disclosure, as long as the *metZ* gene includes a polynucleotide encoding a protein encoded by any one or more polynucleotide sequences selected from SEQ ID NOS: 63, 64, and 65, or a polynucleotide encoding a protein having the efficacy corresponding to the protein having any one or more amino acid sequences of SEQ ID NOS: 60, 61, and 62, it is apparent that any polynucleotide encoding an amino acid sequence, in which part of the sequence is deleted, modified, substituted, or added, may also fall within the scope of the present disclosure.

For example, the *metZ* gene may be a gene encoding an amino acid sequence having substitution of a part, for example, 1 to 20 amino acids in any one amino acid sequences of SEQ ID NOS: 60, 61, and 62. In another embodiment, the *metZ* gene may be a sequence encoding an amino acid sequence having addition of 20, 19, 18, 17, 16, 15, 14, 13, 12, or 11 or fewer amino acid sequences before/after the amino acid sequence. In still another embodiment, the *metZ* gene may be a sequence encoding an amino acid sequence including all the above-described substitution and addition, but is not limited thereto.

Further, a probe which may be produced from a known nucleotide sequence, for example, a polynucleotide which hybridizes with a complementary sequence to all or a part of the polynucleotide sequence under stringent conditions may also be included without limitation.

In other words, although it is described as "a polynucleotide including a nucleotide sequence of a specific sequence number", "a polynucleotide consisting of a nucleotide sequence of a specific sequence number", or "a polynucleotide having a nucleotide sequence of a specific sequence number" in the present disclosure, it is apparent that any polynucleotide encoding an amino acid sequence in which part of the sequence is deleted, modified, substituted, conservatively substituted, or added may be included in the scope of the present disclosure, as long as it has activity the same as or corresponding to that of the polypeptide encoded by the nucleotide sequence consisting of the polynucleotide of the sequence number. For example, it may be a case where the N-terminus and/or C-terminus of the amino acid sequence is added with a sequence that does not alter the function of the protein, a naturally occurring mutation, a silent mutation thereof, or a conservative substitution.

As used herein, the term "conservative substitution" refers to substitution of an amino acid with another amino acid having similar structural and/or chemical properties. Such amino acid substitution may generally occur based on similarity of polarity, charge, solubility, hydrophobicity, hydrophilicity, and/or amphipathic nature of a residue.

As used herein, the term "homology" or "identity" refers to a degree of relatedness between two given nucleotide sequences, and may be expressed as a percentage.

The terms "homology and identity" may be often used interchangeably with each other.

The sequence homology or identity of conserved polynucleotides may be determined by standard alignment algorithms and may be used with a default gap penalty established by the program being used. Substantially, homologous or identical sequences are generally expected to hybridize to all or at least about 50%, 60%, 70%, 80%, or 90% of the entire length of the sequences under moderate or highly stringent conditions. Polynucleotides that contain degenerate codons instead of general codons in hybridizing polynucleotides are also considered.

Whether any two polynucleotide sequences have homology, similarity, or identity may be determined by a known computer algorithm such as the "FASTA" program as in Pearson et al. (1988) *Proc. Natl. Acad. Sci. USA* 85:2444 using default parameters. Alternatively, it may be determined by the Needleman-Wunsch algorithm (Needleman and Wunsch, 1970, *J. Mol. Biol.* 48:443-453), which is performed using the Needleman program of the EMBOSS package (EMBOSS: The European Molecular Biology Open Software Suite, Rice et al., 2000, *Trends Genet.* 16:276-277) (version 5.0.0 or later) (GCG program package (Devereux, J., et al., *Nucleic Acids Research* 12:387 (1984)), BLASTP, BLASTN, FASTA (Atschul, S. F., et al., *J MOLEC BIOL* 215:403 (1990); *Guide to Huge Computers, Martin J. Bishop, ed.*, Academic Press, San Diego, 1994, and CARILLO et al. (1988) *SIAM J Applied Math* 48:1073). For example, the homology, similarity, or identity may be determined using BLAST or ClustalW of the National Center for Biotechnology Information.

The homology, similarity, or identity of polynucleotides may be determined by comparing sequence information using, for example, the GAP computer program, such as Needleman et al. (1970), *J Mol Biol.* 48:443, as disclosed in Smith and Waterman, *Adv. Appl. Math* (1981) 2:482. Briefly, the GAP program defines the homology, similarity, or identity as a value obtained by dividing the number of similarly aligned symbols (i.e., nucleotides or amino acids) by the total number of the symbols in the shorter of the two sequences. Default parameters for the GAP program may include (1) a binary comparison matrix (containing a value of 1 for identities and 0 for non-identities) and the weighted comparison matrix of Gribskov et al. (1986) *Nucl. Acids Res.* 14:6745, as disclosed in Schwartz and Dayhoff, eds., *Atlas Of Protein Sequence And Structure*, National Biomedical Research Foundation, pp. 353-358 (1979) (alternatively, a substitution matrix of EDNAFULL (EMBOSS version of NCBI NUC4.4); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity, or identity with each other may be identified by comparing the sequences in a Southern hybridization experiment under stringent conditions as defined, and appropriate hybridization conditions defined are within the skill of the art, and may be determined by a method well known to those skilled in the art (e.g., J. Sambrook et al., *Molecular Cloning, A Laboratory Manual,* 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

Further, in the polynucleotide of the present disclosure, various modifications may be made in the coding region provided that they do not change the polypeptide sequence, due to codon degeneracy or in consideration of the codons preferred by an organism in which the polynucleotide is to be expressed. Further, a probe that may be prepared from a known gene sequence, for example, any polynucleotide sequence which may hybridize with a sequence complementary to all or part of the nucleotide sequence under stringent conditions, and which may increase an L-methionine productivity, while not being a sequence naturally present in a microorganism into which the sequence is introduced, may be included without limitation. The "stringent conditions" refer to conditions under which specific hybridization between polynucleotides is allowed. Such conditions are specifically described in various literatures (e.g., J. Sambrook et al., *Molecular Cloning, A Laboratory Manual,* 2nd Edition, Cold Spring Harbor Laboratory press, Cold Spring Harbor, New York, 1989), and well known in the art. For example, the stringent conditions may include conditions under which genes having a high homology or identity of 40% or higher, specifically, 70% or higher, 80% or higher, 85% or higher, 90% or higher, more specifically 95% or higher, more specifically 97% or higher, and particularly specifically 99% or higher are hybridized with each other, and genes having a homology or identity lower than the above homologies or identities are not hybridized with each other, or common washing conditions of Southern hybridization, that is, washing once, specifically twice or three times at a salt concentration and a temperature corresponding to 60° C., 1×SSC, 0.1% SDS, specifically 60° C., 0.1×SSC, 0.1% SDS, and more specifically 68° C., 0.1× SSC, 0.1% SDS.

Hybridization requires that two polynucleotides have complementary sequences, although mismatches between bases are possible depending on the stringency of the hybridization. The term "complementary" is used to describe the relationship between nucleotide bases that may hybridize with each other. For example, with respect to DNA, adenosine is complementary to thymine, and cytosine is complementary to guanine. Therefore, the polynucleotide of the present disclosure may include isolated polynucleotide fragments complementary to the entire sequence as well as polynucleotide sequences substantially similar thereto.

Specifically, the polynucleotides having a homology or identity may be detected using the hybridization conditions including a hybridization step at a $T_m$ value of 55° C. under the above-described conditions. Further, the $T_m$ value may be 60° C., 63° C., or 65° C., but is not limited thereto, and may be appropriately adjusted by those skilled in the art depending on the purpose thereof.

Appropriate stringency for the hybridization of polynucleotides depends on the length and degree of complementarity of the polynucleotides, and the variables are well known in the art (see Sambrook et al., supra, 9.50-9.51, 11.7-11.8).

As used herein, the term "protein introduction" means that a microorganism exhibits the activity of a particular protein which was not originally possessed therein, or means that the microorganism exhibits enhanced activity, as compared with its intrinsic activity or the activity of the protein before modification. For example, it may mean that a specific protein is introduced, a polynucleotide encoding the specific protein is introduced into the chromosome of a microorganism, or a vector containing the polynucleotide encoding the specific protein is introduced into the microorganism, thereby allowing its activity to be exhibited. In the present disclosure, the protein introduction may be also expressed as enhancement of protein activity in a microorganism having no particular protein activity.

The protein introduction may be performed by introducing a foreign polynucleotide encoding a protein exhibiting the activity identical/similar to that of the above protein, or by introducing a codon-optimized variant polynucleotide thereof into a host cell. Any foreign polynucleotide sequence may be used without limitation in the origin or sequence thereof, as long as it shows the activity identical/similar to that of the above protein. Further, the foreign polynucleotide may be introduced into the host cell, after optimizing its codons such that optimized transcription and translation may occur in the host cell. The introduction may be carried out by a known transformation method which is appropriately selected by those skilled in the art, and the protein may be produced by expression of the introduced polynucleotide in the host cell, and as a result, its activity may be increased.

Enhancement of activity of the introduced protein may be performed by:

1) increasing the intracellular copy number of a gene or polynucleotide encoding the protein,
2) replacing a gene expression regulatory region on the chromosome encoding the protein with a sequence having a strong activity,
3) modifying a nucleotide sequence of a start codon or 5'-UTR region of the protein,
4) modifying a polynucleotide sequence on the chromosome to increase activity of the protein, or
5) a combination of the methods, but is not limited thereto.

As used herein, the term "vector" refers to a DNA construct containing a target polynucleotide sequence, which is operably linked to a suitable regulatory sequence such that the target gene may be introduced into an appropriate host. The regulatory sequence includes a promoter capable of initiating transcription, any operator sequence for the control of the transcription, a sequence encoding an appropriate mRNA ribosome binding domain, and a sequence regulating the termination of transcription and translation. After being transformed into a suitable host cell, the vector may be replicated or function irrespective of the host genome, and may be integrated into the host genome itself. For example, a target polynucleotide in the chromosome may be replaced with a modified polynucleotide through a vector for chromosomal insertion. The insertion of the polynucleotide into the chromosome may be performed by way of any method known in the art, for example, homologous recombination, but is not limited thereto.

The vector of the present disclosure is not particularly limited, and any vector known in the art may be used. Examples of commonly used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc. may be used, and as a plasmid vector, those based on pBR, pUC, pBluescriptll, pGEM, pTZ, pCL, pET, etc. may be used. Specifically, pDZ, pDCM2, pACYC177, pACYC184, pCL, pECCG117, pUC19, pBR322, pMW118, pCC1 BAC vectors, etc. may be used.

As used herein, the term "transformation" refers to a process of introducing a vector including a polynucleotide encoding a target protein into a host cell, thereby enabling expression of the protein encoded by the polynucleotide in the host cell. As long as the transformed polynucleotide may be expressed in the host cell, it does not matter whether it is inserted into the chromosome of a host cell and located therein or located outside the chromosome, and both cases may be included. Additionally, the polynucleotide includes DNA and RNA which encode the target protein. The polynucleotide may be introduced in any form as long as it may be introduced into a host cell and expressed therein. For example, the polynucleotide may be introduced into a host cell in the form of an expression cassette, which is a gene construct including all elements necessary for self-expression. The expression cassette may generally include a promoter operably linked to the polynucleotide, a transcription terminator, a ribosome binding domain, and a translation terminator. The expression cassette may be in the form of an expression vector capable of self-replication. Additionally, the polynucleotide may be introduced as it is into a host cell and operably linked to a sequence necessary for its expression in the host cell, but is not limited thereto.

Further, as used herein, the term "operably linked" refers to a functional linkage between the above gene sequence and a promoter sequence which initiates and mediates the transcription of the polynucleotide encoding the target protein of the present disclosure.

The method of transforming the vector of the present disclosure includes any method of introducing a nucleic acid into a cell, and may be performed by selecting a suitable standard technique as known in the art depending on the host cell. For example, the method may include electroporation, calcium phosphate ($CaPO_4$) precipitation, calcium chloride ($CaCl_2$) precipitation, microinjection, a polyethylene glycol (PEG) technique, a DEAE-dextran technique, a cationic liposome technique, a lithium acetate-DMSO technique, etc., but is not limited thereto.

The microorganism of the present disclosure may include a wild-type microorganism and a naturally or artificially genetically modified microorganism. Any microorganism, in which the foreign *metZ* gene is introduced or included, as explained in the present disclosure, may be included without limitation.

The microorganism may be an L-methionine-producing microorganism including any one or more of the foreign *metZ* gene of the present disclosure; a protein encoded thereby; and a vector including the *metZ* gene.

As used herein, the term "L-methionine-producing microorganism" includes all of wild-type microorganisms, or naturally or artificially genetically modified microorganisms, and it may be a microorganism in which a particular mechanism is weakened or enhanced due to insertion of a foreign gene, or enhancement or inactivation of the activity of an endogenous gene, and it may be a microorganism including a genetic modification for the production of the desired L-methionine.

The L-methionine-producing microorganism may be a microorganism that includes a protein encoded by the foreign *metZ* gene of the present disclosure to have enhanced L-methionine producing ability, as compared with a parent strain or a non-modified microorganism.

As used herein, the term "strain before modification" or "microorganism before modification" may refer to, not excluding a strain including a mutation which may naturally occur in the microorganism, a wild-type strain or a native-type strain itself, or a strain before changing its trait, which is changed due to genetic variation caused by natural or artificial factors. The "strain before modification" or "microorganism before modification" may be used interchangeably with "non-modified strain", "non-modified type strain", "non-modified microorganism", "non-modified type microorganism" or "reference microorganism". Alternatively, it may be a microorganism, in which expression levels of the genes involved in the L-methionine biosynthetic pathway are not regulated, or a microorganism, into which the *metZ* gene, intrinsically not existing, is not introduced.

The L-methionine-producing microorganism of the present disclosure may be a microorganism having enhanced L-methionine producing ability by enhancing the activity of a part of proteins in the L-methionine biosynthetic pathway or by weakening the activity of a part of proteins in the L-methionine decomposing pathway.

Specifically, examples of the proteins or genes, of which expression may be regulated for enhancing the L-methionine biosynthetic pathway or for attenuating/inactivating the L-methionine decomposing pathway, are as follows: Proteins, representative genes encoding the proteins, and representative EC numbers are described in order. Proteins start with a capital letter and genes are italicized. For example, the L-amino acid biosynthetic pathway may be enhanced or the L-amino acid decomposing pathway may be attenuated by enhancing activity of a part of one or more proteins or systems selected from thiosulfate sulfurtransferase such as Rdl2p, GlpE, PspE, YgaP, ThiI, YbbB, SseA, YnjE, YceA, YibN, NCg0671, NCgl1369, NCgl2616, NCg0053, NCg0054, NCG12678, NCgl2890, etc.; sulfite reductase, cysI; thiosulfate/sulfate transport system, cysPUWA (EC 3.6.3.25); 3'-phosphoadenosine 5'-phosphosulfate reductase, cysH (EC 1.8.4.8); sulfite reductase, cysJI (EC 1.8.1.2); cysteine synthase A, cysK (EC 2.5.1.47); cysteine synthase B, cysM (EC 2.5.1.47); serine acetyltransferase, cysE (EC 2.3.1.30); a glycine cleavage system, gcvTHP-lpd (EC 2.1.2.10, EC 1.4.4.2, EC 1.8.1.4); lipoyl synthase, lipA (EC 2.8.1.8); lipoyl protein ligase, lipB (EC 2.3.1.181); phosphoglycerate dehydrogenase, serA (EC 1.1.1.95); 3-phosphoserine phosphatase, serB (EC 3.1.3.3); 3-phosphoserine/phosphohydroxythreonine aminotransferase, serC (EC 2.6.1.52); serine hydroxymethyltransferase, glyA (EC 2.1.2.1); aspartokinase I (EC 2.7.2.4); homoserine dehydrogenase 1, thrA (EC 1.1.1.3); aspartate kinase, lysC (EC 2.7.2.4); homoserine dehydrogenase, hom (EC 1.1.1.3); homoserine O-acetyltransferase, metX (EC 2.3.1.31); homoserine O-succinyltransferase, metA (EC 2.3.1.46); cystathionine gamma-synthase, metB (EC 2.5.1.48); β-C—S-lyase, aecD (EC 4.4.1.8, beta-lyase); cystathionine beta-lyase, metC (EC 4.4.1.8); B12-independent homocysteine S-methyltransferase, metE (EC 2.1.1.14); methionine synthase, metH (EC 2.1.1.13); methylenetetrahydrofolate reductase, metF (EC 1.5.1.20); L-methionine exporter BrnFE; valine exporter YgaZH (B2682, B2683), ygaZH(b2682. b2683); exporter YjeH,b4141; pyridine nucleotide transhydrogenase PntAB, pntAB (EC 1.6.1.2); and phosphoenolpyruvate carboxylase, Pyc (EC 4.1.1.31), or by overexpressing polynucleotides encoding the same. Alternatively, activity of one or more proteins selected from the group consisting of glucose 6-phosphate isomerase, pgi (EC 5.3.1.9); homoserine kinase, thrB (EC 2.7.1.39); S-adenosyl methionine synthase, metK (EC 2.5.1.6); dihydrodipicolinate synthase, dapA (EC 4.2.1.52); phosphoenolpyruvate carboxykinase, pck (EC 4.1.1.49); formyltetrahydrofolate hydrolase, purU (EC 3.5.1.10); pyruvate kinase 1, pykF (EC 2.7.1.40); pyruvate kinase 1l, pykA (EC 2.7.1.40); cystathionine γ-lyase, cg3086 (EC 4.4.1.1); cystathionine R-synthase, cg2344 (EC 4.2.1.22); regulatory protein Cg3031, cg3031; methionine and cysteine biosynthesis repressor protein McbR, mcbR; L-methionine (Met) transcriptional repressor protein, metJ; L-methionine transporter MetQNI, metQ, metN, metI; N-acyltransferase, yncA; sRNA fnrS; and L-methionine transporter, metP may be inactivated or attenuated, or expression of genes encoding the proteins may be suppressed or eliminated.

In one specific embodiment, the L-methionine-producing microorganism of the present disclosure may include, in addition to the introduction of *metZ*, one or more genetic modifications selected from the group consisting of attenuation or inactivation of activity of cystathionine gamma synthase; attenuation or inactivation of activity of O-acetyl-homoserine sulfhydrylase; attenuation or inactivation of activity of methionine-cysteine biosynthesis repressor protein; enhancement of activity of methionine synthase; and enhancement of activity of sulfite reductase. Alternatively, the genetic modification may include one or more modifications selected from the group consisting of deletion/expression inhibition of the metB gene; deletion of the metY gene; deletion/expression inhibition of the mcbR gene; and expression enhancement of metH and cysI gene. For example, the metB gene, the metY gene, the mcbR gene, the metH gene, and the cysI gene may include a polynucleotide sequence at least 70%, 75%, 80%, 85%, 86%, 87%, 88%, 89%, 90%, 91%, 92%, 93%, 94%, 95%, 96%, 97%, 98%, or 99% homology or identity to a polynucleotide sequence of SEQ ID NO: 25, SEQ ID NO: 26, SEQ ID NO: 1, SEQ ID NO: 39, and SEQ ID NO: 40, respectively, but are not limited thereto. The above description regarding homology or identity is also applied to the metB, metY, mcbR, metH, and cysI genes.

However, the genes are merely one example, and are not limited thereto, and the microorganism may be a microorganism, in which activity of various known proteins of the L-methionine biosynthetic pathways is enhanced or activity of proteins of the L-methionine decomposing pathways is inactivated or attenuated.

As used herein, the term "enhancement" of activity of a polypeptide or protein means that that activity of a polypeptide or protein is increased, as compared with its intrinsic activity. The enhancement may be used interchangeably with the term "up-regulation", "overexpression", "increase", etc. Herein, the increase may include all of exhibiting activity not originally possessed or exhibiting improved activity, as compared with intrinsic activity or activity before modification. The term "intrinsic activity" means the activity of a particular polypeptide or protein originally possessed by a parent strain before transformation or a non-modified microorganism, when a trait is changed due to genetic modification caused by a natural or artificial factor. This may be used interchangeably with the term "activity before modification". "The activity of a polypeptide or protein is enhanced or increased, as compared with the intrinsic activity" means that the activity is improved, as compared with the activity of a particular polypeptide or protein originally possessed by a parent strain before transformation or a non-modified microorganism. The "increase of activity" may be achieved by introducing a foreign polypeptide or protein or by enhancing activity of the intrinsic polypeptide or protein, specifically, by enhancing activity of the intrinsic polypeptide or protein. Whether or not the activity of the polypeptide or protein is enhanced may be identified by the degree of activity of the corresponding polypeptide or protein, the expression level thereof, or the increase in the amount of a product from the corresponding protein.

Various methods well known in the art may be applied to the enhancement of the activity of the polypeptide or protein, and the method is not limited, as long as it is able to enhance the activity of the desired polypeptide or protein, as compared with that of the microorganism before modification. The method may be, but is not limited to, a method of using genetic engineering and/or protein engineering well known to those skilled in the art, which is a routine method of molecular biology (Sitnicka et al. "Functional Analysis of Genes". *Advances in Cell Biology*. 2010, Vol. 2. 1-16; Sambrook et al. *Molecular Cloning* 2012; etc.).

The method of enhancing the activity of the polypeptide or protein using genetic engineering may be performed by, for example, 1) a method of increasing the intracellular copy number of a gene or polynucleotide encoding the polypeptide or protein;

2) a method of replacing a gene expression regulatory region on the chromosome encoding the polypeptide or protein with a sequence having a strong activity, 3) a method of modifying a nucleotide sequence of a start codon or 5'-UTR region of the polypeptide or protein, 4) a method of modifying a polynucleotide sequence on the chromosome to increase the activity of the polypeptide or protein, 5) a method of introducing a foreign polynucleotide exhibiting the activity of the polypeptide or protein, or introducing a variant polynucleotide by codon-optimization of the polynucleotide, or 6) a combination of the methods, but is not limited thereto.

The method of enhancing the activity of the polypeptide or protein using protein engineering may be performed by, for example, a method of analyzing a tertiary structure of the polypeptide or protein, choosing an exposed site thereof, and then changing or chemically modifying the site, but is not limited thereto.

1) The method of increasing the intracellular copy number of a gene or polynucleotide encoding the polypeptide or protein may be performed by any method known in the art, for example, by introducing, into a host cell, a vector which is operably linked with the gene or polynucleotide encoding the corresponding polypeptide or protein and is able to replicate and function regardless of the host cell. Alternatively, it may be performed by introducing, into a host cell, a vector which is operably linked with the gene and is able to insert the gene or polynucleotide into the chromosome of the host cell, but is not limited thereto. The vector is the same as described above.

2) The method of replacing a gene expression regulatory region (or expression regulatory sequence) on the chromosome encoding the polypeptide or protein with a sequence having a strong activity may be performed by any method known in the art, for example, by inducing a mutation on the sequence by deletion, insertion, non-conservative or conservative substitution of the nucleotide sequence, or a combination thereof to further enhance the activity of the expression regulatory region, or by replacing the sequence with a nucleotide sequence having a stronger activity. The expression regulatory region may include, but is not particularly limited to, a promoter, an operator sequence, a sequence encoding a ribosome-binding site, a sequence regulating termination of transcription and translation, etc. The method may specifically link a strong heterologous promoter instead of the original promoter, but is not limited thereto.

Examples of the known strong promoter may include cj1 to cj7 promoters (U.S. Pat. No. 7,662,943 B2), a lac promoter, a trp promoter, a trc promoter, a tac promoter, a lambda phage PR promoter, a PL promoter, a tet promoter, a gapA promoter, an SPL7 promoter, an SPL13(sm3) promoter (U.S. Pat. No. 10,584,338 B2), an O2 promoter (U.S. Pat. No. 10,273,491 B2), a tkt promoter, an yccA promoter, etc., but are not limited thereto.

3) The method of modifying a nucleotide sequence of a start codon or 5'-UTR region of the polypeptide or protein may be performed by any method known in the art, for example, by replacing the intrinsic start codon of the polypeptide or protein with another start codon having a higher expression rate of the polypeptide or protein than the intrinsic start codon, but is not limited thereto.

4) The method of modifying a polynucleotide sequence on the chromosome to increase the activity of the polypeptide or protein may be performed by any method known in the art, for example, by inducing a mutation on the expression regulatory sequence by deletion, insertion, non-conservative or conservative substitution of the nucleotide sequence, or a combination thereof to further enhance the activity of the polynucleotide sequence, or by replacing the sequence with a polynucleotide sequence which is improved to have a stronger activity. The replacing may be specifically inserting the gene into the chromosome by homologous recombination, but is not limited thereto.

A vector which may be used herein may further include a selection marker to identity the insertion into the chromosome. The selection marker is the same as described above.

5) The method of introducing a foreign polynucleotide exhibiting the activity of the polypeptide or protein may be performed by any method known in the art, for example, by introducing, into a host cell, a foreign polynucleotide encoding a polypeptide or protein which exhibits activity identical/similar to that of the polypeptide or protein, or a codon-optimized variant polynucleotide thereof. Any foreign polynucleotide may be used without limitation in its origin or sequence, as long as it exhibits activity identical/similar to that of the polypeptide or protein. Further, the foreign polynucleotide may be introduced into the host cell after being codon-optimized so that the optimized transcription and translation thereof occur in the host cell. The introduction may be performed by a known transformation method which is appropriately selected by those skilled in the art, and the polynucleotide introduced into the host cell is expressed to produce the polypeptide or protein, and as a result, its activity may be increased.

Lastly, 6) a combination of the methods may be performed by applying any one or more methods of 1) to 5).

Such enhancement of the activity of the polypeptide or protein may be an increase in the activity or concentration of the corresponding polypeptide or protein, based on the activity or concentration of the polypeptide or protein expressed in the wild-type strain or the microorganism strain before modification, or an increase in the amount of a product produced from the corresponding polypeptide or protein, but is not limited thereto.

As used herein, the term "inactivation" or "attenuation" of a polypeptide or protein is a concept including all of the cases where activity is reduced or activity is absent, as compared with the intrinsic activity. The inactivation or attenuation may be used interchangeably with the term "down-regulation", "decrease", "reduction", etc. The inactivation or attenuation may also include the case where the activity of the protein itself is reduced or removed due to mutation in a gene encoding the protein, etc., as compared with activity of the protein originally possessed by the microorganism, the case where the overall level of intracellular protein activity is lower than that of the native strain, due to expression inhibition or translation inhibition of the gene encoding the protein, the case where expression of the gene does not occur at all, and the case where the protein exhibits no activity, even though expressed. The term "intrinsic activity" means the activity of a particular polypeptide or protein originally possessed by a parent strain before transformation or a non-modified microorganism, when a trait is changed due to genetic modification caused by a natural or artificial factor. This may be used interchangeably with the term "activity before modification". "The activity of a polypeptide or protein is decreased, as compared with the intrinsic activity" means that the activity is decreased, as compared with the activity of a particular polypeptide or protein originally possessed by a parent strain before transformation or a non-modified microorganism.

The inactivation or attenuation of the activity of the protein may be achieved by, but is not limited to, various methods well known in the art (Nakashima N et al., "Bacterial cellular engineering by genome editing and gene silencing". *Int J Mol Sci.* 2014; 15(2):2773-2793; Sambrook et al. *Molecular Cloning* 2012; etc.).

Examples of the method may include
1) a method of deleting all or a part of the gene encoding the protein;
2) a method of modifying the expression regulatory region (or expression regulatory sequence) such that the expression of the gene encoding the protein is decreased;
3) a method of modifying the gene sequence encoding the protein such that the protein activity is removed or weakened;
4) a method of introducing an antisense oligonucleotide (e.g., antisense RNA) that binds complementarily to a transcript of the gene encoding the protein;
5) a method of adding a complementary sequence to the Shine-Dalgarno sequence upstream of the Shine-Dalgarno sequence of the gene encoding the protein to form a secondary structure, thereby inhibiting the ribosomal binding; and
6) a reverse transcription engineering (RTE) method of adding a promoter at the 3' terminus of an open reading frame (ORF) of the polynucleotide sequence of the gene encoding the protein so as to be reversely transcribed, and the method may be achieved by a combination thereof, but is not particularly limited thereto.

Specifically, the method of deleting a part or all of the gene encoding the protein may be executed by replacing the polynucleotide encoding the endogenous desired protein within the chromosome with a polynucleotide having a partially deleted nucleotide sequence or a marker gene, via a vector for chromosomal insertion into the microorganism. The method of deleting a part or all of the polynucleotide may be exemplified by a method of deleting the polynucleotide by homologous recombination, but is not limited thereto.

Further, the method of deleting a part or all of the gene may be performed by inducing a mutation using light such as UV or a chemical and then selecting, from the obtained mutant, a strain in which the target gene is deleted. The method of deleting the gene includes a method by a DNA recombination technology. The DNA recombination technology may be performed by, for example, injecting a nucleotide sequence or vector including a nucleotide sequence having homology to the target gene into the microorganism to induce homologous recombination. In addition, the nucleotide sequence or vector to be injected may include a dominant selection marker, but is not limited thereto.

In addition, the method of modifying the expression regulatory sequence may be achieved by applying various methods well known in the art. Examples of the method may be performed by inducing a mutation on the expression regulatory region (or expression regulatory sequence) by deletion, insertion, non-conservative or conservative substitution of the polynucleotide sequence, or a combination thereof to further attenuate the activity of the expression regulatory region (or expression regulatory sequence), or by replacing the sequence with a polynucleotide sequence having a weaker activity. The expression regulatory region may include a promoter, an operator sequence, a sequence encoding a ribosome-binding site, a sequence regulating termination of transcription and translation, etc., but is not limited thereto.

In addition, the method of modifying the gene sequence may be performed by inducing a mutation on the sequence by deletion, insertion, non-conservative or conservative substitution of the gene sequence, or a combination thereof to further attenuate the activity of the polypeptide, or by replacing the sequence with a gene sequence which is improved to have a weaker activity or with a gene sequence which is improved to have no activity, but is not limited thereto.

For example, expression of the gene may be suppressed or attenuated by introducing a mutation into the gene sequence to form a stop codon.

However, the above-described method is merely an example, and methods of enhancing or inactivating the protein activity and gene manipulation methods are known in the art, and therefore, the L-methionine-producing microorganism may be prepared by applying various known methods.

The microorganism of the present disclosure may be a microorganism of the genus *Corynebacterium*.

In the present disclosure, the "microorganism of the genus *Corynebacterium*" may include all microorganisms of the genus *Corynebacterium*, specifically *Corynebacterium glutamicum*, *Corynebacterium crudilactis*, *Corynebacterium deserti*, *Corynebacterium efficiens*, *Corynebacterium callunae*, *Corynebacterium stationis*, *Corynebacterium singulare*, *Corynebacterium halotolerans*, *Corynebacterium striatum*, *Corynebacterium ammoniagenes*, *Corynebacterium pollutisoli*, *Corynebacterium imitans*, *Corynebacterium testudinoris*, or *Corynebacterium flavescens*, and more specifically *Corynebacterium glutamicum*.

The medium and other culture conditions used for culturing the microorganism of the present disclosure may be any medium commonly used for culturing microorganisms of the genus *Corynebacterium* without any particular limitation. Specifically, the microorganism of the present disclosure may be cultured under aerobic or anaerobic conditions in a common medium containing an appropriate carbon source, nitrogen source, phosphorus source, inorganic compound, amino acid, and/or vitamin, etc., while adjusting temperature, pH, etc.

In the present disclosure, the carbon source may include carbohydrates, such as glucose, fructose, sucrose, maltose, etc.; carbohydrates, such as glucose, fructose, sucrose, maltose, etc.; sugar alcohols such as mannitol, sorbitol, etc.; organic acids such as pyruvic acid, lactic acid, citric acid, etc.; amino acids such as glutamic acid, methionine, lysine, etc. Additionally, natural organic nutrients, such as starch hydrolysate, molasses, blackstrap molasses, rice bran, cassava, sugar cane molasses, corn steep liquor, etc., may be used, and specifically, carbohydrates such as glucose, sterilized pretreated molasses (i.e., molasses converted to reducing sugar) may be used. In addition, an appropriate amount of various other carbon sources may be used without limitation. These carbon sources may be used alone or in a combination of two or more kinds thereof, but are not limited thereto.

The nitrogen source may include inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more kinds thereof, but are not limited thereto.

The phosphorus source may include monopotassium phosphate, dipotassium phosphate, or corresponding sodium-containing salts, etc. The inorganic compound may include sodium chloride, calcium chloride, iron chloride, magnesium sulfate, iron sulfate, manganese sulfate, calcium carbonate, etc.

The sulfur source may include alkanesulfonate, such as methanesulfonate and ethanesulfonate, organic and inorganic sulfur-containing compounds such as sulfate, sulfite, hydrogen sulfide such as $H_2S$, sulfide, sulfide derivatives, a mixture of an organic and inorganic sulfur-containing compound and thiosulfate, such as thioglycolate, thiocyanate and/or thiourea, or the sulfur source may not include substances other than thiosulfate, but is not limited thereto.

The method of producing L-methionine of the present disclosure may include culturing the microorganism in a medium containing thiosulfate. Specifically, the microorganism of the present disclosure may be a microorganism including foreign *metZ* and utilizing thiosulfate as a sulfur source. The thiosulfate may be used as a sulfur source of the microorganism, but is not limited thereto.

As the inorganic compound, sodium chloride, calcium chloride, iron chloride, calcium carbonate, etc. may be used. In addition, the medium may include vitamins and/or appropriate precursors, etc. The medium or precursor may be added to a culture medium in a batch or continuous manner, but is not limited thereto.

In the present disclosure, the pH of a culture medium may be adjusted during the culture of the microorganism by adding a compound such as ammonium hydroxide, potassium hydroxide, ammonia, phosphoric acid, sulfuric acid, etc. to the culture medium in an appropriate manner. Further, during the culture, an antifoaming agent such as a fatty acid polyglycol ester may be added to prevent foam generation. In addition, oxygen or oxygen-containing gas may be injected into the culture medium in order to maintain an aerobic state of the culture medium; or no gas may be injected or nitrogen, hydrogen, or carbon dioxide gas may be injected into the culture medium in order to maintain an anaerobic or microaerobic state, but is not limited thereto.

The temperature of the culture medium may be 25° C. to 40° C., and more specifically, 28° C. to 37° C., but is not limited thereto. The culture may be continued until the useful materials are obtained in desired amounts, and specifically for 1 hour to 100 hours, but is not limited thereto.

The method of producing methionine of the present disclosure may include recovering L-methionine from the microorganism or medium.

The target sulfur-containing amino acids or sulfur-containing amino acid derivatives may be recovered from the medium using a suitable method known in the art according to the method of culturing the microorganism of the present disclosure, for example, a batch, continuous, or fed-batch culture method. For example, methods such as centrifugation, filtration, treatment with a protein crystallization precipitant (salting-out method), extraction, sonication, ultrafiltration, dialysis, various kinds of chromatography such as molecular sieve chromatography (gel filtration), adsorption chromatography, ion-exchange chromatography, affinity chromatography, etc., and HPLC may be used alone or in combination, but the methods are not limited thereto.

The method may include an additional purification process. In the purification process, an appropriate purification method known in the art may be used.

Still another aspect of the present disclosure provides a composition for producing L-methionine, the composition including the microorganism and thiosulfate.

The composition of the present disclosure may further include any suitable excipients commonly used in compositions for producing L-methionine, and these excipients may include, for example, preservatives, wetting agents, dispersing agents, suspending agents, buffering agents, stabilizing agents, isotonic agents, etc., but is not limited thereto.

Still another aspect of the present disclosure provides a method of preparing the L-methionine-producing microorganism, the method including the step of introducing, into the microorganism, the protein encoded by the foreign *metZ* gene.

Still another aspect of the present disclosure provides use of the microorganism, into which the protein encoded by the foreign *metZ* gene is introduced, in the production of L-methionine.

The microorganism, the foreign *metZ* gene and the protein encoded thereby, and the introduction of the protein are the same as described above.

Hereinafter, the present disclosure will be described in more detail with reference to exemplary embodiments. However, these exemplary embodiments are for illustrative purposes only, and the scope of the present disclosure is not intended to be limited by these exemplary embodiments.

Reference Example 1: Preparation of Plasmid

A plasmid (pDCM2, FIG. 1, SEQ ID NO: 81) was designed for gene insertion and replacement in the *Corynebacterium* chromosome, and the plasmid was synthesized using the gene-synthesis service of Bionics Co. The plasmid was designed to include a restriction enzyme that is easy to use for cloning, with reference to a paper regarding the generally known sacB system (Gene, 145 (1994) 69-73). The pDCM2 plasmid thus synthesized has the following characteristics:

1) self-replication is possible in *E. coli*, but self-replication is impossible in *Corynebacterium*, because it has a replication origin that works only in *E. coli*;
2) the pDCM2 plasmid has a kanamycin resistance gene as a selection marker;
3) the pDCM2 plasmid has a Levan sucrose gene (sacB) as a secondary positive-selection marker; and
4) the pDCM2 plasmid does not leave any gene information derived therefrom in the finally prepared strain.

Example 1: Preparation of Recombinant Vector for Deletion of mcbR Gene

In this example, to prepare a methionine-producing strain, a wild-type ATCC13032 strain was used to prepare a vector for inactivating mcbR encoding a methionine-cysteine biosynthesis repressor protein previously disclosed (*J. Biotechnol.* 103:51-65, 2003).

In detail, to delete the mcbR gene on the chromosome of *Corynebacterium* ATC 3032, a recombinant plasmid vector was prepared by way of the following method. Based on nucleotide sequences reported in GenBank of the U.S. National Institutes of Health (NIH), the mcbR gene and its surrounding sequence (SEQ ID NO: 1) of *Corynebacterium glutamicum* were obtained.

For the purpose of obtaining the deleted mcbR gene, PCR was carried out with the chromosomal DNA of *Corynebacterium glutamicum* ATC 3032 as a template using primers of SEQ ID NO: 2 and SEQ ID NO: 3, and SEQ ID NO: 4 and SEQ ID NO: 5 (Table 1).

TABLE 1

| SEQ ID NO | Sequence (5'-3') |
|---|---|
| 2 | TCGAGCTCGGTACCCCTGCCTGGTTTGTCTTGTA |
| 3 | CGGAAAATGAAGAAAGTTCGGCCACGTCCTTTCGG |
| 4 | AGGACGTGGCCGAACTTTCTTCATTTTCCGAAGGG |
| 5 | CTCTAGAGGATCCCCGTTTCGATGCCCACTGAGCA |

PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes. As a result, DNA fragments of 700 bp were obtained, respectively.

A pDCM2 vector not replicable in *Corynebacterium glutamicum*, and the amplified mcbR gene fragments were treated with a restriction enzyme, smal, for chromosomal introduction. After an isothermal assembly cloning reaction, a product was then transformed to *E. coli* DH5α, followed by smearing the same on an LB solid medium containing kanamycin (25 mg/L). Colonies transformed with the vector, in which deleted fragments of the target genes were inserted, were selected through PCR, and a plasmid was obtained using a plasmid extraction method, which was then named pDCM2-ΔmcbR.

Example 2: Preparation and Culture of mcbR Gene-Deleted Strain

ATCC13032 strain was transformed by homologous recombination on the chromosome with the pDC-ΔmcbR vector prepared in Example 1 by electroporation (van der Rest et al., *Appl Microbiol Biotechnol* 52:541-545, 1999).

Thereafter, secondary recombination was carried out on a solid medium containing sucrose. The transformed *Corynebacterium glutamicum* strain, in which the secondary recombination had been completed, was subjected to PCR using SEQ ID NOS: 6 and 7 (Table 2) to identify a strain in which the mcbR gene was deleted. This recombinant strain was named *Corynebacterium glutamicum* CM02-0618.

This CM02-0618 was deposited at the Korean Culture Center of Microorganisms, an international depositary, on Jan. 4, 2019, under the provisions of the Budapest Treaty and assigned Accession No. KCCM12425P.

TABLE 2

| SEQ ID NO | Sequence (5'-3') |
| --- | --- |
| 6 | AATCTGGATTTCCGCCAGGT |
| 7 | CTTCCTAACTCCTGAGGAAG |

In order to analyze the L-methionine producing ability of the prepared CM02-0618, the strain was cultured together with its parent strain, *Corynebacterium glutamicum* ATCC13032 strain, in the following manner.

*Corynebacterium glutamicum* ATCC13032 and *Corynebacterium glutamicum* CM02-0618 of the present disclosure were inoculated into a 250 mL corner-baffled flask containing 25 mL of a medium below, respectively, and then cultured with shaking at 30° C. at 200 rpm for 20 hours. Thereafter, 1 mL of the seed culture medium was inoculated into a 250 mL corner-baffled flask containing 24 mL of a production medium, and then cultured with shaking at 30° C. at 200 rpm for 48 hours. The compositions of the seed medium and production medium are as follows. In the production medium, $(NH_4)_2S_2O_3$, which is a kind of thiosulfate, was used as a sulfur source.

<Seed Medium (pH 7.0)> glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium pantothenate 2000 μg, nicotinamide 2000 μg (based on 1 L of distilled water)

<Production Medium (pH 8.0)> glucose 50 g, $(NH_4)_2S_2O_3$ 12 g, yeast extract 5 g, $KH_2PO_4$ 1 g, $MgSO_4 \cdot 7H_2O$ 1.2 g, biotin 100 μg, thiamine HCl 1000 μg, calcium pantothenate 2000 μg, nicotinamide 3000 μg, $CaCO_3$ 30 g, cyanocobalamin (Vitamin B12) 1 μg (based on 1 L of distilled water)

After culturing by the above culture method, the concentration of L-methionine in the culture medium was analyzed and shown in Table 3 below.

TABLE 3

| Verification of L-methionine producing ability of wild-type and mcbR-deleted strains | |
| --- | --- |
| Strain | L-Methionine (g/L) |
| *Corynebacterium glutamicum* ATCC13032 (wild-type) | 0.00 |
| CM02-0618 | 0.04 |

As a result, in the strain, in which mcbR alone was removed, L-methionine production was observed.

Example 3-1: Preparation of Vectors for Introduction of Three Foreign *metZ* Genes An attempt was made to compensate for the shortcomings of the existing methionine biosynthesis method while enhancing methionine production by introducing foreign *metZ* into *Corynebacterium* strain. In detail, vectors for introducing *metZ* derived from *Chromobacterium violaceum, Hyphomonas neptunium, Rhodobacter sphaeroides* were prepared.

In detail, recombinant plasmid vectors were prepared by way of the following methods in order to additionally insert each of three kinds of foreign *metZ* genes into the chromosome of *Corynebacterium* ATC 3032.

First, in order to insert *metZ*, a vector for removing Ncgl1021 (Transposase) was prepared. Based on nucleotide sequences reported in GenBank of the U.S. National Institutes of Health (NIH), Ncgl1021 and its surrounding sequence (SEQ ID NO: 8) of *Corynebacterium glutamicum* were obtained. For the purpose of obtaining the deleted Ncgl1021 gene, PCR was carried out with the chromosomal DNA of *Corynebacterium glutamicum* ATCC13032 as a template using primers of SEQ ID NO:9 and SEQ ID NO: 10, and SEQ ID NO: 11 and SEQ ID NO: 12 (Table 4).

TABLE 4

| SEQ ID NO | Sequence (5'-3') |
| --- | --- |
| 9 | ACCCGGGGATCCTCTAGAATGTTTGTGATGCGCAG |
| 10 | GTCAGAGAGTACTTACGCTGATCGGGAGGGAAAGC |
| 11 | ATCAGCGTAAGTACTCTCTGACTAGCGTCACCCTC |
| 12 | CTGCAGGTCGACTCTAGAAAAGGGATTGGAGTGTT |

PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes. As a result, DNA fragments were obtained, respectively. A pDCM2 vector not replicable in *Corynebacterium glutamicum*, and the amplified Ncgl1021 gene fragments were treated with a restriction enzyme, smal, for chromosomal introduction. After an isothermal assembly cloning reaction, a product was then transformed to *E. coli* DH5α, followed by smearing the same on an LB solid medium containing kanamycin (25 mg/L). Colonies transformed with the vector, in which deleted fragments of the target genes were inserted, were selected through PCR, and a plasmid was obtained using a plasmid extraction method, which was then named pDCM2-ΔNcgl1021.

For the purpose of obtaining the *metZ* genes (derived from *Chromobacterium violaceum, Hyphomonas neptunium*, and *Rhodobacter sphaeroides*), PCR was carried out with each chromosomal DNA of *Chromobacterium violaceum, Hyphomonas neptunium*, and *Rhodobacter sphaeroides* as a template using primers of SEQ ID NOS: 13 and 14, SEQ ID NOS: 15 and 16, and SEQ ID NOS: 17 and 18. To express the three kinds of *metZ* genes, respectively, a Pspl1 promoter was used, and Pspl1 was subjected to PCR using the previously disclosed spl1-GFP (KR 10-1783170 B1) vector DNA as a template and primers of SEQ ID NOS: 19 and 20, SEQ ID NOS: 19 and 21, SEQ ID NOS: 19 and 22 (Table 5). PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes.

TABLE 5

| SEQ ID NO | Sequence (5'-3') |
| --- | --- |
| 13 | ATCAAAACAGATATCATGGCATCCGACGCGCCGCA |
| 14 | CGCTAGTCAGAGAGTTTAGTCAAGGCCCCGCAACA |
| 15 | ATCAAAACAGATATCATGGCGGATGCACCCGGCGG |

TABLE 5-continued

| SEQ ID NO | Sequence (5'-3') |
|---|---|
| 16 | CGCTAGTCAGAGAGTTCACAAGCTGTTAAGCGAAG |
| 17 | ATCAAAACAGATATCATGACGAAGGACTGGAAGAC |
| 18 | CGCTAGTCAGAGAGTTCAGATCACCGCGAGCGCCT |
| 19 | CCGATCAGCGTAAGTGGCGCTTCATGTCAACAATC |
| 20 | CGCGTCGGATGCCATGATATCTGTTTTGATCTCCT |
| 21 | GGGTGCATCCGCCATGATATCTGTTTTGATCTCCT |
| 22 | CCAGTCCTTCGTCATGATATCTGTTTTGATCTCCT |

As a result, the three kinds of foreign *metZ* gene fragments (SEQ ID NOS: 63 to 65) and respective spl1 promoter fragments for expressing the three kinds of *metZ* genes were obtained, respectively. A pDCM2-ΔNcgl1021 vector not replicable in *Corynebacterium glutamicum* was treated with a restriction enzyme, scal. After an isothermal assembly cloning reaction of the amplified spl1 promoter fragments with the *metZ* fragments according to each strain, each product was then transformed to *E. coli* DH5α, followed by smearing the same on an LB solid medium containing kanamycin (25 mg/L). Colonies transformed with the vector, in which the target gene was inserted, were selected through PCR, and a total of three kinds of plasmids were obtained using a plasmid extraction method, which were then named pDCM2-ΔNcgl1021-PsplCvimetZ (*Chromobacterium violaceum metZ*), pDCM2-ΔNcgl1021-PsplHnemetZ (*Hyphomonas neptunium metZ*), and pDCM2-ΔNcgl1021-PsplRspmetZ (*Rhodobacter sphaeroides metZ*), respectively.

Example 3-2: Preparation of Vector for Introduction of *metZ* Gene

Vectors for sequences of six *metZ* genes derived from *Rhodobacter sphaeroides*, previously known, were additionally prepared. In the same manner as in Example 3-1 (see US 2013-0273614 A1 and US 2018-0355389 A1), vectors, into which *metZ* genes each encoding the amino acid sequences of SEQ ID NOS: 66 to 71 were prepared, respectively. The *metZ* genes were named RspmetZ_long, RspmetZ_3, RspmetZ_65, RspmetZ_104, RspmetZ_196, and RspmetZ_3_65_104, respectively, and primers used for introducing each gene are as follows.

TABLE 6

| | Primer | Sequence (5'-3') |
|---|---|---|
| RspmetZ | SEQ ID NO: 72 | ATCAAAACAGATATCATG GGTATCGCGTTTCGTGA |
| RspmetZ_3 | SEQ ID NO: 73 | CCTTCACGAAACGCGtTA CCCATGATATCTG |
| RspmetZ_3 | SEQ ID NO: 74 | CAGATATCATGGGTAaCG CGTTTCGTGAAGG |
| RspmetZ_65 | SEQ ID NO: 75 | TAGCGGGCATAGATGtAT TCGTCGGCGCCGG |
| RspmetZ_65 | SEQ ID NO: 76 | CCGGCGCCGACGAATaCA TCTATGCCCGCTA |
| RspmetZ_104 | SEQ ID NO: 77 | ACGATCGAGGTGAGCgCG CCGTGGATCGCGG |

TABLE 6-continued

| | Primer | Sequence (5'-3') |
|---|---|---|
| RspmetZ_104 | SEQ ID NO: 78 | CCGCGATCCACGGCGCGC TCACCTCGATCGT |
| RspmetZ_196 | SEQ ID NO: 79 | CGGGCGTCGCGAAGAtAT TGTCCACGATGAC |
| RspmetZ_196 | SEQ ID NO: 80 | GTCATCGTGGACAATaTC TTCGCGACGCCCG |

First, for the purpose of obtaining the RspmetZ_long, PCR was carried out with the chromosomal DNA of *Rhodobacter sphaeroides* using primers of SEQ ID NOS: 19 and 22, and SEQ ID NOS: 72 and 18.

As a result, the gene fragment and spl1 promoter fragment were obtained.

A pDCM2-ΔNcgl1021 vector not replicable in *Corynebacterium glutamicum* was treated with a restriction enzyme, scal. After an isothermal assembly cloning reaction of the amplified spl1 promoter fragments with the *metZ* fragments according to each strain, each product was then transformed to *E. coli* DH5α, followed by smearing the same on an LB solid medium containing kanamycin (25 mg/L). Colonies transformed with the vector, in which the target gene was inserted, were selected through PCR, and a plasmid was obtained using a plasmid extraction method, which was then named pDCM2-ΔNcgl1021-PsplRspmetZ_long.

For the purpose of obtaining the RspmetZ_3, RspmetZ_65, RspmetZ_104, RspmetZ_196, and RspmetZ_3_65_104, PCR was carried out with the pDCM2-ΔNcgl1021-PsplRspmetZ_long vector as a template using SEQ ID NOS: 72 and 73, 74 and 18 (RspmetZ_3), SEQ ID NOS: 72 and 75, 76 and 18 (RspmetZ_65), SEQ ID NOS: 72 and 77, 78 and 18 (RspmetZ_104), SEQ ID NOS: 71 and 79, 80 and 18 (RspmetZ_196), SEQ ID NOS: 72 and 73, 74 and 75, 76 and 77, 77 and 18 (RspmetZ_3_65_104). PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes.

As a result, a total of ten fragments were obtained.

TABLE 7

| | |
|---|---|
| Fragment 1 | SEQ ID NOS: 72, 73 |
| Fragment 2 | SEQ ID NOS: 74, 18 |
| Fragment 3 | SEQ ID NOS: 72, 75 |
| Fragment 4 | SEQ ID NOS: 76, 18 |
| Fragment 5 | SEQ ID NOS: 72, 77 |
| Fragment 6 | SEQ ID NOS: 78, 18 |
| Fragment 7 | SEQ ID NOS: 72, 79 |
| Fragment 8 | SEQ ID NOS: 80, 18 |
| Fragment 9 | SEQ ID NOS: 74, 75 |
| Fragment 10 | SEQ ID NOS: 76, 77 |

A pDCM2-ΔNcgl1021 vector not replicable in *Corynebacterium glutamicum* was treated with a restriction enzyme, scal. After an isothermal assembly cloning reaction of RspmetZ_3 and fragment 1, fragment 2, RspmetZ_65 and fragment 3, fragment 4, RspmetZ_104 and fragment 5, fragment 6, RspmetZ_196 and fragment 7, fragment 8, RspmetZ_3_65_104 and fragment 1, fragment 11, fragment 12, fragment 6, each product was then transformed to *E. coli* DH5α, followed by smearing the same on an LB solid medium containing kanamycin (25 mg/L). Colonies transformed with the vector, in which the target gene was inserted, were selected through PCR, and a total of six kinds of plasmids were obtained using a plasmid extraction method, which was then named pDCM2-ΔNcgl1021-PsplRspmetZ_long, pDCM2-ΔNcgl1021-PsplRspmetZ_3, pDCM2-ΔNcgl1021-PsplRspmetZ_65, pDCM2-ΔNcgl1021-PsplRspmetZ_104, pDCM2-ΔNcgl1021-PsplRspmetZ_196, pDCM2-ΔNcgl1021-PsplRspmetZ_3_65_104, respectively.

Example 4: Preparation and Culture of Foreign *metZ*-Introduced Strain

The nine kinds of foreign *metZ* genes were introduced into the CM02-0618 strain which is a methionine-producing strain prepared in Example 2, respectively.

In detail, the CM02-0618 strain which is a methionine-producing strain prepared in Example 2 was transformed by homologous recombination on the chromosome with the pDCM2-ΔNcgl1021, pDCM2-ΔNcgl1021-PsplCvimetZ pDCM2-ΔNcgl1021-PsplHnemetZ, pDCM2-ΔNcgl1021-PsplRspmetZ, pDCM2-ΔNcgl1021-PsplRspmetZ_long, pDCM2-ΔNcgl1021-PsplRspmetZ_3, pDCM2-ΔNcgl1021-PsplRspmetZ_65, pDCM2-ΔNcgl1021-PsplRspmetZ_104, pDCM2-ΔNcgl1021-PsplRspmetZ_196, and pDCM2-ΔNcgl1021-PsplRspmetZ_3_65_104 vectors prepared in Example 3 by electroporation, respectively (van der Rest et al., *Appl Microbiol Biotechnol* 52:541-545, 1999).

Thereafter, secondary recombination was carried out on a solid medium containing sucrose. The transformed *Corynebacterium glutamicum* strain, in which the secondary recombination had been completed, was subjected to PCR using SEQ ID NOS: 23 and 24 to identify a strain in which the Ncgl1021 gene was deleted and a strain in which Ncgl1021 was deleted and the *metZ* gene was inserted. The recombinant strains, each prepared by introducing one of the nine kinds of vectors into CM02-0618, were named CM02-0618/ΔNcgl1021 and CM02-0757, CM02-0758, CM02-0759-1, CM02-0759-2, CM02-0759-3, CM02-0759-4, CM02-0759-5, and CM02-0759, respectively.

In order to analyze the L-methionine producing ability of the prepared strains, each strain was cultured together with their parent strain CM02-0618 in the following manner.

Each of the strains was inoculated into a 250 mL corner-baffled flask containing 25 mL of a medium below, and then cultured with shaking at 30° C. at 200 rpm for 20 hours. Thereafter, 1 mL of the seed culture medium was inoculated into a 250 mL corner-baffled flask containing 24 mL of a production medium, and then cultured with shaking at 30° C. at 200 rpm for 48 hours. The compositions of the seed medium and production medium are as follows.

<Seed Medium (pH 7.0)>
glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium pantothenate 2000 μg, nicotinamide 2000 μg (based on 1 L of distilled water)

<Production Medium (pH 8.0)>
glucose 50 g, $(NH_4)_2S_2O_3$ 12 g, Yeast extract 5 g, $KH_2PO_4$ 1 g, $MgSO_4 \cdot 7H_2O$ 1.2 g, biotin 100 μg, thiamine HCl 1000 μg, calcium pantothenate 2000 μg, nicotinamide 3000 μg, $CaCO_3$ 30 g, cobalamin (Vitamin B12) 1 μg (based on 1 L of distilled water).

Further, in order to compare with the sulfur source used in the existing methionine-converting enzyme, the sulfur source used in the production medium was replaced from thiosulfate ($S_2O_3$) to methyl mercaptan ($CH_3SH$), and the strains were cultured in the same manner. After completing each culture, the L-methionine concentration in each culture medium was analyzed and shown in Table 8.

TABLE 8

Verification of L-methionine producing ability of metZ expression-enhanced strains

| Strain | L-Methionine (g/L) (sulfur source: $S_2O_3$) | L-Methionine (g/L) (sulfur source: $CH_3SH$) |
|---|---|---|
| CM02-0618 | 0.04 | 0.01 |
| CM02-0618ΔNcgl021 | 0.04 | 0.01 |
| CM02-0757 (CvimetZ) | 0.13 | 0.02 |
| CM02-0758 (HnemetZ) | 0.12 | 0.01 |
| CM02-0759-1 (RspmetZ) | 0.13 | 0.02 |
| CM02-0759-2 (RspmetZ_long) | 0.13 | 0.02 |
| CM02-0759-3 (RspmetZ_3) | 0.13 | 0.02 |
| CM02-0759-4 (RspmetZ_65) | 0.13 | 0.02 |
| CM02-0759-5 (RspmetZ_104) | 0.13 | 0.02 |
| CM02-0759-6 (RspmetZ_196) | 0.13 | 0.02 |
| CM02-0759 (RspmetZ_3_65_104) | 0.14 | 0.02 |

As a result, when the nine kinds of *metZ* genes were introduced, respectively, L-methionine productivity was increased by 266% or more, as compared with that of the control strain, indicating that the foreign *metZ* of the present disclosure greatly increases L-methionine productivity through sulfhydrylation, and in particular, the efficiency is high, as compared with use of methyl mercaptan as a sulfur source in the existing method. This may interpret that unlike *Corynebacterium glutamicum* metB and metY, the foreign *metZ* of the present disclosure did not receive feedback inhibition, and thus the methionine yield increased.

The CM02-0757, CM02-0758, and CM02-0759 strains were deposited at the Korean Culture Center of Microorganisms, an international depositary, on May 2, 2019, under the provisions of the Budapest Treaty and assigned Accession Nos. KCCM12506P, KCCM12507P, KCCM12508P, respectively.

Example 5: Preparation of Recombinant Vector for Deletion of metB and metY Genes To examine function (activity) of the protein encoded by *metZ* of the present disclosure and to compare the activity with metY and metB activity, metB and metY possessed by C.gl were deleted, respectively. In detail, to delete metB and metY genes, respectively, recombinant plasmid vectors were prepared by way of the following method. Based on nucleotide sequences reported in GenBank of the U.S. National Institutes of Health (NIH), the metB and metY genes and their surrounding sequences (SEQ ID NOS: 25 and 26) of *Corynebacterium glutamicum* were obtained.

For the purpose of obtaining the deleted metB and metY genes, respectively, PCR was carried out with the chromosomal DNA of *Corynebacterium glutamicum* ATC 3032 as a template using primers of SEQ ID NOS: 27 and 28 and SEQ ID NOS: 29 and 30 (metB) and primers of SEQ ID NOS: 31 and 32 and SEQ ID NOS: 33 and 34 (metY) (Table 9).

TABLE 9

| SEQ ID NO | Sequence (5'-3') |
|---|---|
| 27 | GAATTCGAGCTCGGTACCCGGGCCAGTAAGGTGTTACCCATGC |
| 28 | CTGCTTGCCGCCAAATAGTTTAGTACTGGTAGATCAACTCCTGTAATCAGAATTCTA |
| 29 | TAGAATTCTGATTACAGGAGTTGATCTACCAGTACTAAACTATTTGGCGGCAAGCAG |
| 30 | TCGACTCTAGAGGATCCCCGGGCGATCTCAATTCCCATGCCTC |
| 31 | TCGAGCTCGGTACCCCTGCAATAGCTGCAAAGTGG |
| 32 | TGAGTCTATTTAAAGCGGGTAATTTTCTTGACTTT |
| 33 | CAAGAAAATTACCCGCTTTAAATAGACTCACCCCA |
| 34 | CTCTAGAGGATCCCCGCCTTAATTTGGGCGGATTG |

PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes. As a result, DNA fragments of 700 bp were obtained, respectively.

A pDCM2 vector not replicable in *Corynebacterium glutamicum*, and the amplified metB and metY gene fragments were treated with a restriction enzyme, smal, for chromosomal introduction, respectively. After ligation using a DNA ligase, a product was then transformed to *E. coli* DH5α, followed by smearing the same on an LB solid medium containing kanamycin (25 mg/L). Colonies transformed with each vector, in which deleted fragments of the target genes were inserted, were selected through PCR, and each plasmid was obtained using a plasmid extraction method, and the obtained plasmids were then named pDCM2-ΔmetB and pDCM2-ΔmetY, respectively.

Example 6: Preparation and Culture of metB or metY Gene-Deleted Strain from Three Kinds of metZ-Enhanced Strains CM02-0618, CM02-0757, CM02-0758, and CM02-0759 strains were transformed by homologous recombination on the chromosome with the pDCM2-ΔmetB and pDCM2-ΔmetY vectors prepared above by electroporation, respectively (van der Rest et al., *Appl Microbiol Biotechnol* 52:541-545, 1999). Thereafter, secondary recombination was carried out on a solid medium containing sucrose. The transformed *Corynebacterium glutamicum* strains, in which the secondary recombination had been completed, were examined for deletion of the metB and metY genes using SEQ ID NOS: 35 and 36 (metB) and SEQ ID NOS: 37 and 38 (metY) (Table 10), respectively.

TABLE 10

| SEQ ID NO | Sequence (5'-3') |
|---|---|
| 35 | TTCCTGGTCTGACGACAGTG |
| 36 | GATGTCTTCAGCTTCACCCTG |
| 37 | CCGAGGATAATCCACAAGGT |
| 38 | CGAAGCGTTCGTCGATTTCT |

These recombinant strains were named *Corynebacterium glutamicum* CM02-0618/ΔmetB CM02-0757/ΔmetB, CM02-0758/ΔmetB, CM02-0759/ΔmetB, CM02-0618/ΔmetY, CM02-0757/ΔmetY, CM02-0758/ΔmetY, CM02-0759/ΔmetY, respectively.

To analyze L-methionine producing ability of the prepared CM02-0618/ΔmetB, CM02-0757/ΔmetB, CM02-0758/ΔmetB, CM02-0759/ΔmetB, CM02-0618/ΔmetY, CM02-0757/ΔmetY, CM02-0758/ΔmetY, and CM02-0759/ΔmetY strains, they were cultured by way of the following method, respectively.

CM02-0618, CM02-0757, CM02-0758, and CM02-0759 as parent strains and CM02-0618/ΔmetB, CM02-0757/ΔmetB, CM02-0758/ΔmetB, CM02-0759/ΔmetB, CM02-0618/ΔmetY, CM02-0757/ΔmetY, CM02-0758/ΔmetY, and CM02-0759/ΔmetY prepared above were inoculated into a 250 mL corner-baffled flask containing 25 mL of a medium below, respectively, and then cultured with shaking at 30° C. at 200 rpm for 20 hours. Thereafter, 1 mL of each seed culture medium was inoculated into a 250 mL corner-baffled flask containing 24 mL of a production medium, and then cultured with shaking at 30° C. at 200 rpm for 48 hours. The compositions of the seed medium and production medium are as follows.

<Seed Medium (pH 7.0)>
glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium pantothenate 2000 μg, nicotinamide 2000 μg (based on 1 L of distilled water)
<Production Medium (pH 8.0)>
glucose 50 g, $(NH_4)_2S_2O_3$ 12 g, yeast extract 5 g, $KH_2PO_4$ 1 g, $MgSO_4 \cdot 7H_2O$ 1.2 g, biotin 100 μg, thiamine HCl 1000 μg, calcium pantothenate 2000 μg, nicotinamide 3000 μg, $CaCO_3$ 30 g, cobalamin (Vitamin B12) 1 μg (based on 1 L of distilled water).

The concentrations of L-methionine and a by-product homolanthionine in each culture medium cultured by the above culturing method were analyzed and shown in Table 11.

TABLE 11

Verification of L-methionine or homolanthionine producing ability of metY or metB-deleted strains

| Strain | L-Methionine (g/L) | Homolanthionine (g/L) |
|---|---|---|
| CM02-0618 | 0.04 | 0.82 |
| CM02-0618/ΔmetB | 0.03 | 0 |
| CM02-0618/ΔmetY | 0.02 | 0.81 |
| CM02-0757 | 0.13 | 0.17 |
| CM02-0758 | 0.12 | 0.17 |
| CM02-0759 | 0.13 | 0.18 |
| CM02-0757/ΔmetB | 0.13 | 0 |
| CM02-0758/ΔmetB | 0.12 | 0 |
| CM02-0759/ΔmetB | 0.13 | 0 |
| CM02-0757/ΔmetY | 0.08 | 0.19 |
| CM02-0758/ΔmetY | 0.07 | 0.18 |
| CM02-0759/ΔmetY | 0.08 | 0.19 |

From the results, it was confirmed that the foreign *metZ* performs the same function as metB, i.e., produces methionine through transsulfuration using cysteine as a sulfur source. In other words, even though metB or metY is deleted, methionine production may be maintained in a high yield by using *metZ*, and therefore, the gene may be replaced with foreign *metZ* to compensate for the shortcomings of metB and/or metY in *Corynebacterium*.

Further, in the strain, in which metB was present and foreign *metZ* was introduced, methionine production was enhanced and homolanthionine production was only about 20% compared to the control (CM02-0618), indicating that production of the by-product homolanthionine is reduced when *metZ* is enhanced. Homolanthionine is a substance synthesized by consuming O-acetylhomoserine, and thus the production of homolanthionine reduces methionine production. The foreign *metZ*, which inhibits the by-product production, compensates for the shortcomings of metB to inhibit the by-product production and to enhance the methionine synthesis.

The above results revealed for the first time that *metZ* of the present disclosure may mediate transsulfuration by using cysteine, and *metZ* of the present disclosure may be used not only to increase the methionine production but also to compensate for the shortcomings of metB of the genus *Corynebacterium* strain.

Example 7: Preparation of Recombinant Vector for Simultaneous Enhancement of metH and cysI In the present Example, to prepare a methionine-producing strain in which mcbR is not deleted, a vector for enhancing metH encoding methionine synthase (Ncgl1450) and cysI encoding sulfite reductase (Ncgl2718) at the same time was prepared.

In detail, to additionally insert the metH and cysI genes into the chromosome of *Corynebacterium* ATC 3032, a recombinant plasmid vector was prepared by way of the following method. Based on nucleotide sequences reported in GenBank of the U.S. National Institutes of Health (NIH), the metH gene and its surrounding sequence (SEQ ID NO: 39) and the cysI gene and its surrounding sequence (SEQ ID NO: 40) of *Corynebacterium glutamicum* were obtained.

For the purpose of obtaining the metH and cysI gene, PCR was carried out with the chromosomal DNA of *Corynebacterium glutamicum* ATC 3032 as a template using primers of SEQ ID NO: 41 and SEQ ID NO: 42, and SEQ ID NO: 43 and SEQ ID NO: 44. A Pcj7 promoter was used for enhancing expression of the metH gene, and a Pspl1 promoter was used for enhancing expression of the cysI gene. To obtain each promoter, PCR was carried out for Pcj7 with the chromosomal DNA of *Corynebacterium ammoniagenes* ATCC6872 as a template using SEQ ID NOS: 45 and 46, and for Pspl1 with the previously disclosed spl1-GFP (KR 10-1783170 B1) vector DNA as a template using SEQ ID NOS: 47 and 48. Sequences of the used primers are shown in Table 12 below.

TABLE 12

| SEQ ID NO | Sequence (5'-3') |
|-----------|------------------|
| 41 | CAACGAAAGGAAACAATGTCTACTTCAGTTACTTC |
| 42 | TAGTCAGAGAGTGATTTAGACGTTAAAGTACTTTG |
| 43 | ATCAAAACAGATATCATGACAACAACCACCGGAAG |
| 44 | CGCTAGTCAGAGAGTTCACACCAAATCTTCCTCAG |
| 45 | CCGATCAGCGTAAGTAGAAACATCCCAGCGCTACT |
| 46 | AACTGAAGTAGACATTGTTTCCTTTCGTTGGGTAC |

TABLE 12-continued

| SEQ ID NO | Sequence (5'-3') |
|-----------|------------------|
| 47 | TACTTTAACGTCTAAGGTACCGGCGCTTCATGTCA |
| 48 | GGTGGTTGTTGTCATGATATCTGTTTTGATCTCCT |

PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 4 minutes, followed by polymerization at 72° C. for 7 minutes. As a result, metH and cysI, Pcj7 promoter and Pspl1 promoter DNA fragments were obtained, respectively.

A pDCM2-ΔNcgl1021 vector not replicable in *Corynebacterium glutamicum* was treated with a restriction enzyme, scal, and the four amplified DNA fragments were treated with scal for chromosomal introduction. After IST reaction, a product was then transformed to *E. coli* DH5α, followed by smearing the same on an LB solid medium containing kanamycin (25 mg/L). Colonies transformed with the vector, in which deleted fragments of the target genes were inserted, were selected through PCR, and a plasmid was obtained using a plasmid extraction method, which was then named pDCM2-ΔNcgl1021-Pcj7metH-Pspl1cysI.

Example 8: Preparation of Strain for Simultaneous Enhancement of metH and cysI and Production of L-Methionine Using the Same ATCC13032 strain was transformed by homologous recombination on the chromosome with the pDCM2-ΔNcgl1021 and pDCM2-ΔNcgl1021-Pcj7metH-Pspl1cysI vectors prepared above by electroporation (van der Rest et al., *Appl Microbiol Biotechnol* 52:541-545, 1999), respectively. Thereafter, secondary recombination was carried out on a solid medium containing sucrose. The transformed *Corynebacterium glutamicum* strains, in which the secondary recombination had been completed, were examined for deletion of the Ncgl1021 gene and insertion of the Pcj7-metH-Pspl1cysI gene using SEQ ID NOS: 23 and 24, respectively. The recombinant strains were named 13032/ΔNcgl1021 and CM02-0753, respectively.

To analyze L-methionine producing ability of the prepared 13032/ΔNcgl1021 and CM02-0753 strains, they were cultured together with a parent *Corynebacterium glutamicum* ATCC13032 strain by way of the following method, respectively.

*Corynebacterium glutamicum* ATCC13032 and the 13032/ΔNcgl1021 and CM02-0753 strains prepared above were inoculated into a 250 mL corner-baffled flask containing 25 mL of a medium below, respectively, and then cultured with shaking at 30° C. at 200 rpm for 20 hours. Thereafter, 1 mL of each seed culture medium was inoculated into a 250 mL corner-baffled flask containing 24 mL of a production medium, and then cultured with shaking at 30° C. at 200 rpm for 48 hours. The compositions of the seed medium and production medium are as follows.

<Seed Medium (pH 7.0)> glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 100 µg, thiamine HCl 1000 µg, calcium pantothenate 2000 µg, nicotinamide 2000 µg (based on 1 L of distilled water)

<Production Medium (pH 8.0)> glucose 50 g, $(NH_4)_2S_2O_3$ 12 g, yeast extract 5 g, $KH_2PO_4$ 1 g, $MgSO_4\cdot7H_2O$ 1.2 g, biotin 100 µg, thiamine HCl 1000 µg, calcium pantothenate 2000 µg, nicotinamide 3000 µg, $CaCO_3$ 30 g, cobalamin (Vitamin B12) 1 µg (based on 1 L of distilled water).

The concentrations of L-methionine in each culture medium cultured by the above culturing method were analyzed and shown in Table 13.

TABLE 13

| Verification of L-methionine producing ability of strain having mcbR | |
| --- | --- |
| Strain | L-Methionine (g/L) |
| Corynebacterium glutamicum ATCC13032 (wild-type) | 0 |
| 13032/ΔNcgl1021 | 0 |
| CM02-0753 | 0.03 |

As a result, it was confirmed that the L-methionine production ability of the metH and cysI-overexpressing strain, in which mcbR was still present, was improved by 0.03 g/L, as compared to the control strain.

Example 9-1: Preparation of Vector for Enhancement of *metZ* Genes at Other Sites than Ncgl1021 Site To insert the three kinds of foreign *metZ* genes into other sites than the existing site on the chromosome of *Corynebacterium* ATCC13032, recombinant plasmid vectors were prepared by way of the following method.

First, to insert *metZ*, a vector for deleting Ncgl2748 (Transposase) was prepared. Based on nucleotide sequences reported in GenBank of the U.S. National Institutes of Health (NIH), Ncgl2748 and its surrounding sequence (SEQ ID NO: 49) of *Corynebacterium glutamicum* were obtained. For the purpose of obtaining the deleted Ncgl2748 gene, PCR was carried out with the chromosomal DNA of *Corynebacterium glutamicum* ATC 3032 as a template using primers of SEQ ID NO: 50 and SEQ ID NO: 51, and SEQ ID NO: 52 and SEQ ID NO: 53 (Table 14). PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 30 seconds, followed by polymerization at 72° C. for 7 minutes. As a result, DNA fragments were obtained, respectively.

TABLE 14

| SEQ ID NO | Sequence (5'-3') |
| --- | --- |
| 50 | GTACCCGGGGATCCTCTAGACCTGGGTAACTTCCTGTCCA |
| 51 | CAGGTTAGCAGTACTTCTCAAGTTTCTCGGCGGTG |
| 52 | AACTTGAGAAGTACTGCTAACCTGCAGAAACCTTG |
| 53 | GCCTGCAGGTCGACTCTAGACTCCGCAGAAATCGTGGGC |

A pDCM2 vector not replicable in *Corynebacterium glutamicum* and the amplified Ncgl2748 gene fragments were treated with a restriction enzyme, smaI, for chromosomal introduction. After IST reaction, a product was then transformed to *E. coli* DH5α, followed by smearing the same on an LB solid medium containing kanamycin (25 mg/L). Colonies transformed with the vector, in which deleted fragments of the target genes were inserted, were selected through PCR, and a plasmid was obtained using a plasmid extraction method, which was then named pDCM2-ΔNcgl2748.

For the purpose of obtaining the three kinds of *metZ* genes (*Chromobacterium violaceum, Hyphomonas neptunium, Rhodobacter sphaeroides*), PCR was carried out with the prepared pDCM2-ΔNcgl1021-PsplCvimetZ (*Chromobacterium violaceum metZ*), pDCM2-ΔNcgl1021-PsplHnemetZ (*Hyphomonas neptunium metZ*), and pDCM2-ΔNcgl1021-PsplRspmetZ (*Rhodobacter sphaeroides metZ*) vectors as a template using SEQ ID NOS: 54 and 55, 54 and 56, and 54 and 57 (Table 15). PCR was carried out under following conditions: denaturation at 95° C. for 5 minutes, a total of 30 cycles consisting of denaturation at 95° C. for 30 seconds, annealing at 53° C. for 30 seconds, and polymerization at 72° C. for 60 seconds, followed by polymerization at 72° C. for 7 minutes. As a result, three kinds of DNA fragments were obtained.

TABLE 15

| SEQ ID NO | Sequence (5'-3') |
| --- | --- |
| 54 | CGCCGAGAAACTTGAGAAGTGGCGCTTCATGTCAA |
| 55 | CTGCAGGTTAGCAGTTTAGTCAAGGCCCCGCAACA |
| 56 | CTGCAGGTTAGCAGTTCACAAGCTGTTAAGCGAAG |
| 57 | CTGCAGGTTAGCAGTTCAGATCACCGCGAGCGCCT |

A pDCM2-ΔNcgl2748 vector not replicable in *Corynebacterium glutamicum* was treated with a restriction enzyme, scaI. After IST reaction with the amplified fragments according to each strain, a product was then transformed to *E. coli* DH5α, followed by smearing the same on an LB solid medium containing kanamycin (25 mg/L). Colonies transformed with the vector, in which the target gene was inserted, were selected through PCR, and a total of three plasmids were obtained using a plasmid extraction method, which were then named pDCM2-ΔNcgl2748-PsplCvimetZ (*Chromobacterium violaceum metZ*), pDCM2-ΔNcgl2748-PsplHnemetZ (*Hyphomonas neptunium metZ*), pDCM2-ΔNcgl2748-PsplRspmetZ (*Rhodobacter sphaeroides metZ*), respectively.

Example 9-2: Preparation of Vector for Enhancement of *metZ* Genes at Other Sites than Ncgl1021 Site Additionally, to examine whether methionine production is also increased in a strain into which *metZ* gene having 99% or more sequence homology is introduced, vectors for the five *metZ* genes of Example 3-2 were additionally prepared.

Vectors, each introduced with one of the six *metZ* genes, were prepared in the same manner as in Example 9-1.

A total of six vectors were prepared as follows: named pDCM2-ΔNcgl2748-PsplRspmetZ_long, ΔNcgl2748-PsplRspmetZ_3, pDCM2-ΔNcgl2748-PsplRspmetZ_65, pDCM2-ΔNcgl2748-PsplRspmetZ_104, pDCM2-ΔNcgl2748-PsplRspmetZ_196, and pDCM2-ΔNcgl2748-PsplRspmetZ_3_65_104, respectively. To prepare these vectors, ΔNcgl1021-PsplRspmetZ_long pDCM2-ΔNcgl 021-PsplRspmetZ_3, pDCM2-ΔNcgl1021-PsplRspmetZ_65, pDCM2-ΔNcgl 021-PsplRspmetZ_104, pDCM2-

ΔNcgl1021-PsplRspmetZ_196, and pDCM2-ΔNcgl1021-PsplRspmetZ_3_65_104 prepared in Example 4 were used as a DNA template, respectively, and primers of SEQ ID NOS: 54 and 57 were commonly used. Other procedures were the same as in Example 9-1.

Example 10: Development of Foreign metZ-Enhanced Strain Based on L-Methionine-Producing Strain Having mcbR and Production of L-Methionine Using the Same CM02-0753 strain was transformed by homologous recombination on the chromosome with the pDCM2-ΔNcgl2748, pDCM2-ΔNcgl2748-PsplCvimetZ, pDCM2-ΔNcgl2748-PsplHnemetZ, pDCM2-ΔNcgl2748-PsplRspmetZ, pDCM2-ΔNcgl2748-PsplRspmetZ_long, pDCM2-ΔNcgl2748-PsplRspmetZ_3, pDCM2-ΔNcgl2748-PsplRspmetZ_65, pDCM2-ΔNcgl2748-PsplRspmetZ_104, pDCM2-ΔNcgl2748-PsplRspmetZ_196, and pDCM2-ΔNcgl2748-PsplRspmetZ_3_65_104 vectors prepared above by electroporation, respectively (van der Rest et al., *Appl Microbiol Biotechnol* 52:541-545, 1999). Thereafter, secondary recombination was carried out on a solid medium containing sucrose. The transformed *Corynebacterium glutamicum* strains, in which the secondary recombination had been completed, were examined for insertion of each foreign *metZ* gene at the Ncgl2748 site using SEQ ID NOS: 58 and 59 (Table 16), respectively.

TABLE 16

| SEQ ID NO | Sequence (5'-3') |
| --- | --- |
| 58 | TTCTCCGTGCCGAGAAAATC |
| 59 | GTAGATGATCTCGCCATTTG |

These recombinant strains were named *Corynebacterium glutamicum* 13032/ΔNcgl2748, CM02-0765, CM02-0766, CM02-0767-1, CM02-0767-2, CM02-0767-3, CM02-0767-4, CM02-0767-5, CM02-0767-6, CM02-0767, respectively.

To analyze L-methionine producing ability of the prepared strains, they were cultured together with the parent strain *Corynebacterium glutamicum* CM02-0753 by way of the following method, respectively.

Each strain was inoculated into a 250 mL corner-baffled flask containing 25 mL of a medium below, respectively, and then cultured with shaking at 30° C. at 200 rpm for 20 hours. Thereafter, 1 mL of each seed culture medium was inoculated into a 250 mL corner-baffled flask containing 24 mL of a production medium, and then cultured with shaking at 30° C. at 200 rpm for 48 hours. The compositions of the seed medium and production medium are as follows.

<Seed Medium (pH 7.0)>
glucose 20 g, peptone 10 g, yeast extract 5 g, urea 1.5 g, $KH_2PO_4$ 4 g, $K_2HPO_4$ 8 g, $MgSO_4 \cdot 7H_2O$ 0.5 g, biotin 100 μg, thiamine HCl 1000 μg, calcium pantothenate 2000 μg, nicotinamide 2000 μg (based on 1 L of distilled water)

<Production Medium (pH 8.0)>
glucose 50 g, $(NH_4)_2S_2O_3$ 12 g, yeast extract 5 g, $KH_2PO_4$ 1 g, $MgSO_4 \cdot 7H_2O$ 1.2 g, biotin 100 μg, thiamine HCl 1000 μg, calcium pantothenate 2000 μg, nicotinamide 3000 μg, $CaCO_3$ 30 g, cobalamin (Vitamin B12) 1 μg (based on 1 L of distilled water).

The concentrations of L-methionine in each culture medium cultured by the above culturing method were analyzed and shown in Table 17.

TABLE 17

Verification of L-methionine producing ability by overexpression of foreign metZ in strain having mcbR

| Strain | L-Methionine (g/L) |
| --- | --- |
| CM02-0753 | 0.03 |
| CM02-0753/ΔNcgl2748 | 0.03 |
| CM02-0765 (CvimetZ) | 0.10 |
| CM02-0766 (HnemetZ) | 0.09 |
| CM02-0767-1 (RspmetZ) | 0.10 |
| CM02-0767-2 (RspmetZ_long) | 0.10 |
| CM02-0767-3 (RspmetZ_3) | 0.10 |
| CM02-0767-4 (RspmetZ_65) | 0.10 |
| CM02-0767-5 (RspmetZ_104) | 0.10 |
| CM02-0767-6 (RspmetZ_196) | 0.10 |
| CM02-0767 (RspmetZ_3_65_104) | 0.11 |

As a result, it was confirmed that when the foreign *metZ* genes were introduced into the methionine-producing strain having mcbR, respectively, the methionine yield was also increased.

CM02-0765, CM02-0766, and CM02-0767 were deposited at the Korean Culture Center of Microorganisms, an international depositary, on May 2, 2019, under the provisions of the Budapest Treaty and assigned Accession Nos. KCCM12509P, KCCM12510P, and KCCM12511P, respectively.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds, are therefore intended to be embraced by the claims.

Effect of the Invention

A microorganism, into which activity of a protein encoded by *metZ* of the present disclosure is introduced, exhibits a high yield, because it produces fewer by-products, as compared with metY, and the microorganism does not receive feedback inhibition, unlike metB receiving feedback inhibition by methionine, and thus produces L-methionine in a high yield, thereby being usefully applied to industrial production of L-methionine.

---

What is claimed is:

1. A method of producing L-methionine, the method comprising culturing an L-methionine producing microorganism of the genus *Corynebacterium*, into which a protein encoded by a foreign *metZ* gene is introduced, in a medium containing thiosulfate, thereby producing L-methionine, wherein the protein has O-acylhomoserine transsulfurase activity.

2. The method of producing L-methionine of claim 1, wherein the protein is derived from *Chromobacterium violaceum, Hyphomonas neptunium*, or *Rhodobacter sphaeroides*.

3. The method of producing L-methionine of claim 1, wherein the protein has at least 90% sequence identity to SEQ ID NOS: 60, 61, or 62.

4. The method of producing L-methionine of claim 1, wherein the microorganism includes one or more genetic modifications selected from the group consisting of attenuation or inactivation of activity of cystathionine gamma synthase; attenuation or inactivation of activity of O-acetyl-homoserine sulfhydrylase; attenuation or inactivation of activity of methionine-cysteine biosynthesis repressor protein; enhancement of activity of methionine synthase; and enhancement of activity of sulfite reductase, wherein the enhancement of activity of the polypeptide or protein is achieved by:

1) a method of increasing the intracellular copy number of a gene or polynucleotide encoding the polypeptide or protein;

2) a method of replacing a gene expression regulatory region on the chromosome encoding the polypeptide or protein with a sequence having a strong activity;

3) a method of modifying a nucleotide sequence of a start codon or 5'-UTR region of the polypeptide or protein;

4) a method of modifying a polynucleotide sequence on the chromosome to increase the activity of the polypeptide or protein;

5) a method of introducing a foreign polynucleotide exhibiting the activity of the polypeptide or protein, or introducing a variant polynucleotide by codon-optimization of the polynucleotide; or 6) a combination of two or more selected from 1) to 5) above, wherein the inactivation or attenuation of the activity of the protein is achieved by:

1) a method of deleting all or a part of the gene encoding the protein;

2) a method of modifying the expression regulatory region (or expression regulatory sequence) such that the expression of the gene encoding the protein is decreased;

3) a method of modifying the gene sequence encoding the protein such that the protein activity is removed or weakened;

4) a method of introducing an antisense oligonucleotide that binds complementarily to a transcript of the gene encoding the protein;

5) a method of adding a complementary sequence to the Shine-Dalgarno sequence upstream of the Shine-Dalgarno sequence of the gene encoding the protein to form a secondary structure, thereby inhibiting the ribosomal binding;

6) a reverse transcription engineering (RTE) method of adding a promoter at the 3' terminus of an open reading frame (ORF) of the polynucleotide sequence of the gene encoding the protein so as to be reversely transcribed; or 7) a combination of two or more selected from 1) to 6) above.

5. The method of producing L-methionine of claim 1, wherein the microorganism is *Corynebacterium glutamicum*.

6. The method of producing L-methionine of claim 1, comprising recovering L-methionine from the microorganism or medium.

7. The method of producing L-methionine of claim 1, wherein homolanthionine production is reduced.

* * * * *